United States Patent
Oh et al.

(10) Patent No.: US 11,785,846 B2
(45) Date of Patent: Oct. 10, 2023

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hong-Se Oh, Gyeonggi-do (KR); Young-Kwang Kim, Gyeonggi-do (KR); Doo-Hyeon Moon, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 0 days.

(21) Appl. No.: 17/690,331

(22) Filed: Mar. 9, 2022

(65) Prior Publication Data
US 2022/0209137 A1    Jun. 30, 2022

Related U.S. Application Data

(63) Continuation of application No. 16/481,531, filed as application No. PCT/KR2018/001920 on Feb. 14, 2018, now abandoned.

(30) Foreign Application Priority Data

Feb. 15, 2017 (KR) .......................... 10-2017-0020538

(51) Int. Cl.
| | | |
|---|---|---|
| *C07D 213/24* | (2006.01) |
| *C07D 239/26* | (2006.01) |
| *C07D 251/24* | (2006.01) |
| *H01L 51/00* | (2006.01) |
| *H01L 51/50* | (2006.01) |
| *H10K 85/60* | (2023.01) |
| *H10K 50/15* | (2023.01) |
| *H10K 50/16* | (2023.01) |

(52) U.S. Cl.
CPC ....... *H10K 85/6572* (2023.02); *H10K 85/622* (2023.02); *H10K 85/633* (2023.02); *H10K 85/654* (2023.02); *H10K 50/15* (2023.02); *H10K 50/16* (2023.02)

(58) Field of Classification Search
None
See application file for complete search history.

(56) References Cited

FOREIGN PATENT DOCUMENTS

WO    WO-2015152633 A1 * 10/2015 ........... C07D 209/82
WO    WO-2015152644 A1 * 10/2015 ........... C07C 255/51

* cited by examiner

*Primary Examiner* — Vu A Nguyen
(74) *Attorney, Agent, or Firm* — G. Creston Campbell

(57) ABSTRACT

The present disclosure relates to an organic electroluminescent compound and an organic electroluminescent device comprising the same. The organic electroluminescent compound of the present disclosure has a high glass transition temperature that can be used in a deposition process. Further, by comprising the organic electroluminescent compound of the present disclosure, an organic electroluminescent device having a low driving voltage, high luminous efficiency, and/or improved lifespan characteristics can be provided.

8 Claims, No Drawings

ORGANIC ELECTROLUMINESCENT COMPOUND AND ORGANIC ELECTROLUMINESCENT DEVICE COMPRISING THE SAME

CLAIM OF BENEFIT OF PRIOR APPLICATION

This application claims priority under 35 U.S.C. § 120 from U.S. patent application Ser. No. 16/481,531, filed Jul. 29, 2019, which is the National Stage Entry of PCT/KR2018/001920, filed Feb. 14, 2018, both of which are incorporated by reference herein in their entirety.

TECHNICAL FIELD

The present disclosure relates to an organic electroluminescent compound and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

An organic EL device (OLED) changes electric energy into light by applying electricity to an organic light-emitting material, and commonly comprises an anode, a cathode, and an organic layer formed between the two electrodes. The organic layer of the OLED may comprise a hole injection layer, a hole transport layer, an electron blocking layer, a light-emitting layer (containing host and dopant materials), an electron buffer layer, a hole blocking layer, an electron transport layer, an electron injection layer, etc. The materials used in the organic layer can be classified into a hole injection material, a hole transport material, an electron blocking material, a light-emitting material, an electron buffer material, a hole blocking material, an electron transport material, an electron injection material, etc., depending on functions. In the OLED, holes from an anode and electrons from a cathode are injected into a light-emitting layer by the application of electric voltage, and an exciton having high energy is produced by the recombination of the holes and electrons. The organic light-emitting compound moves into an excited state by the energy and emits light from energy when the organic light-emitting compound returns to the ground state from the excited state.

Studies have been continuing to improve the performance of organic electroluminescent devices by using materials suitable for the respective layers in organic electroluminescent devices.

For example, an electron transport material actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. Organic metal complexes having light-emitting function such as $Alq_3$ are excellent in transporting electrons, and thus have been conventionally used as an electron transport material. However, $Alq_3$ has problems in that it moves to other layers and shows a reduction of color purity when used in blue light-emitting devices. Therefore, new electron transport materials have been required, which do not have the above problems, are highly electron-affinitive, and quickly transport electrons in organic EL devices to provide organic EL devices having high luminous efficiency.

In addition, an electron buffer layer is a layer capable of improving the problem that the current characteristics in the device changes upon exposure to a high temperature in a panel fabrication process to cause deformation of light emission luminance. The characteristics of the compound contained in the electron buffer layer are important for ensuring stability against high temperature exposure as well as similar current characteristics compared to devices without an electron buffer layer.

Meanwhile, high temperature may occur inside the organic electroluminescent device during driving. If the glass transition temperature (Tg) of an organic electroluminescent compound is low, crystallization and aggregation of the material may occur, and thus the lifespan of the organic electroluminescent device may be drastically reduced. Thus, an organic electroluminescent compound capable of withstanding heat at high temperatures is required.

Korean Patent Appln. Laying-Open No. KR 2013-0108183 A, and Korean Patent Nos. KR 1542714 B1 and KR 1537499 B1 disclose a compound wherein a triazine substituted with an aryl(s) is bonded directly or via a linker to a benzofluorene, as a compound for an electron transport layer or an electron buffer layer of an organic electroluminescent device. However, said references do not specifically disclose a compound wherein a triazine substituted with an aryl(s) is bonded directly or via a linker to a 5 carbon position of a benzo[b]fluorene.

DISCLOSURE OF THE INVENTION

Problems to be Solved

The objective of the present disclosure is to provide an organic electroluminescent compound which can efficiently produce an organic electroluminescent device having excellent driving voltage and/or luminous efficiency characteristics. At the same time or selectively, the objective of the present disclosure is to provide an organic electroluminescent compound which is resistant to high temperature deterioration and thus contributes to a long lifespan of the organic electroluminescent device.

Solution to Problems

As a method of increasing the Tg value (usually 130° C. or higher) to inhibit high temperature deterioration of an organic electroluminescent compound, a method of increasing molecular weight by introducing a substituent or forming a ring has been generally tried. However, the present inventors have recognized that this method has a limit due to increase of the deposition temperature. As a result of intensive studies, the present inventors found that an organic electroluminescent compound having a higher Tg value at the same molecular weight can be produced by controlling the binding position of the substituents exhibiting HUMO (highest occupied molecular orbital) and LUMO (lowest unoccupied molecular orbital) and the accompanying steric hindrance effect.

More specifically, the present inventors found that the above objective can be achieved by an organic electroluminescent compound represented by the following formula 1:

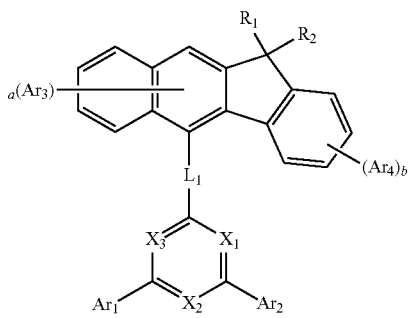

wherein

X₁ to X₃ each independently represent CH or N, with a proviso that at least one of X₁ to X₃ are N;

Ar₁ and Ar₂ each independently represent a substituted or unsubstituted (C6-C30)aryl, or a substituted or unsubstituted (5- to 30-membered)heteroaryl;

Ar₃ and Ar₄ each independently represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl;

L₁ represents a single bond, a substituted or unsubstituted (C6-C30)arylene, or a substituted or unsubstituted (5- to 30-membered)heteroarylene;

R₁ and R₂ each independently represent a substituted or unsubstituted (C1-C30)alkyl, a substituted or unsubstituted (C6-C30)aryl, or a substituted or unsubstituted (5- to 30-membered)heteroaryl; or are linked to each other to form a substituted or unsubstituted, mono- or polycyclic, (C3-C30) alicyclic, aromatic ring, or a combination thereof, whose carbon atom(s) may be replaced with at least one heteroatom selected from nitrogen, oxygen, and sulfur;

a represents an integer of 1 to 5, and b represents an integer of 1 to 4, in which if a and b represent an integer of 2 or more, each Ar₃ and each Ar₄ may be the same or different; and the heteroaryl(ene) and the heterocycloalkyl contain at least one heteroatom selected from B, N, O, S, Si, and P.

Effects of the Invention

By using the organic electroluminescent compound according to the present disclosure, an organic electroluminescent device having low driving voltage and/or high luminous efficiency characteristics can be produced. At the same time or selectively, it is possible to provide an organic electroluminescent compound which is resistant to high temperature deterioration and thus contributes to a long lifespan of the organic electroluminescent device.

EMBODIMENTS OF THE INVENTION

Hereinafter, the present disclosure will be described in detail. However, the following description is intended to explain the disclosure, and it is not meant in any way to restrict the scope of the disclosure.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. The compound represented by formula 1 may be comprised in at least one layer constituting an organic electroluminescent device, for example, an electron buffer layer and/or an electron transport layer, but is not limited thereto. When comprised in the electron buffer layer, the compound of formula 1 can be comprised as an electron buffer material. When comprised in the electron transport layer, the compound of formula 1 can be comprised as an electron transport material.

Hereinafter, the compound represented by formula 1 will be described in detail.

In formula 1 above, X₁ to X₃ each independently represent CH or N, with a proviso that at least one of X₁ to X₃ are N. Preferably, at least two of X₁ to X₃ are N. More preferably, all of X₁ to X₃ are N.

Ar₁ and Ar₂ each independently represent a substituted or unsubstituted (C6-C30)aryl, or a substituted or unsubstituted (5- to 30-membered)heteroaryl; preferably each independently represent a substituted or unsubstituted (C6-C25)aryl, or a substituted or unsubstituted (5- to 20-membered)heteroaryl; and more preferably each independently represent a (C6-C25)aryl unsubstituted or substituted with a (C1-C6) alkyl(s) or a (C6-C12)aryl(s), or a (5- to 20-membered) heteroaryl unsubstituted or substituted with a (C6-C12) aryl(s). According to one embodiment of the present disclosure, Ar₁ and Ar₂ may each independently represent phenyl, naphthyl, biphenyl, dimethylfluorenyl, diphenylfluorenyl, dimethylbenzofluorenyl, phenylpyridyl, dibenzofuranyl, dibenzothiophenyl, or phenylcarbazolyl.

Ar₃ and Ar₄ each independently represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; preferably each independently represent hydrogen, a substituted or unsubstituted (C6-C20)aryl, or a substituted or unsubstituted (5- to 20-membered)heteroaryl; and more preferably each independently represent hydrogen, an unsubstituted (C6-C20)aryl, or an unsubstituted (5- to 20-membered)heteroaryl. According to one embodiment of the present disclosure, Ar₃ and Ar₄ may each independently represent hydrogen, phenyl, naphthyl, biphenyl, or pyridyl.

L₁ represents a single bond, a substituted or unsubstituted (C6-C30)arylene, or a substituted or unsubstituted (5- to 30-membered)heteroarylene; preferably represents a single bond, a substituted or unsubstituted (C6-C20)arylene, or a substituted or unsubstituted (5- to 20-membered)heteroarylene; and more preferably represents a single bond, an unsubstituted (C6-C20)arylene, or an unsubstituted (5- to 20-membered)heteroarylene. According to one embodiment of the present disclosure, $L_1$ represents a single bond, phenylene, naphthylene, biphenylene, or pyridylene.

$R_1$ and $R_2$ each independently represent a substituted or unsubstituted (C1-C30)alkyl, a substituted or unsubstituted (C6-C30)aryl, or a substituted or unsubstituted (5- to 30-membered)heteroaryl; or are linked to each other to form a substituted or unsubstituted, mono- or polycyclic, (C3-C30) alicyclic, aromatic ring, or a combination thereof, whose carbon atom(s) may be replaced with at least one heteroatom selected from nitrogen, oxygen, and sulfur. Preferably, $R_1$ and $R_2$ each independently represent a substituted or unsubstituted (C1-C6)alkyl, or a substituted or unsubstituted (C6-C12)aryl; or are linked to each other to form a substituted or unsubstituted, mono- or polycyclic, (C5-C10) alicyclic, aromatic ring, or a combination thereof. More preferably, $R_1$ and $R_2$ each independently represent an unsubstituted (C1-C6)alkyl, or an unsubstituted (C6-C12) aryl; or are linked to each other to form an unsubstituted cyclopentane ring. According to one embodiment of the present disclosure, $R_1$ and $R_2$ may each independently represent methyl or phenyl; or are linked to each other to form a spirocyclopentane structure.

a represents an integer of 1 to 5, and b represents an integer of 1 to 4, in which if a and b represent an integer of 2 or more, each $Ar_3$ and each $Ar_4$ may be the same or different. Preferably, a and b each independently represent an integer of 1 to 2, and more preferably each independently represent 1.

According to one embodiment of the present disclosure, in formula 1 above, $X_1$ to $X_3$ each independently represent CH or N, with a proviso that at least two of $X_1$ to $X_3$ are N; $Ar_1$ and $Ar_2$ each independently represent a substituted or unsubstituted (C6-C25)aryl, or a substituted or unsubstituted (5- to 20-membered)heteroaryl; $Ar_3$ and $Ar_4$ each independently represent hydrogen, a substituted or unsubstituted (C6-C20)aryl, or a substituted or unsubstituted (5- to 20-membered)heteroaryl; $L_1$ represents a single bond, a substituted or unsubstituted (C6-C20)arylene, or a substituted or unsubstituted (5- to 20-membered)heteroarylene; $R_1$ and $R_2$ each independently represent a substituted or unsubstituted (C1-C6)alkyl, or a substituted or unsubstituted (C6-C12)aryl; or are linked to each other to form a substituted or unsubstituted, mono- or polycyclic, (C5-C10) alicyclic, aromatic ring, or a combination thereof; and a and b each independently represent an integer of 1 to 2.

According to another embodiment of the present disclosure, in formula 1 above, $X_1$ to $X_3$ each independently represent N; $Ar_1$ and $Ar_2$ each independently represent a (C6-C25)aryl unsubstituted or substituted with a (C1-C6) alkyl or a (C6-C12)aryl, or a (5- to 20-membered)heteroaryl unsubstituted or substituted with a (C6-C12)aryl; $Ar_3$ and $Ar_4$ each independently represent hydrogen, an unsubstituted (C6-C20)aryl, or an unsubstituted (5- to 20-membered) heteroaryl; $L_1$ represents a single bond, an unsubstituted (C6-C20)arylene, or an unsubstituted (5- to 20-membered) heteroarylene; $R_1$ and $R_2$ each independently represent an unsubstituted (C1-C6)alkyl, or an unsubstituted (C6-C12) aryl; or are linked to each other to form an unsubstituted cyclopentane; and a and b each independently represent 1.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is meant to be a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is meant to be a cycloalkyl having at least one heteroatom selected from the group consisting of B, N, O, S, Si, and P, preferably selected from the group consisting of O, S, and N, and 3 to 7 ring backbone atoms, preferably 5 to 7 ring backbone atoms, and includes tetrahydrofuran, pyrrolidine, thiolan, tetrahydropyran, etc. "(C6-C30)aryl(ene)" is meant to be a monocyclic or fused ring radical derived from an aromatic hydrocarbon having 6 to 30 ring backbone carbon atoms and may be partially saturated, in which the number of ring backbone carbon atoms is preferably 6 to 25, more preferably 6 to 18, includes a spiro structure, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(5- to 30-membered)heteroaryl(ene)" is meant to be an aryl group having at least one, preferably 1 to 4 heteroatoms selected from the group consisting of B, N, O, S, Si, and P, and 5 to 30 ring backbone atoms; is a monocyclic ring, or a fused ring condensed with at least one benzene ring; may be partially saturated; may be one formed by linking at least one heteroaryl or aryl group to a heteroaryl group via a single bond(s); includes a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. "Halogen" includes F, Cl, Br, and I.

Herein, "substituted" in the expression "substituted or unsubstituted" means that a hydrogen atom in a certain functional group is replaced with another atom or functional group, i.e., a substituent. Substituents of the substituted (C1-C30)alkyl, the substituted (C6-C30)aryl(ene), the substituted (5- to 30-membered)heteroaryl(ene), the substituted (3- to 7-membered)heterocycloalkyl, the substituted (C3-C30)cycloalkyl, and the substituted mono- or polycyclic, (C3-C30) alicyclic, aromatic ring, or a combination thereof in $Ar_1$ to $Ar_4$, $L_1$, $R_1$, and $R_2$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl(s); a (C6-C30)aryl unsubstituted or substituted with a (5- to 30-membered) heteroaryl(s); a tri(C1-C30)alkylsilyl, a tri(C6-C30)arylsilyl; a di(C1-C30)alkyl(C6-C30)arylsilyl; a (C1-C30)alkyldi(C6-C30)arylsilyl; an amino; a mono- or di-(C1-C30) alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30) alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl; and preferably each independently are a (C1-C6)alkyl or a (C6-C12)aryl. Specifically, the substituents may each independently be methyl or phenyl.

The compound represented by formula 1 includes the following compounds, but is not limited thereto:

C-1

C-2

C-3

C-4

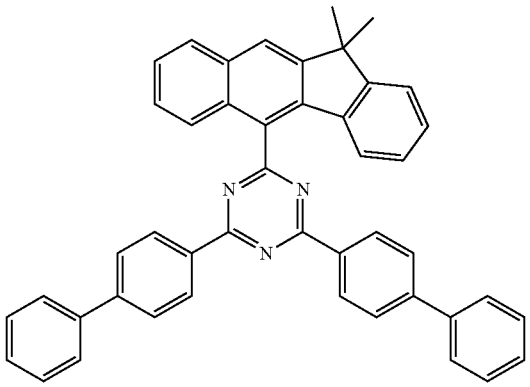

C-5

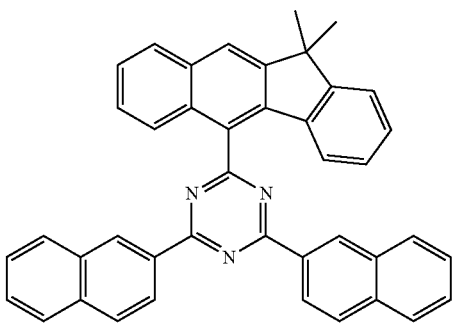

C-6

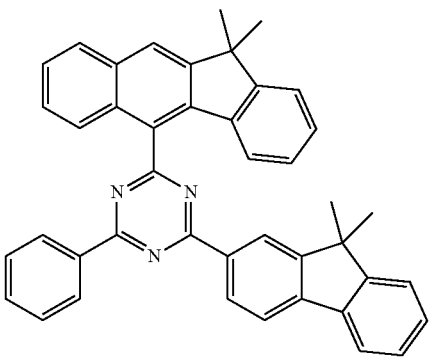

C-7

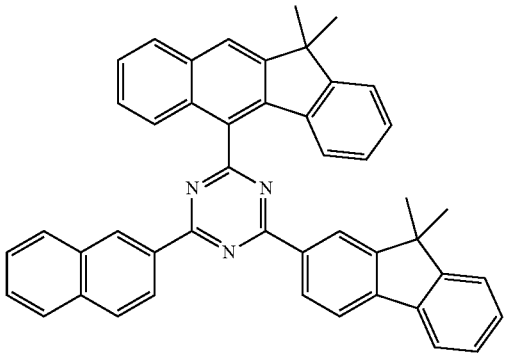

-continued
C-8
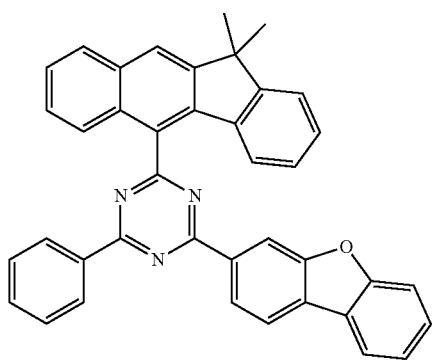
C-9
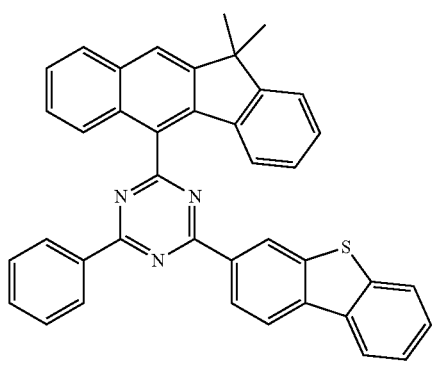
C-10
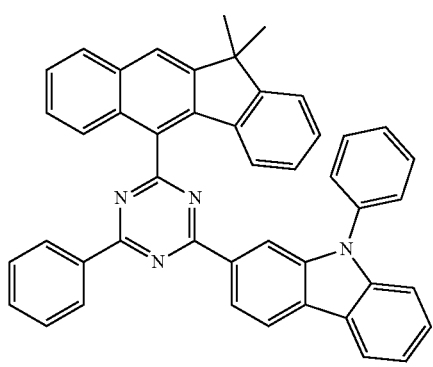
C-11
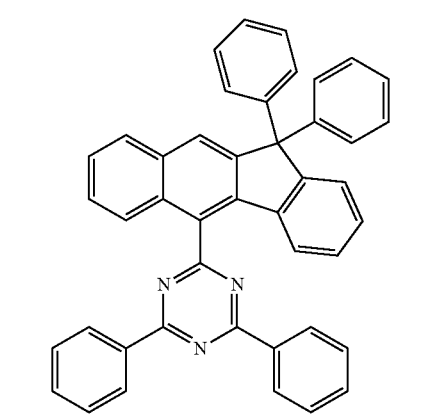
-continued
C-12
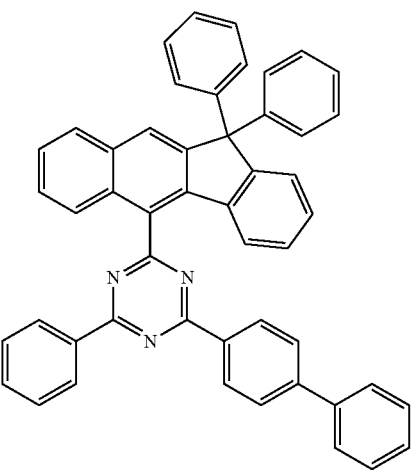
C-13
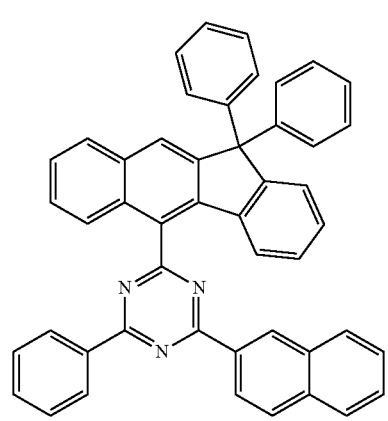
C-14
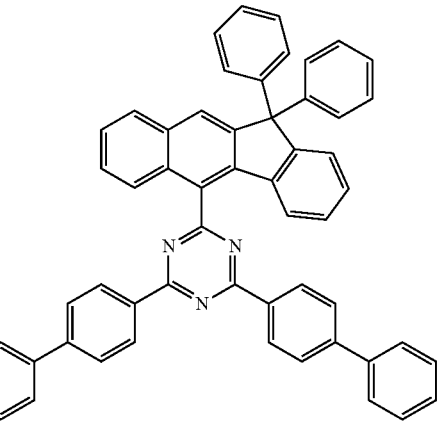

C-15
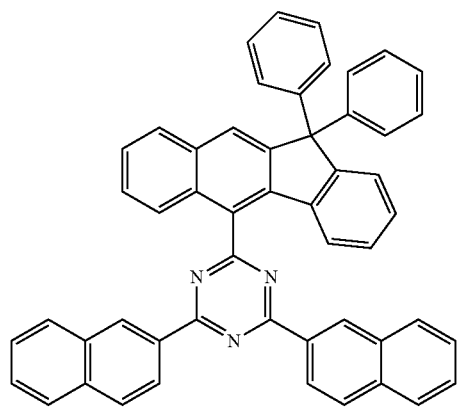
C-16
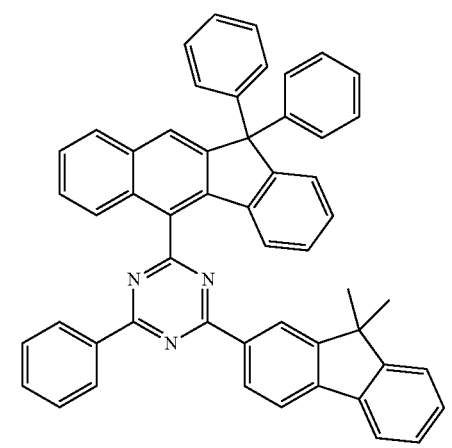
C-17
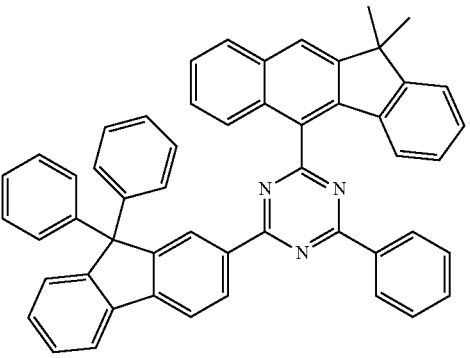
C-18
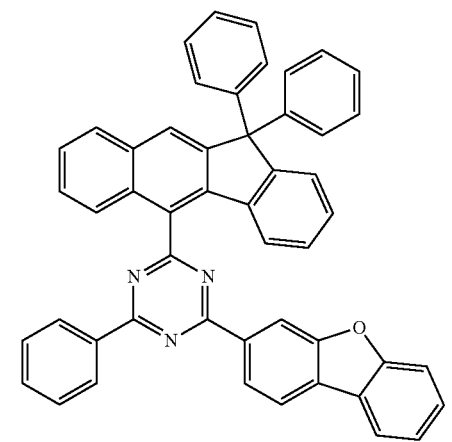
C-19
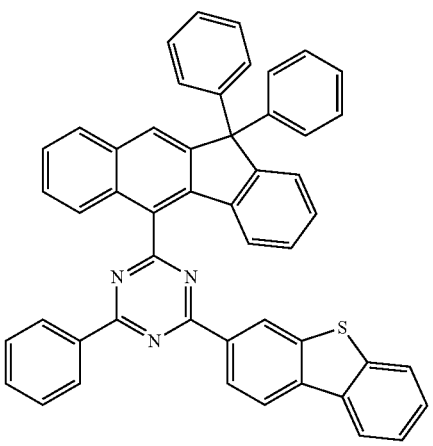
C-20
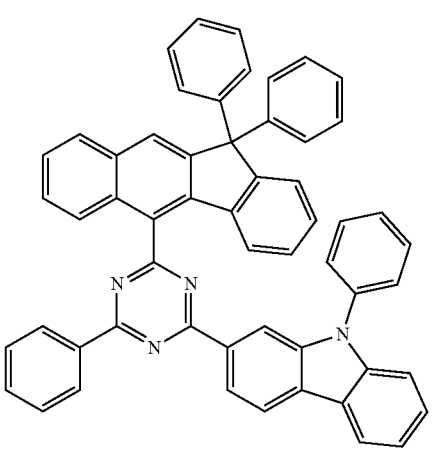
C-21
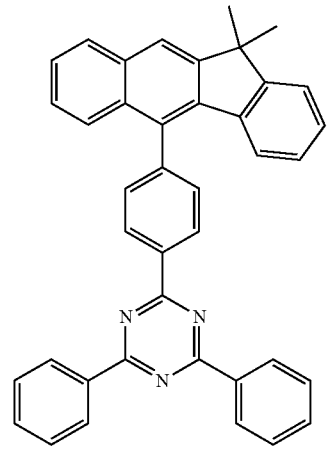

C-22
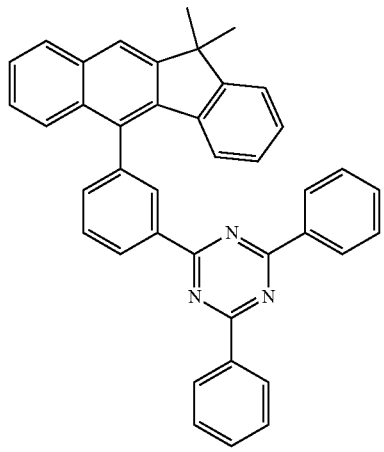
C-23
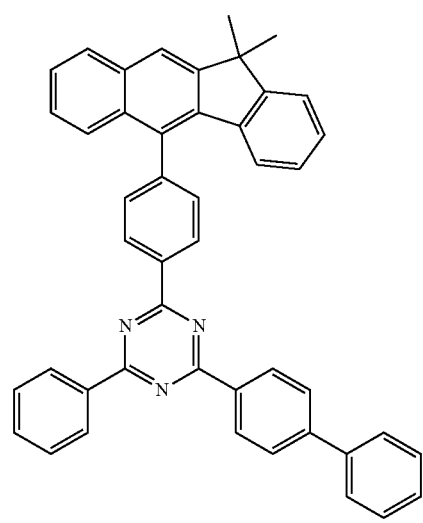
C-24
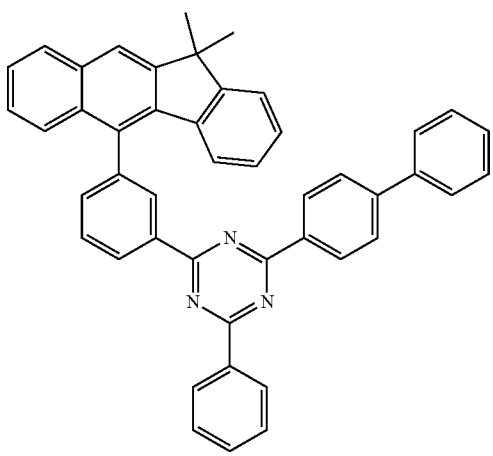
C-25
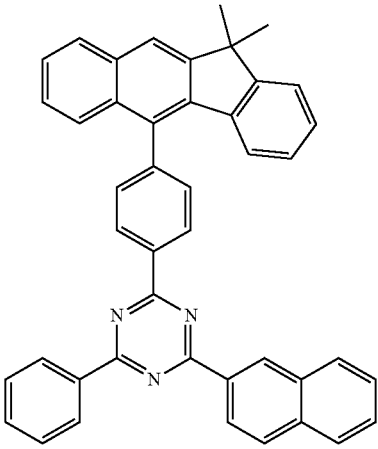
C-26
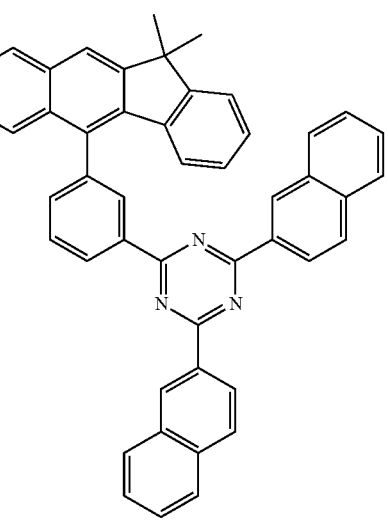
C-27
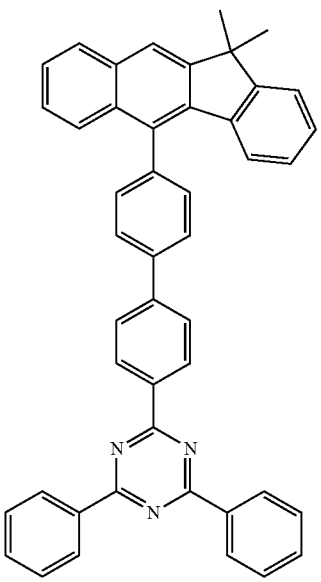

C-28
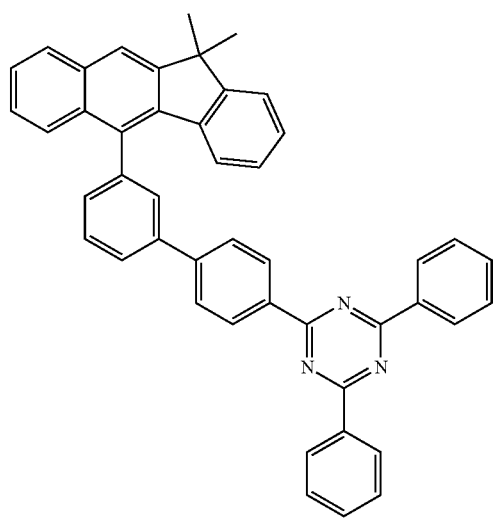
C-31
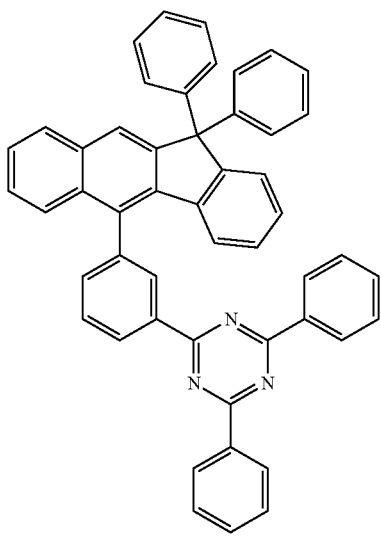
C-29
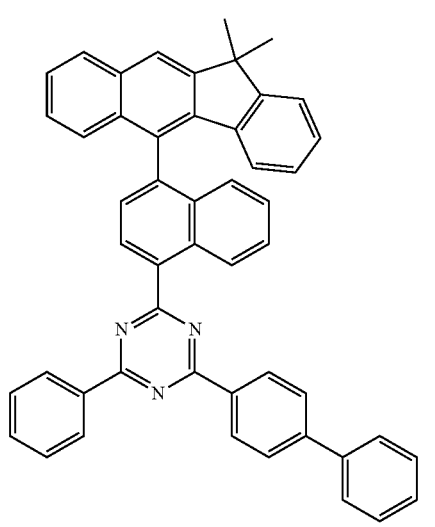
C-32
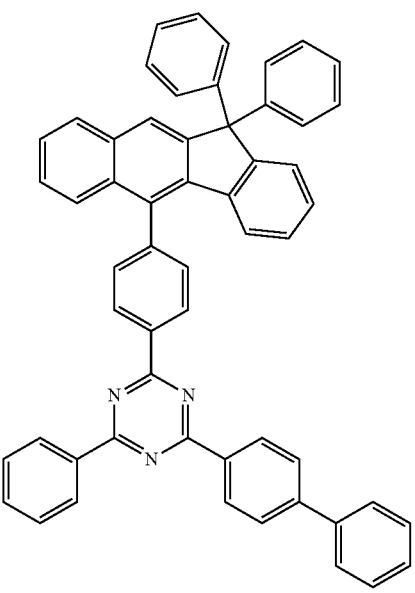
C-30
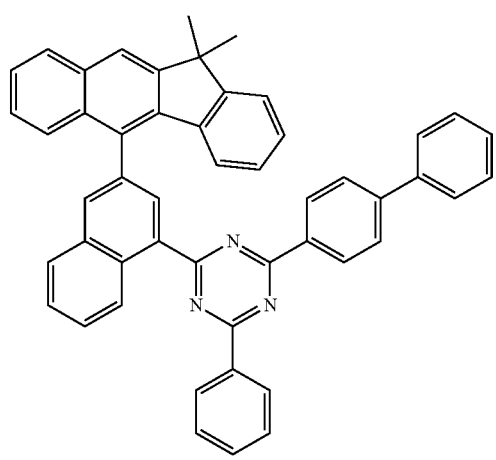
C-33
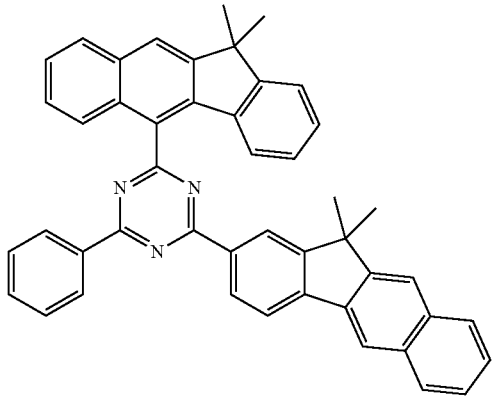

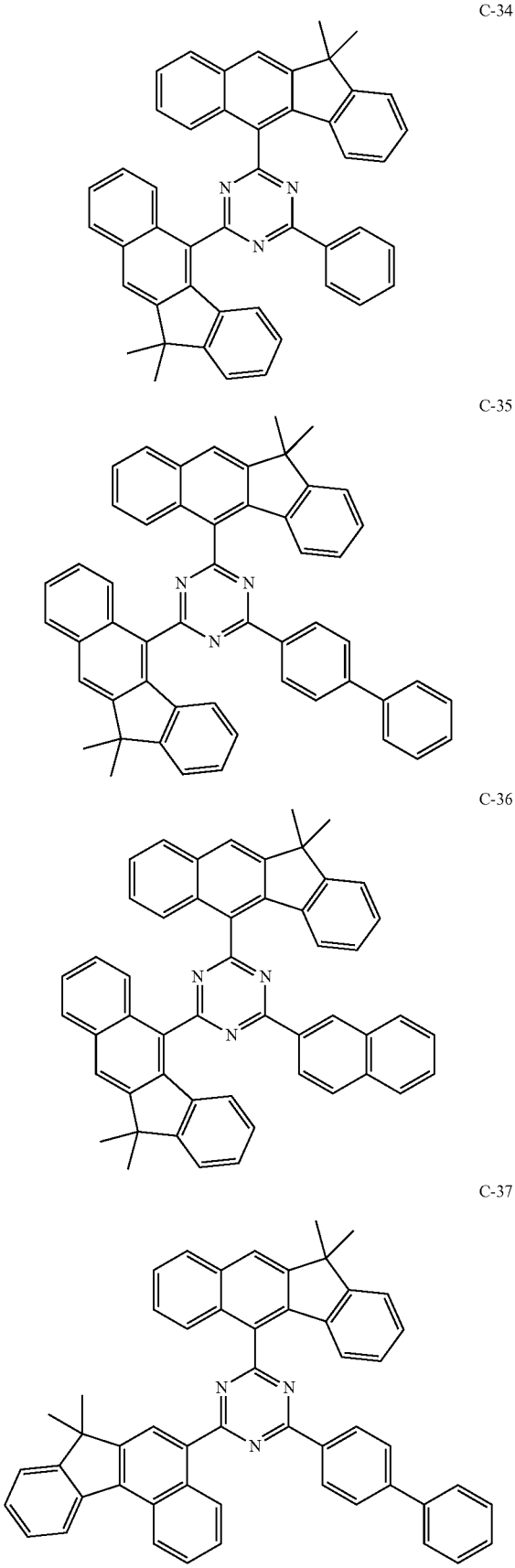
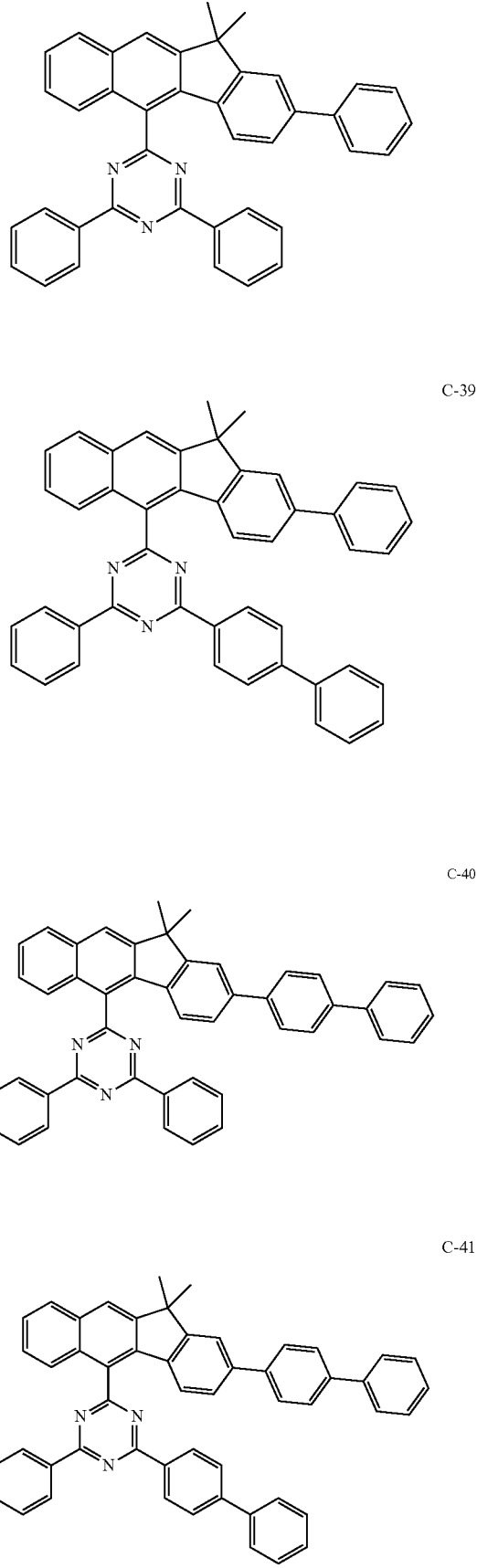

C-42
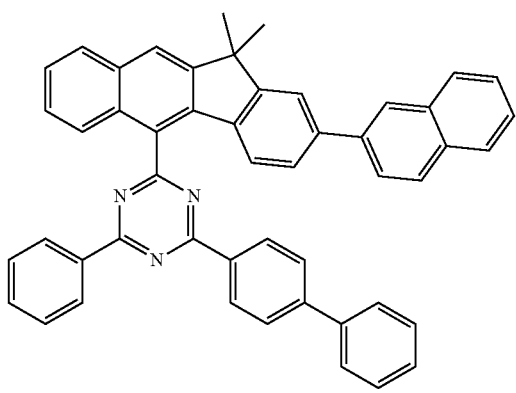
C-43
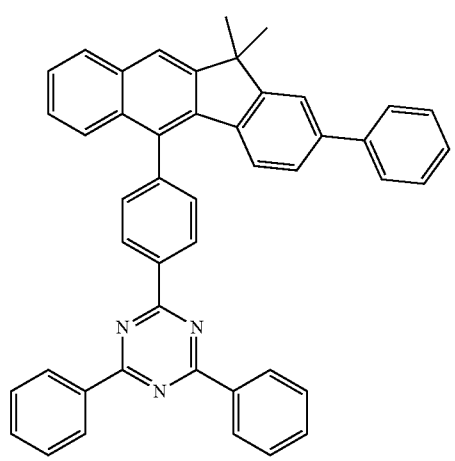
C-44
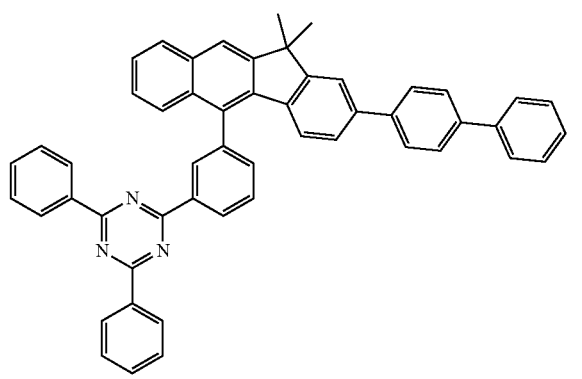
C-45
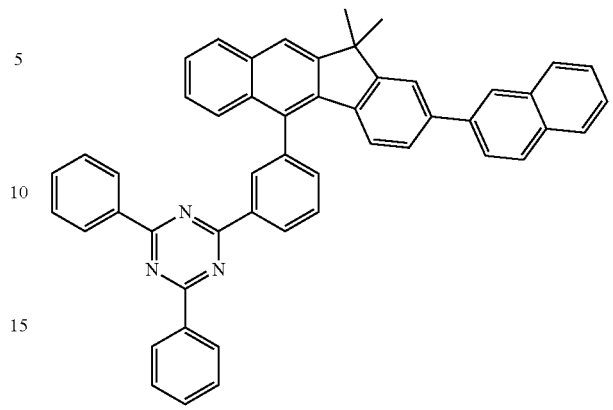
C-46
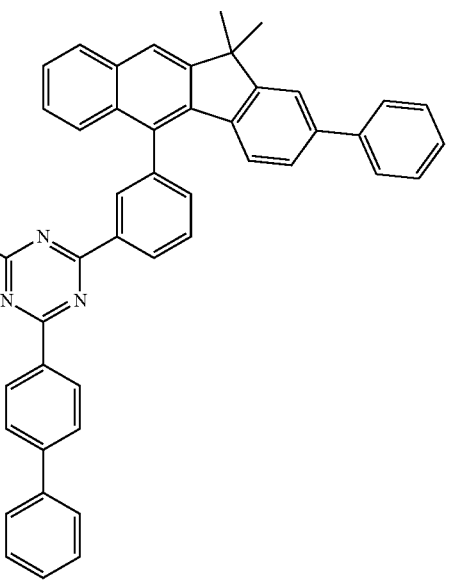
C-47
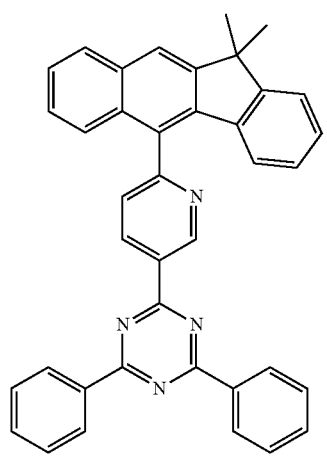

C-48
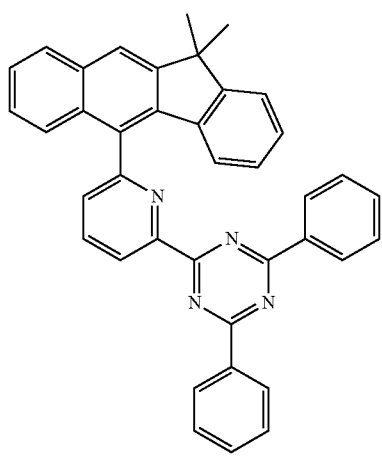
C-49
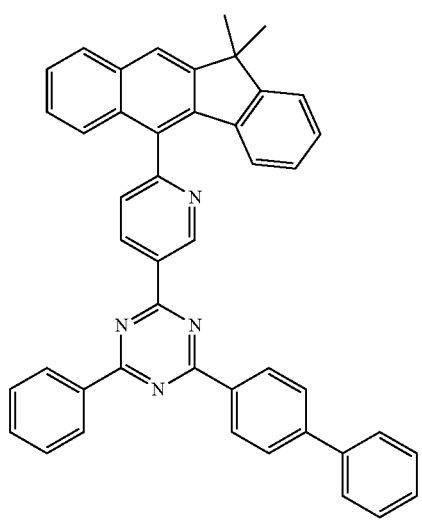
C-50
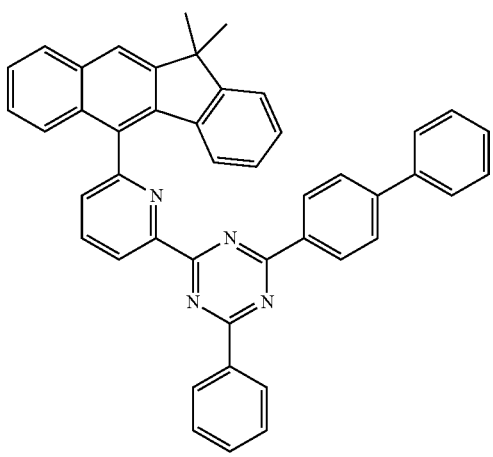
C-51
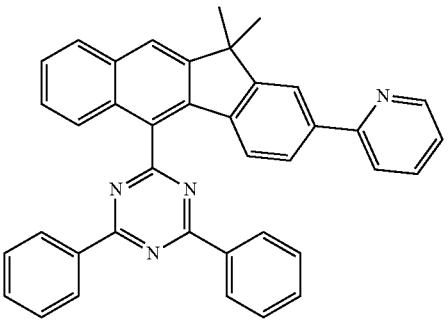
C-52
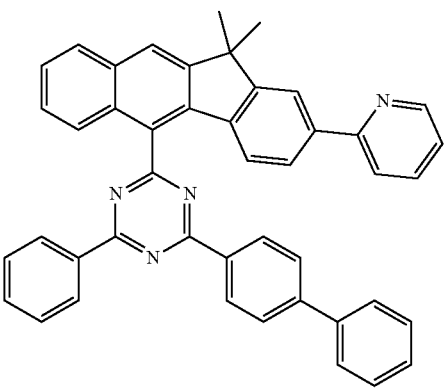
C-53
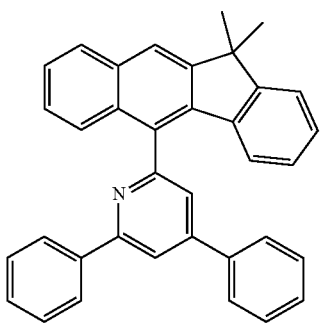
C-54
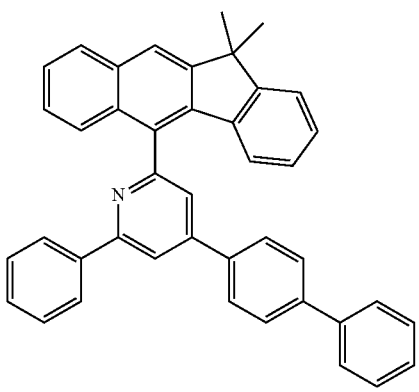

C-55
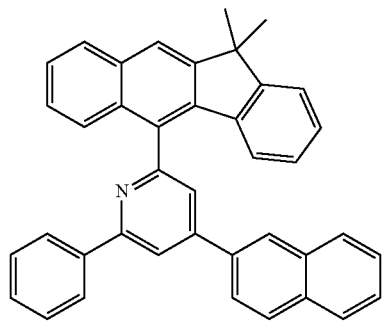
C-58
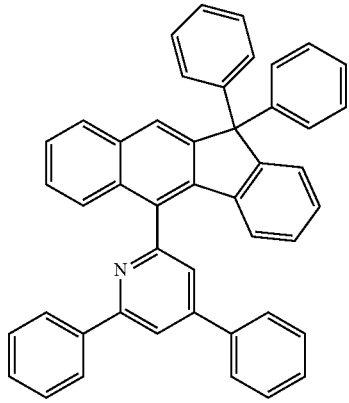
C-56
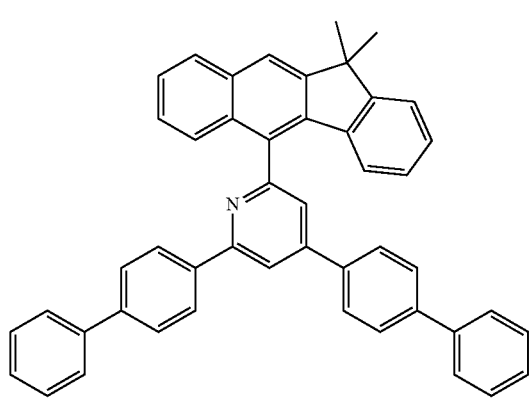
C-59
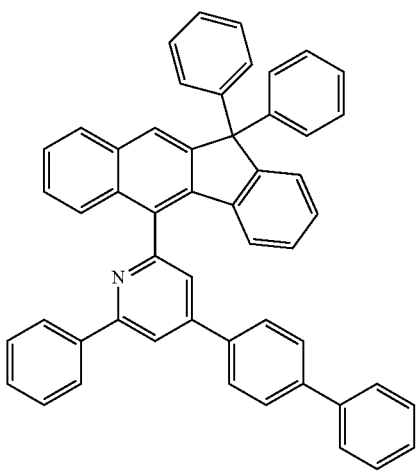
C-57
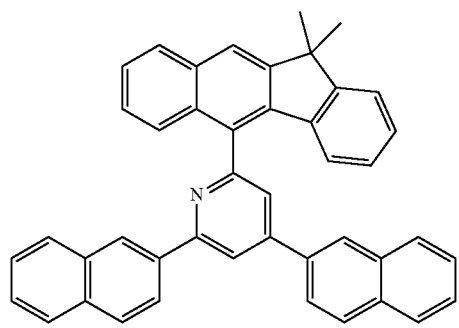
C-60
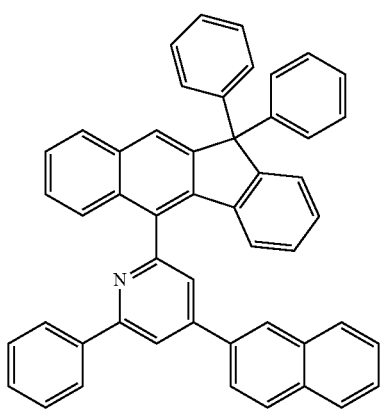

C-61
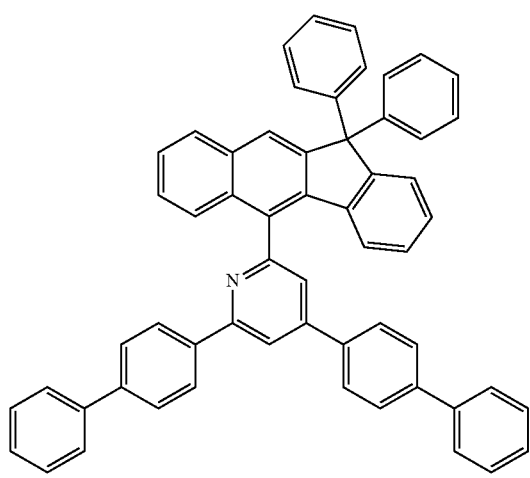
C-64
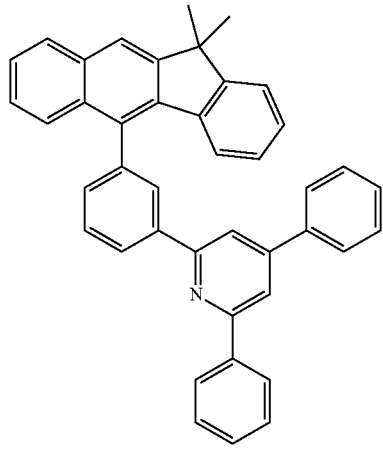
C-62
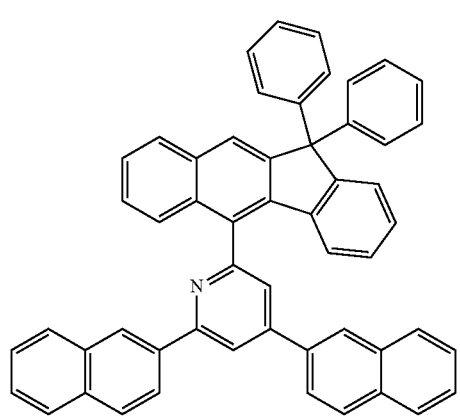
C-65
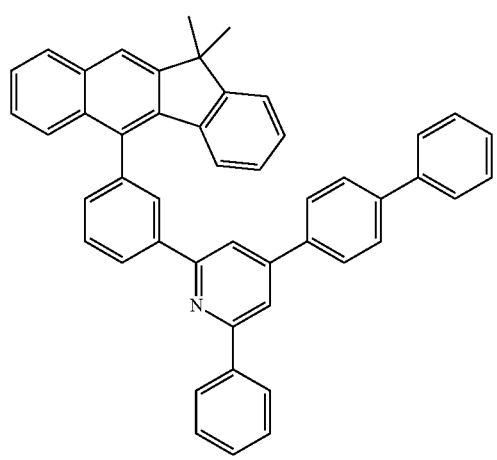
C-63
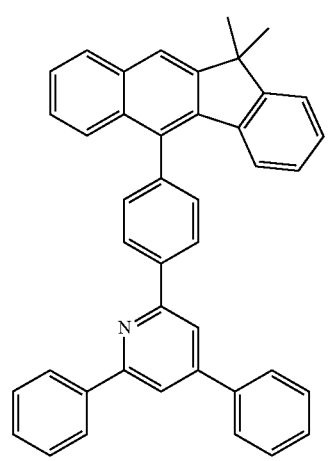
C-66
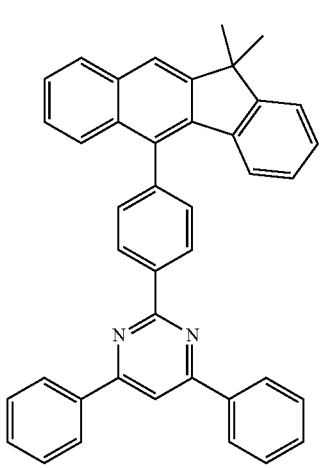

C-67
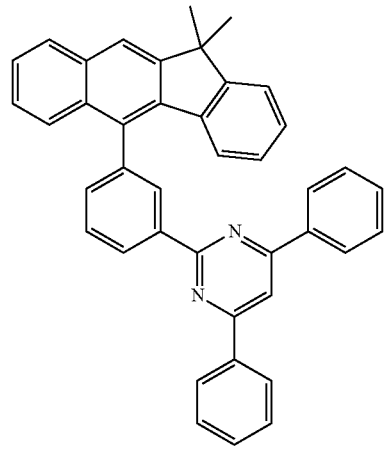
C-68
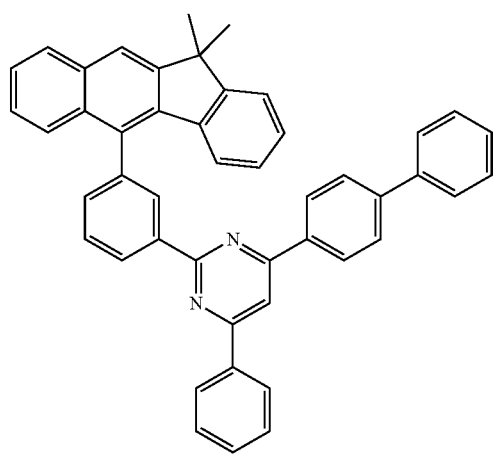
C-69
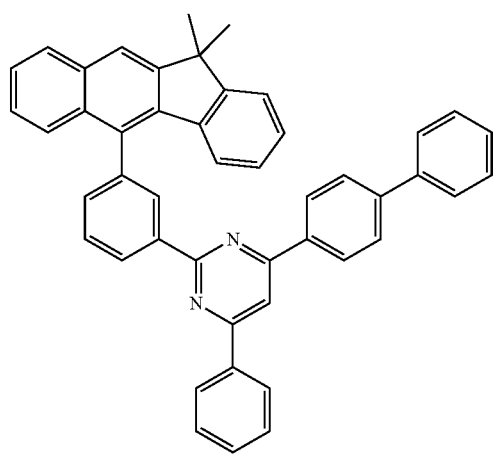
C-70
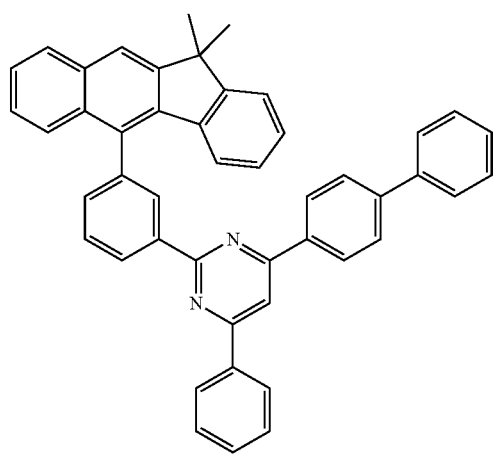
C-71
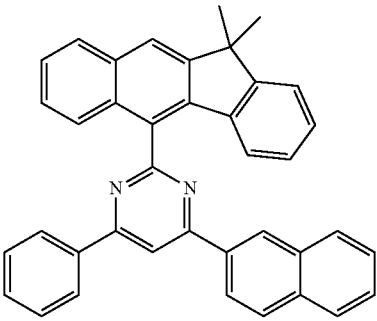
C-72
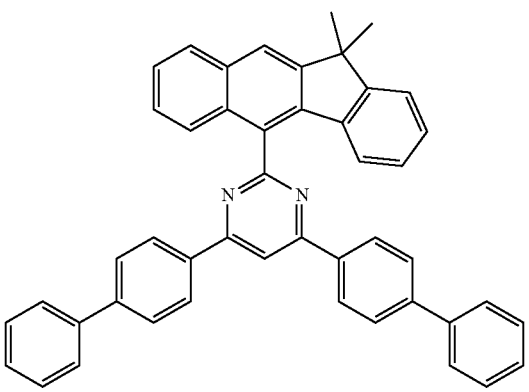
C-73
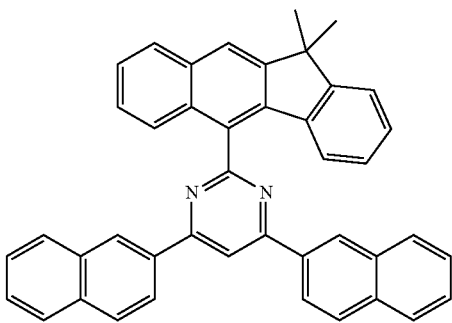
C-74
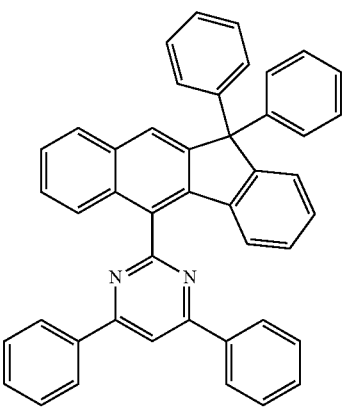

C-75
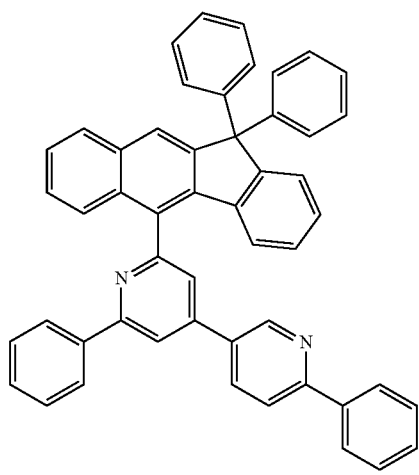
C-76
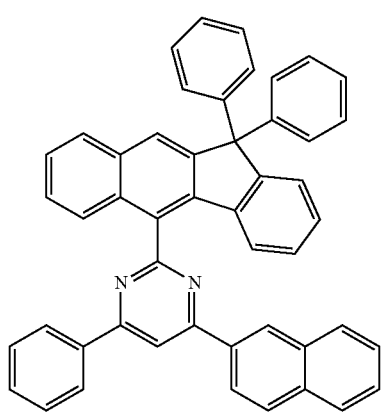
C-77
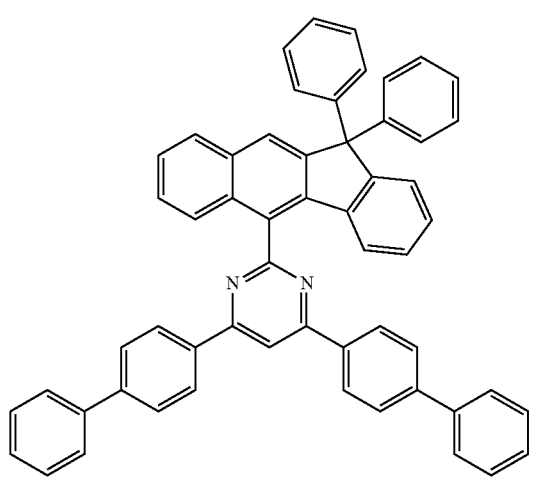
C-78
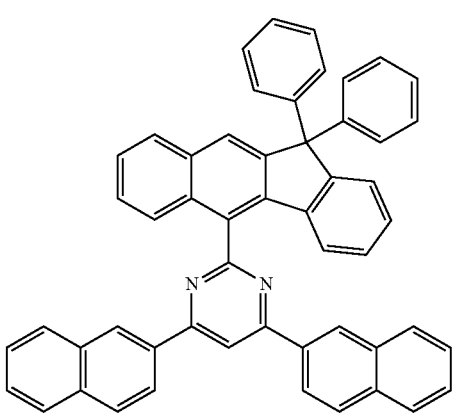
C-79
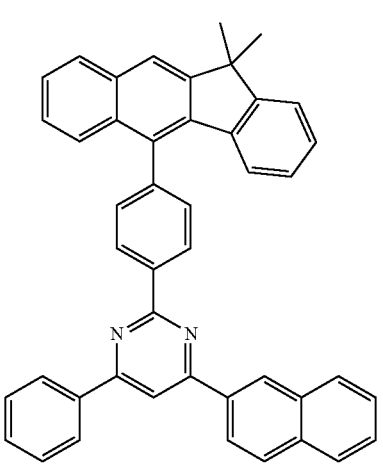
C-80
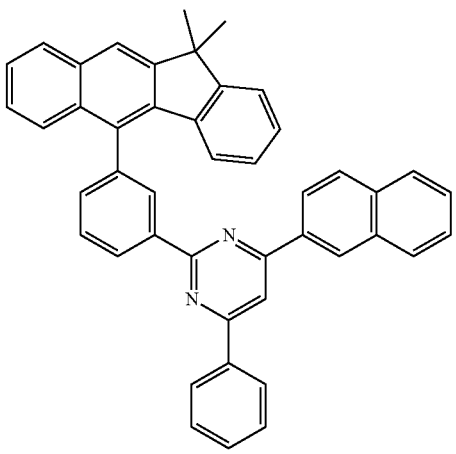

-continued
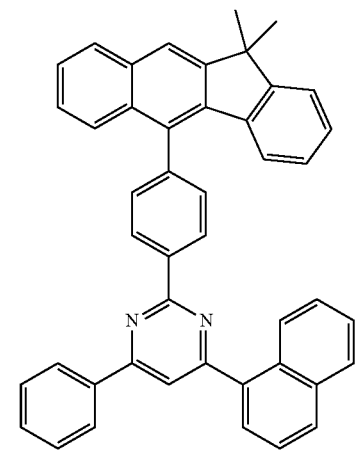
C-81
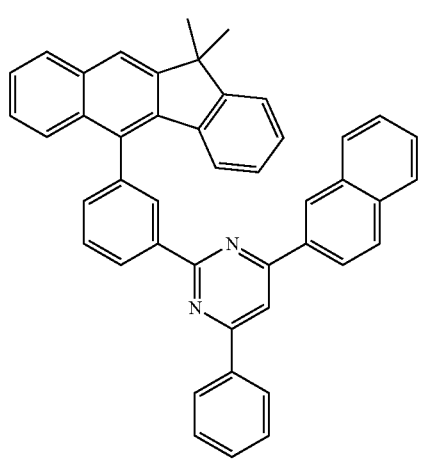
C-82
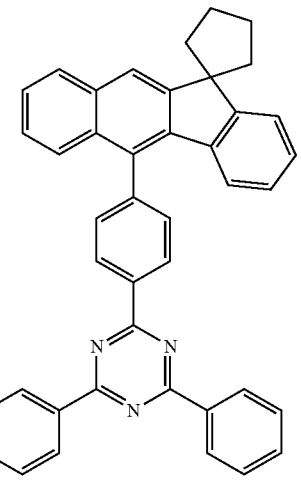
C-83
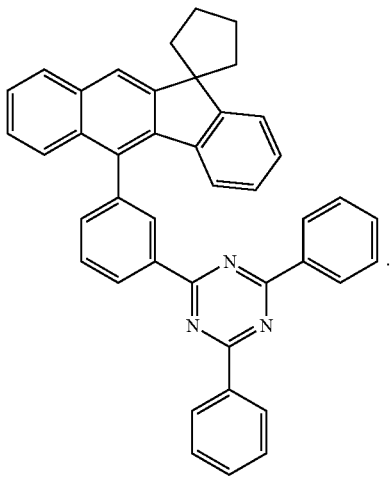
C-84
The compound of formula 1 according to the present disclosure can be prepared by a synthetic method known to a person skilled in the art. For example, it can be prepared according to the following reaction schemes.
[Reaction Scheme 1]
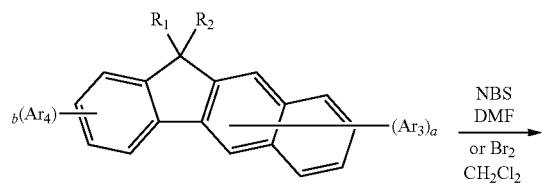
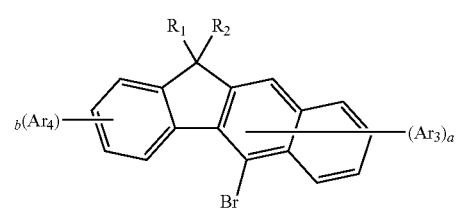
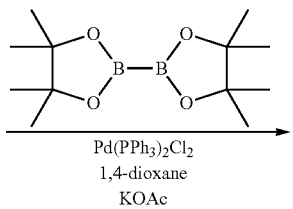

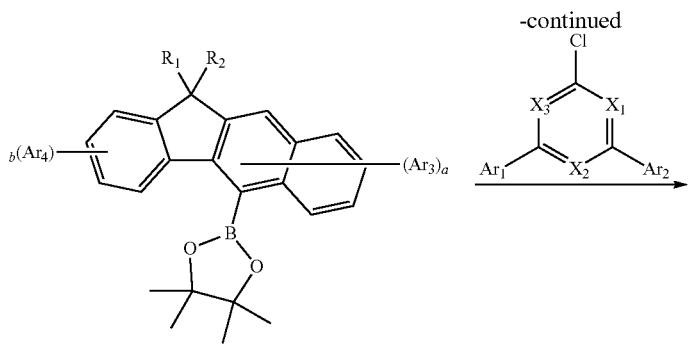

[Reaction Scheme 2]

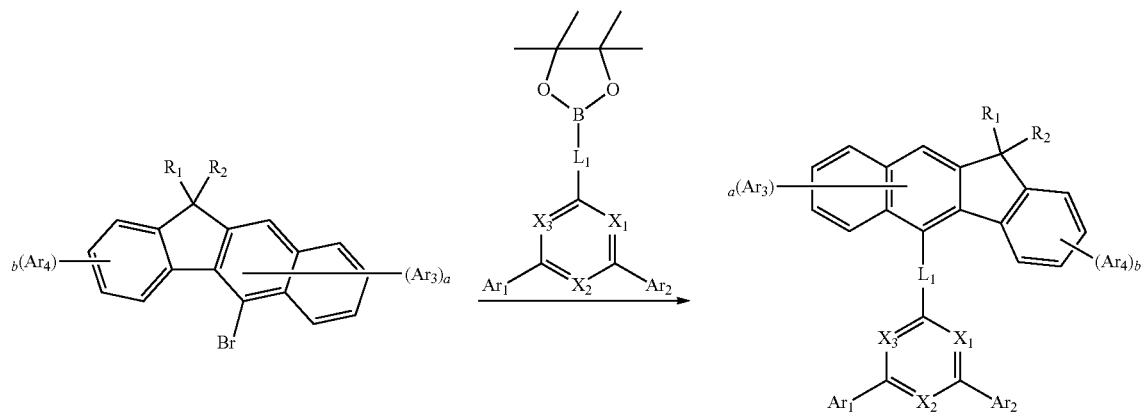

wherein $X_1$ to $X_3$, $Ar_1$ to $Ar_4$, $L_1$, $R_1$, $R_2$, a, and b are as defined in formula 1.

The present disclosure provides an organic electroluminescent material comprising the organic electroluminescent compound of formula 1, and an organic electroluminescent device comprising the material.

The above material can be comprised of the organic electroluminescent compound according to the present disclosure alone, or can further include conventional materials generally used in organic electroluminescent materials.

The organic electroluminescent device according to the present disclosure comprises a first electrode; a second electrode; and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The organic electroluminescent compound of formula 1 of the present disclosure may be comprised in one or more layers of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer; and preferably in one or more layers of the electron buffer layer and the electron transport layer. When used in the electron buffer layer, the organic electroluminescent compound of formula 1 of the present disclosure can be comprised as an electron buffer material. When used in the electron transport layer, the organic electroluminescent compound of formula 1 of the present disclosure can be comprised as an electron transport material.

The light-emitting layer can comprise one or more hosts and one or more dopants. If necessary, the light-emitting layer can comprise a co-host material, i.e., a plurality of host materials of two or more.

The host used in the present disclosure is at least one phosphorescent host compound or at least one fluorescent host compound, and these host compounds are not particularly limited. Specifically, the host compound may be a fluorescent host compound, for example, an anthracene compound represented by the following formula 11:

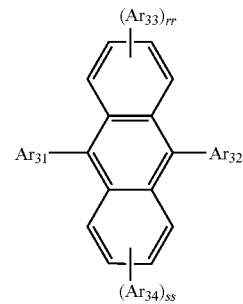

wherein
$Ar_{31}$ and $Ar_{32}$ each independently represent a substituted or unsubstituted (C6-C30)aryl, or a substituted or unsubstituted (5- to 30-membered)heteroaryl;

$Ar_{33}$ and $Ar_{34}$ each independently represent hydrogen, deuterium, a halogen, a cyano, a nitro, a hydroxyl, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted (C1-C30)alkylsilyl, a substituted or unsubstituted (C6-C30)arylsilyl, a substituted or unsubstituted (C6-C30)aryl(C1-C30)alkylsilyl, or NR$_{41}$R$_{42}$;

R$_{41}$ and R$_{42}$ independently represent hydrogen, a substituted or unsubstituted (C6-C30)aryl, or a substituted or unsubstituted (5- to 30-membered)heteroaryl; or may be linked to each other to form a mono- or polycyclic, (3- to 30-membered) alicyclic or aromatic ring, or the combination thereof, whose carbon atom(s) may be replaced with at least one heteroatom selected from nitrogen, oxygen, and sulfur; and rr and ss each independently represent an integer of 1 to 4, in which if rr or ss represents an integer of 2 or more, each Ar$_{33}$ or each Ar$_{34}$ may be the same or different.

The compound represented by formula 11 includes the following compounds, but is not limited thereto:

H-1
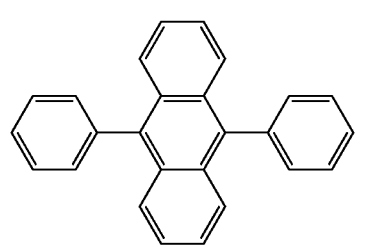

H-2
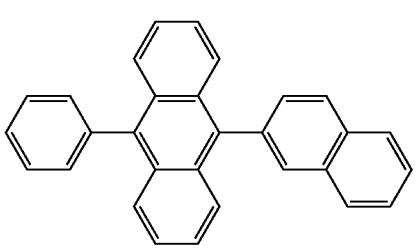

H-3
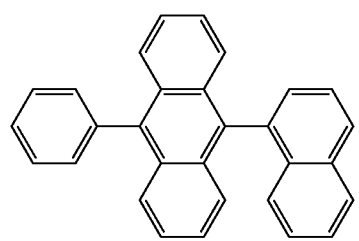

H-4
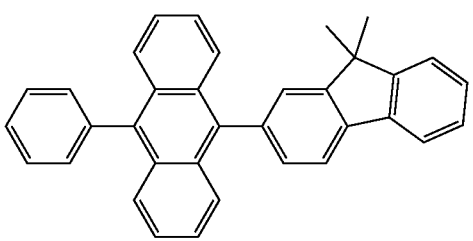

H-5
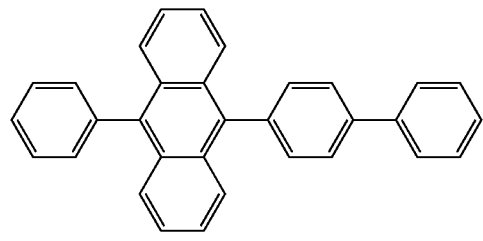

H-6
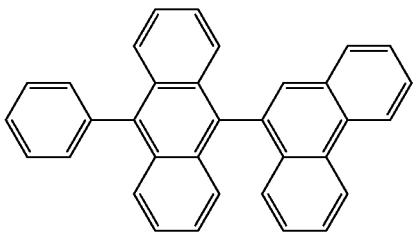

H-7
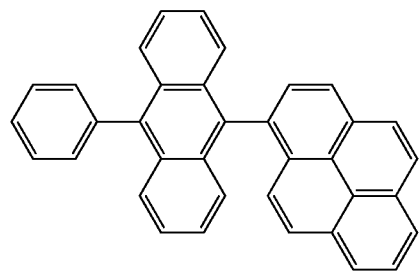

H-8
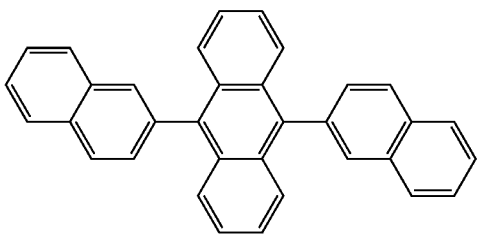

H-9
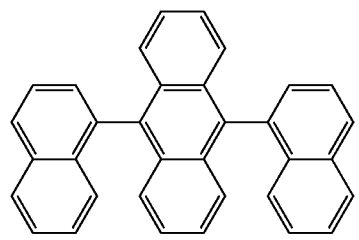

H-10
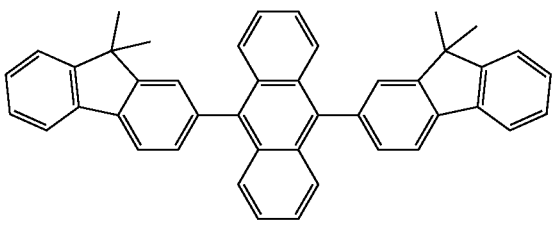

-continued
H-11
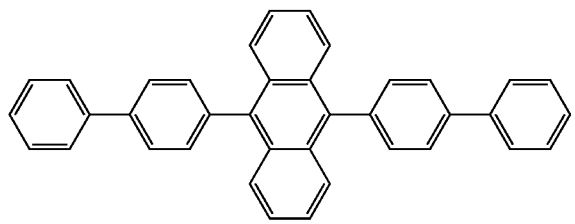
H-12
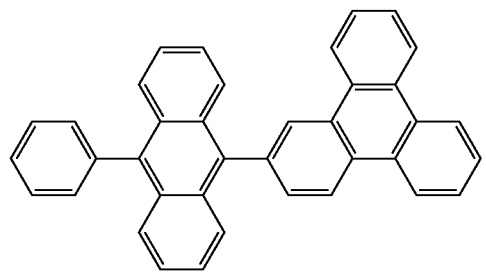
H-13
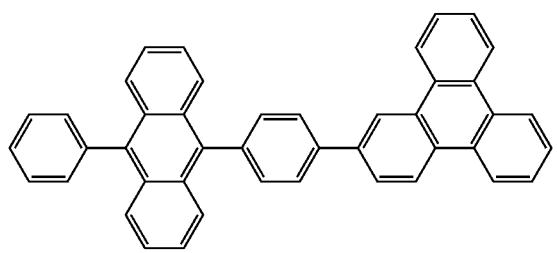
H-14
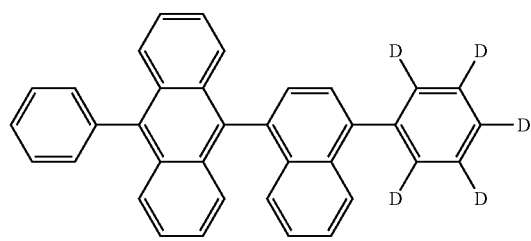
H-15
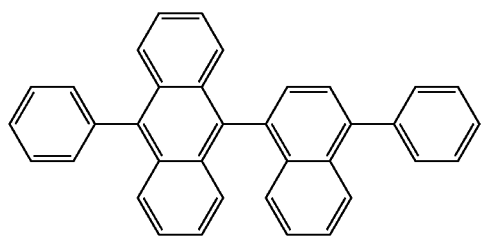
H-16
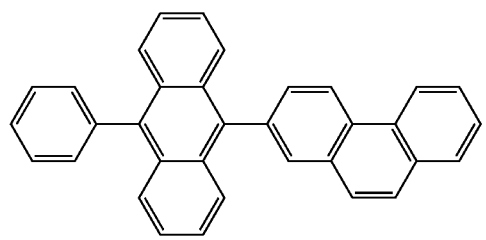
H-17
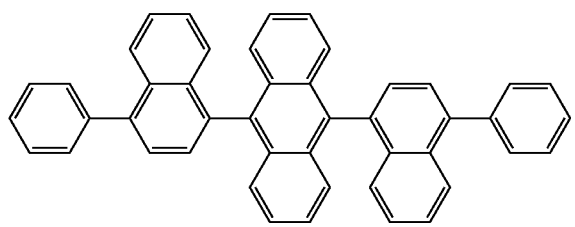
H-18
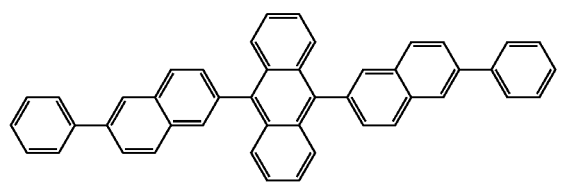
H-19
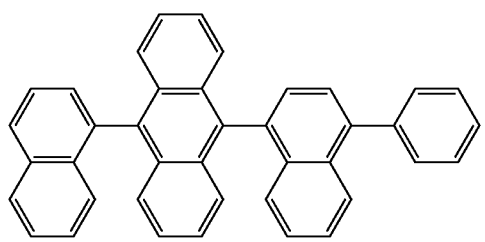
H-20
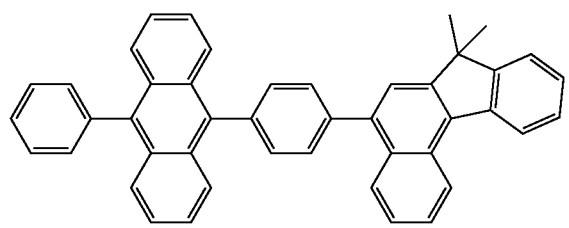
H-21
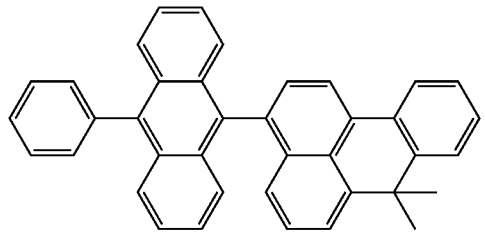
H-22
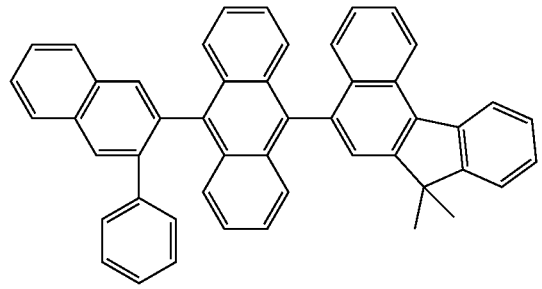

H-23
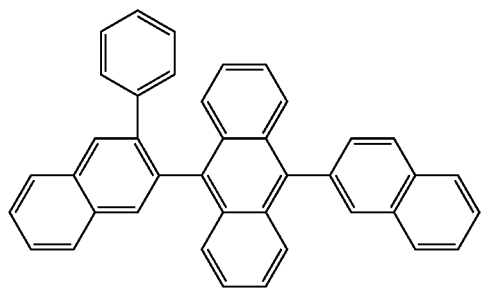
H-24
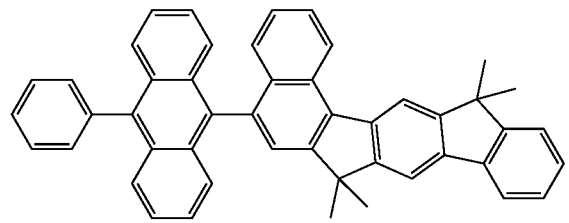
H-25
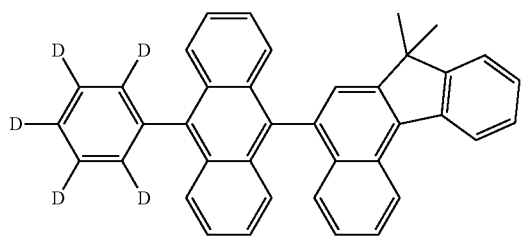
H-26
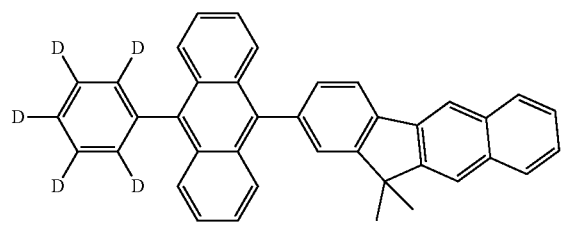
H-27
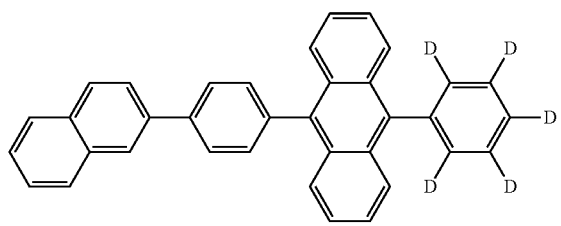
H-28
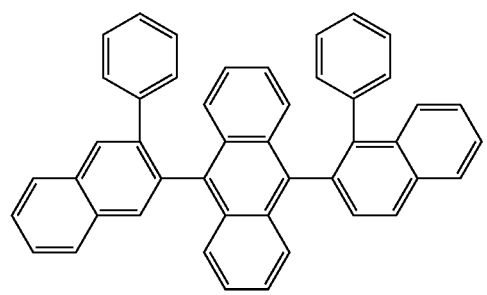
H-29
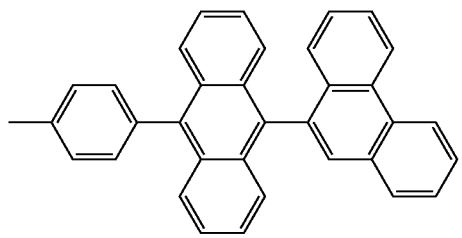
H-30
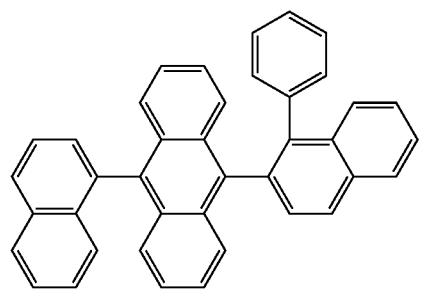
H-31
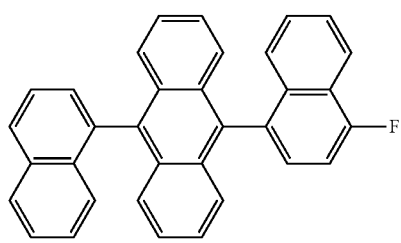
H-32
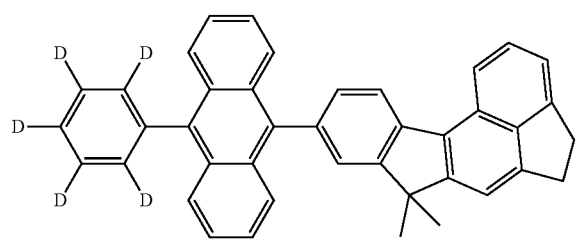

-continued
H-33
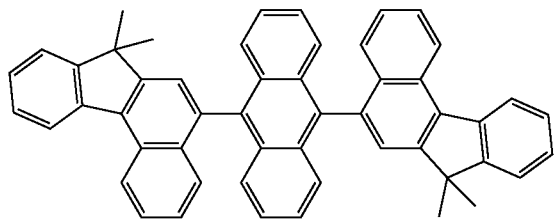
H-34
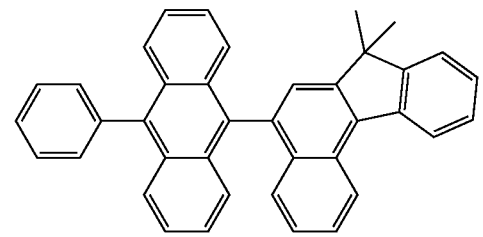
H-35
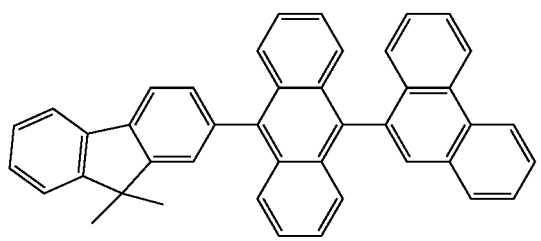
H-36
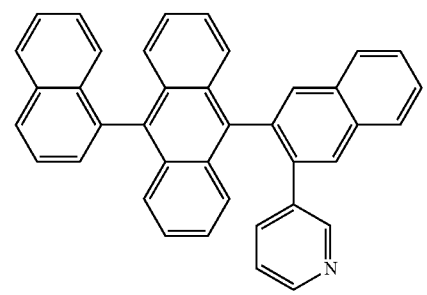
H-37
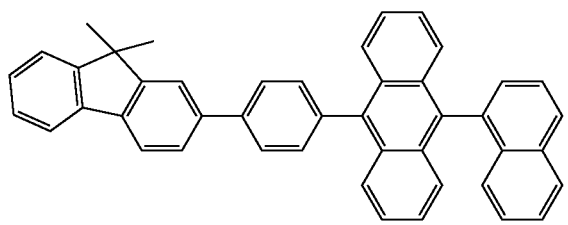
H-38
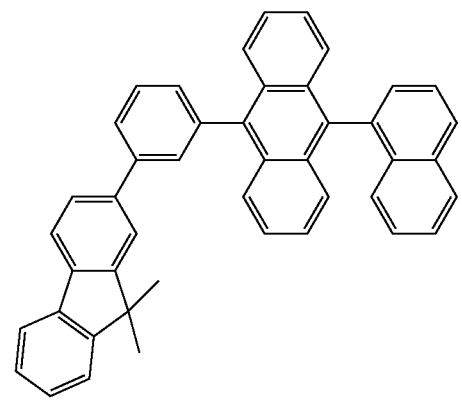
H-39
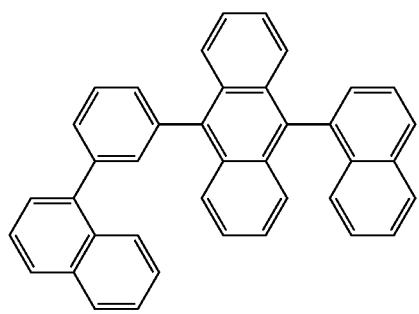
H-40
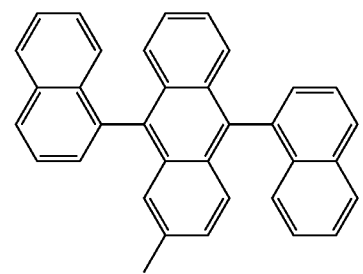

H-41
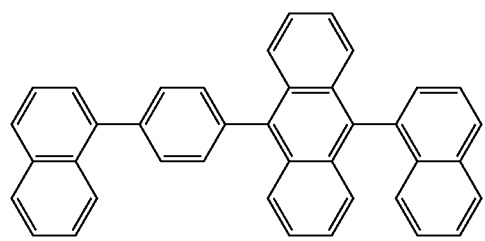
H-42
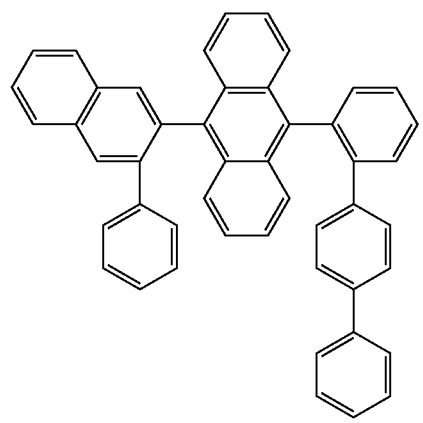
H-43
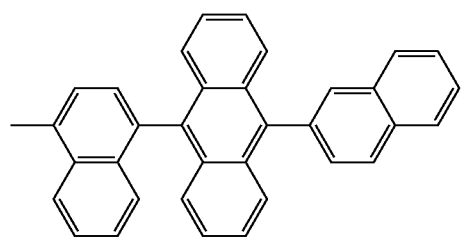
H-44
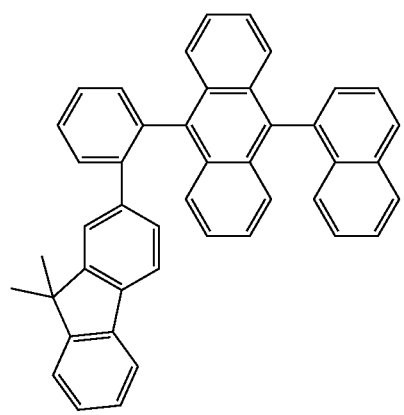
H-45
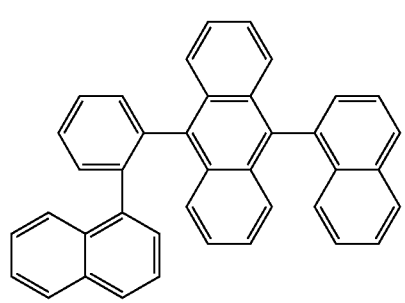
H-46
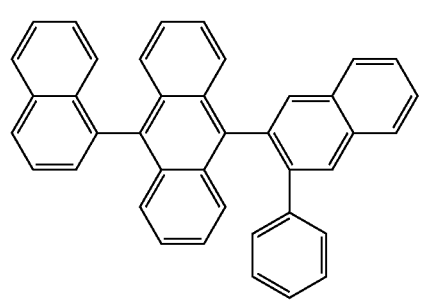
H-47
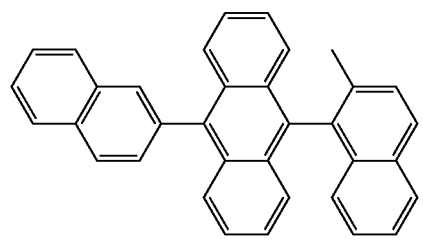
H-48
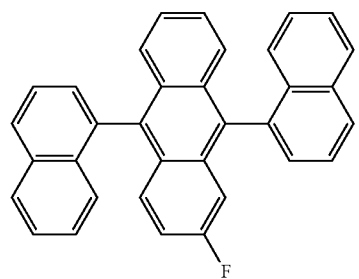

-continued
H-49
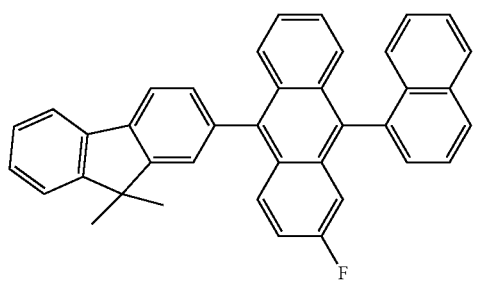
H-50
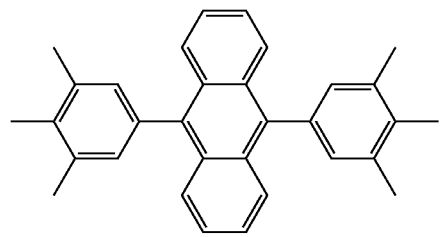
H-51
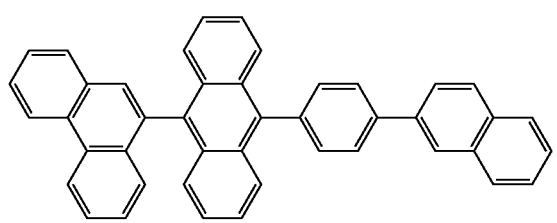
H-52
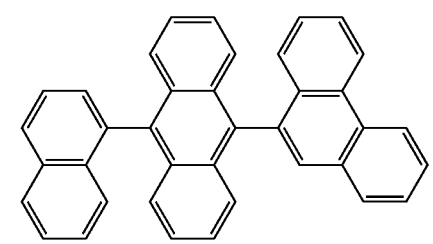
H-53
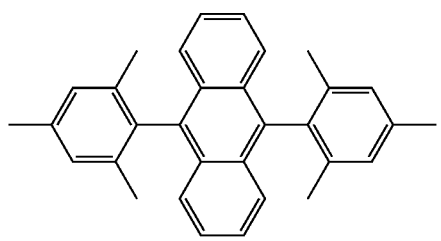
H-54
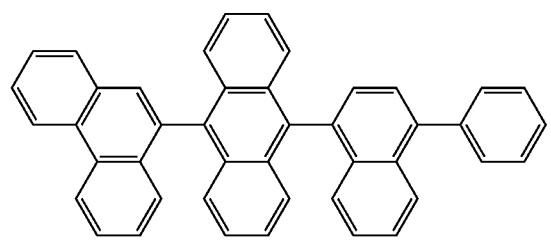
H-55
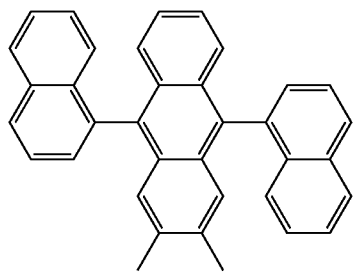
H-56
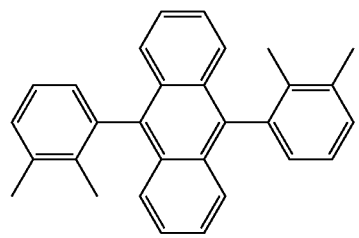
H-57
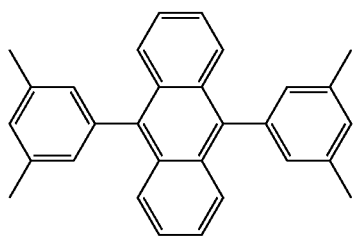
H-58
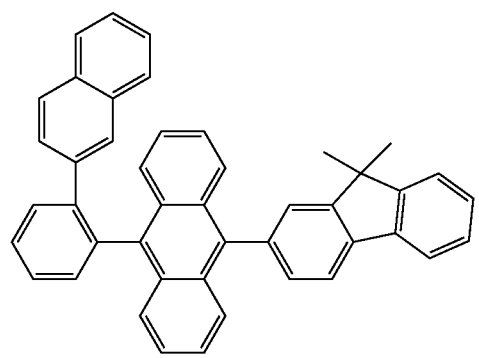

-continued
H-59
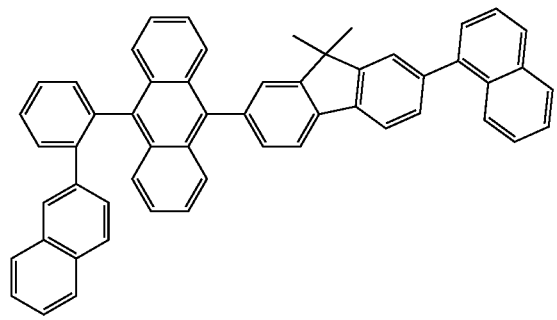
H-60
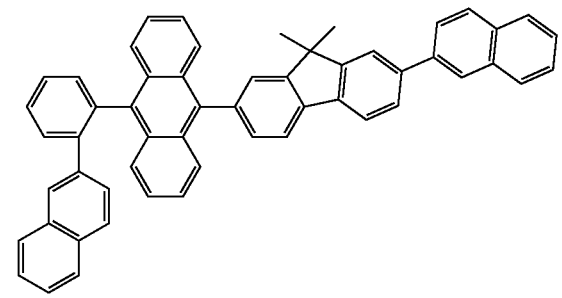
H-61
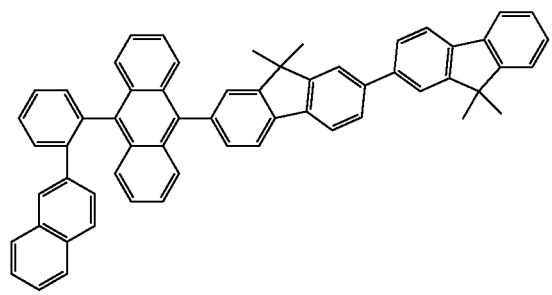
H-62
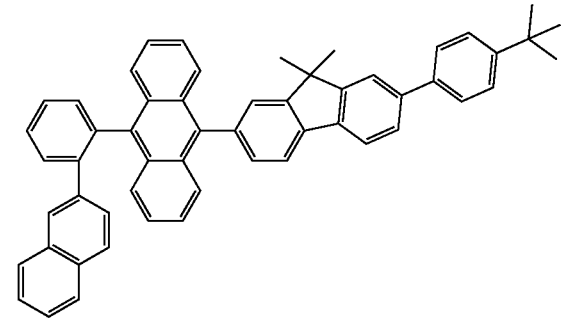
H-63
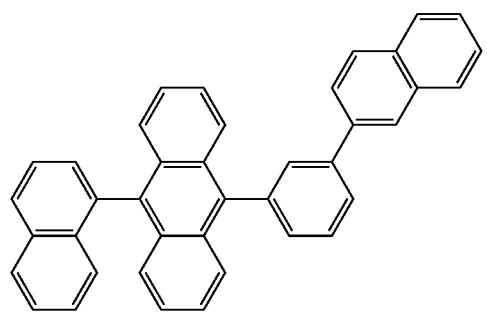
H-64
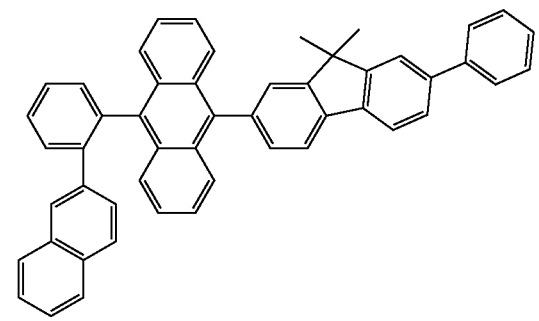
H-65
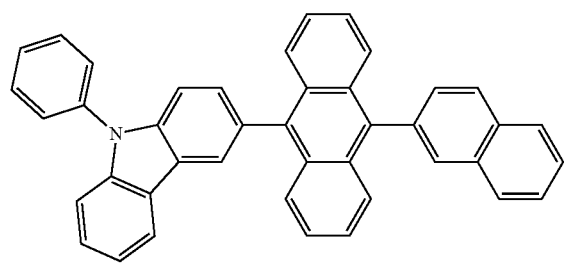
H-66
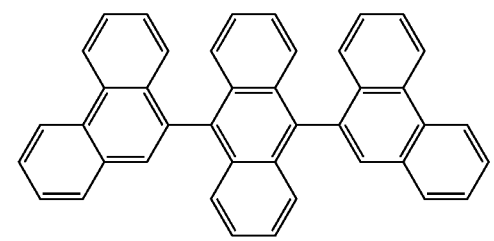
H-67
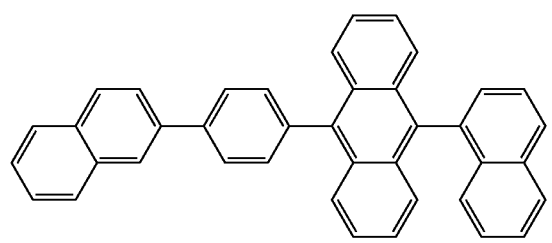
H-68
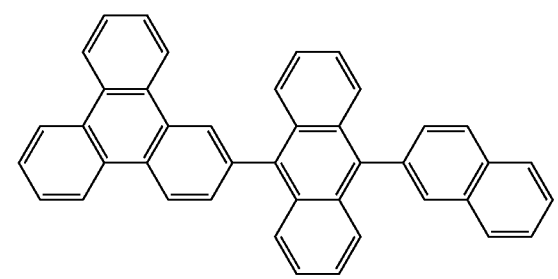

-continued
H-69
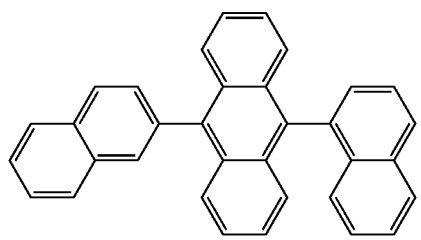
H-70
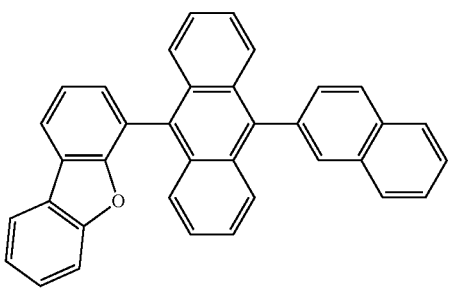
H-71
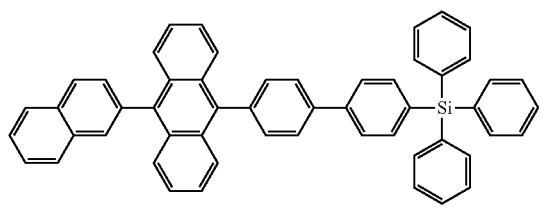
H-72
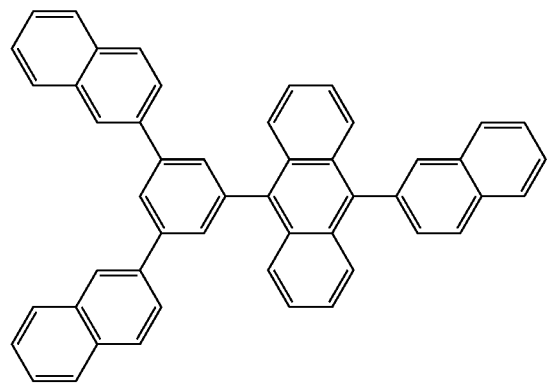
H-73
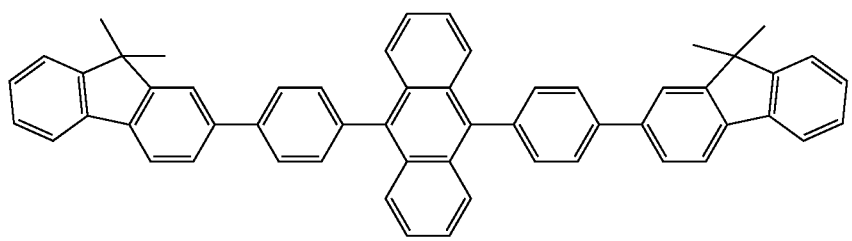
H-74
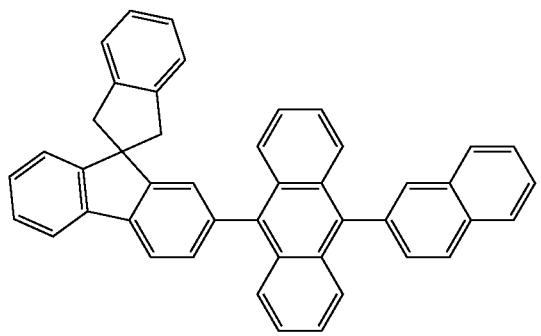
H-75
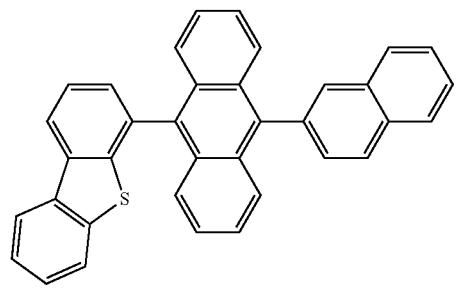
H-76
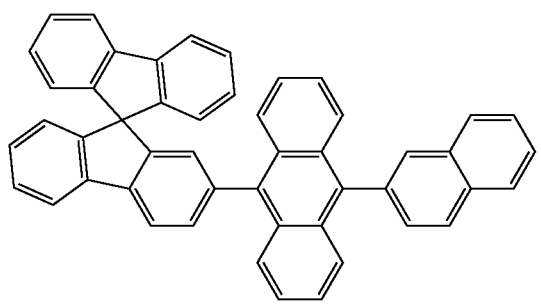
H-77
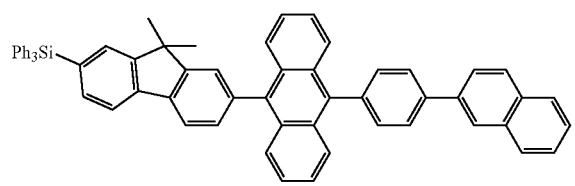

-continued
H-78
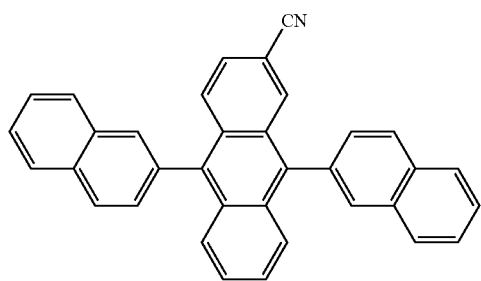
H-79
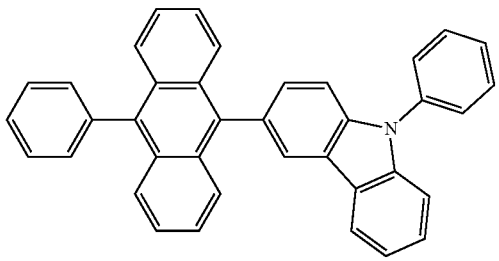
H-80
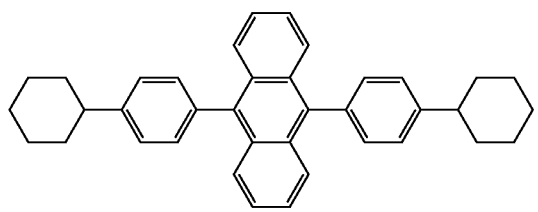
H-81
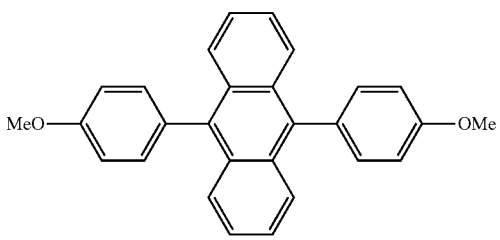
H-82
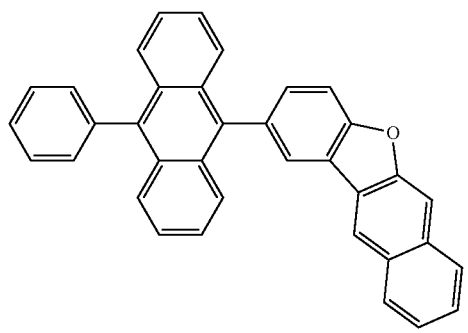
H-83
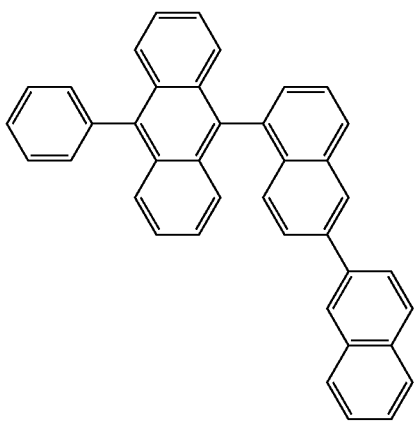
H-84
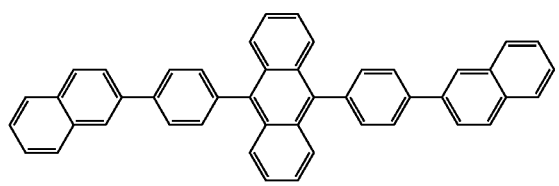
H-85
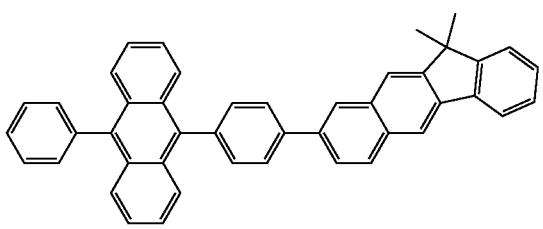
H-86
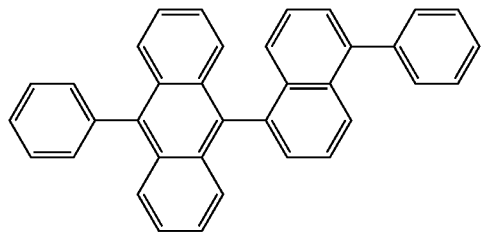
H-87
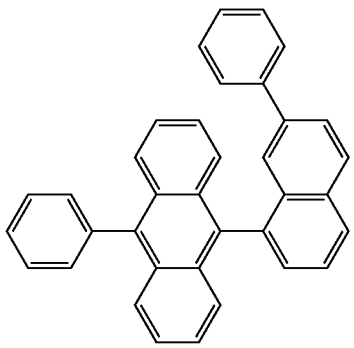

-continued
H-88
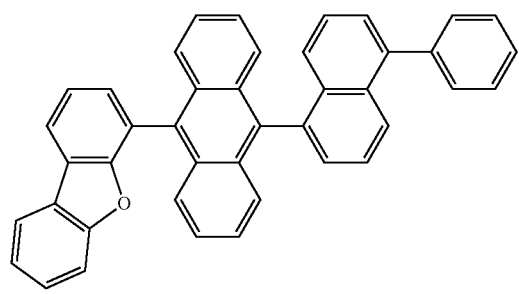
H-89
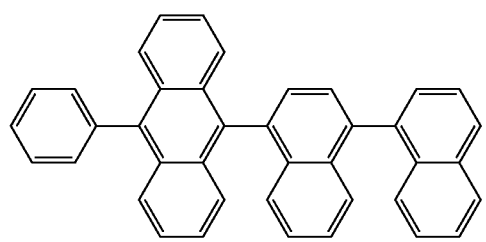
H-90
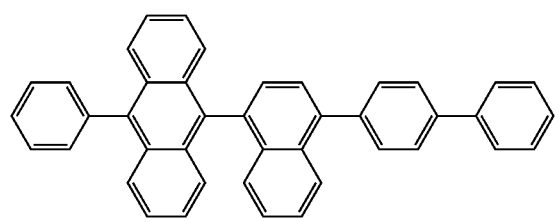
H-91
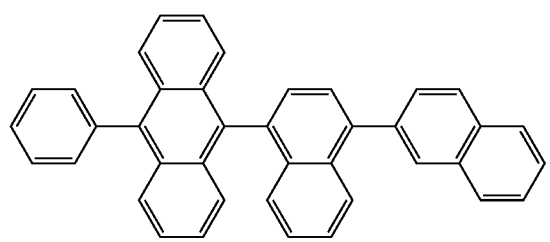
H-92
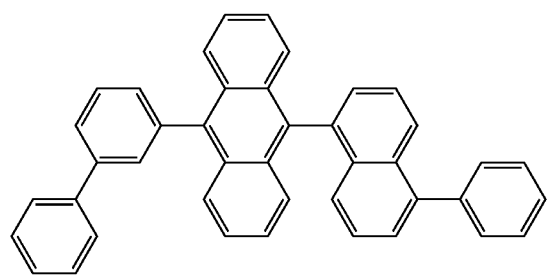
H-93
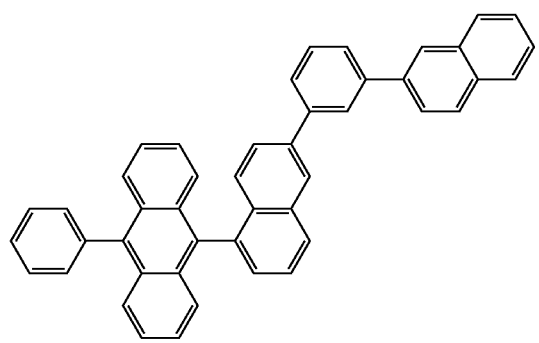
H-94
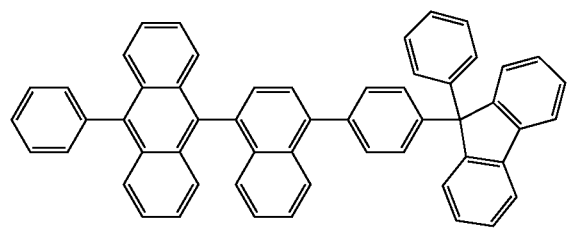
H-95
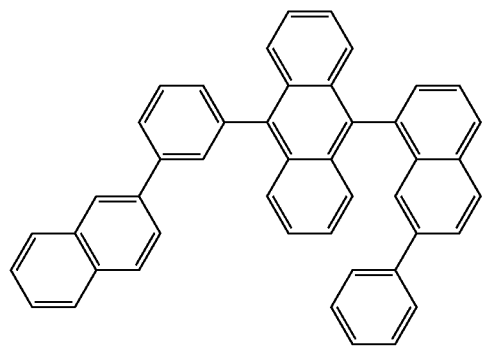

-continued
H-96
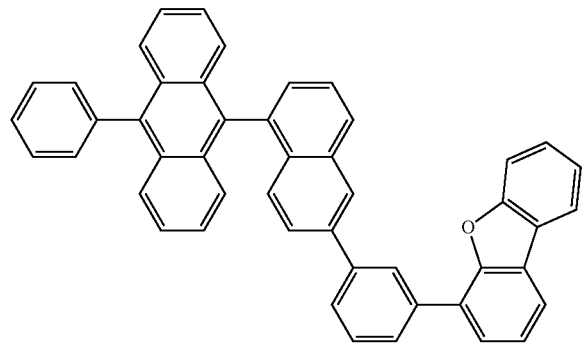
H-97
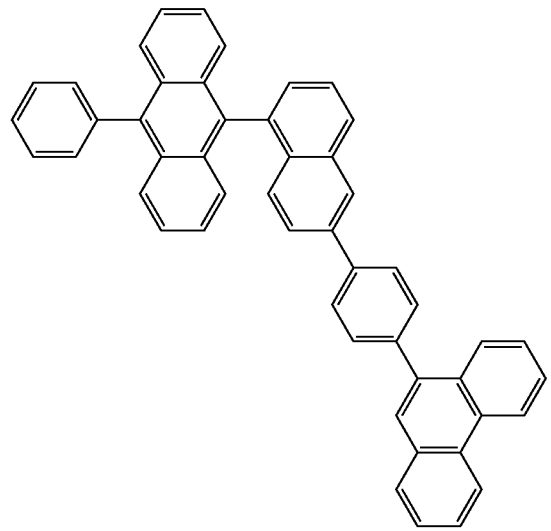
H-98
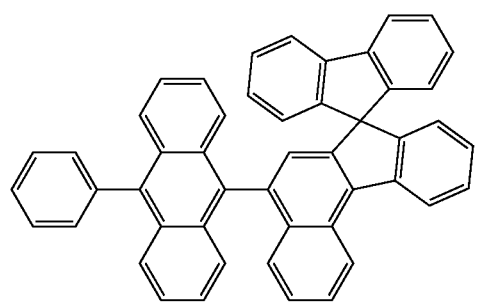
H-99
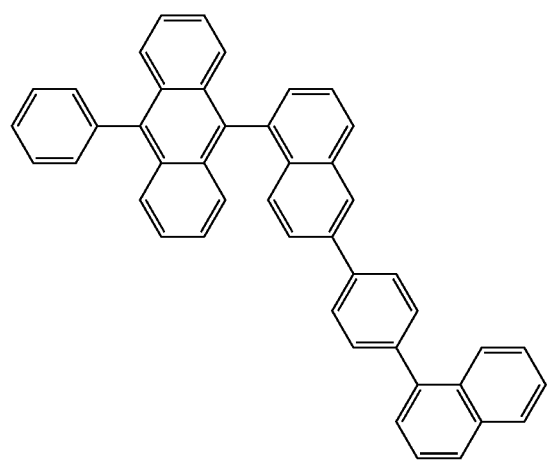
H-100
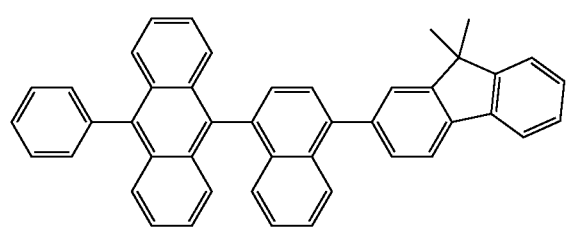
H-101
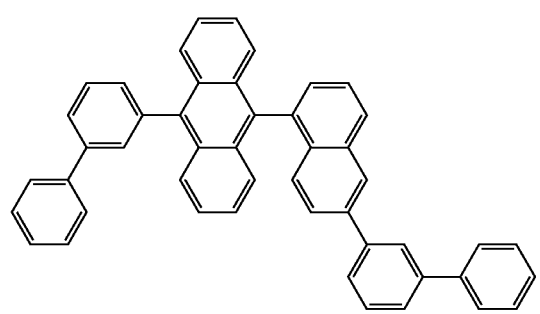

H-102

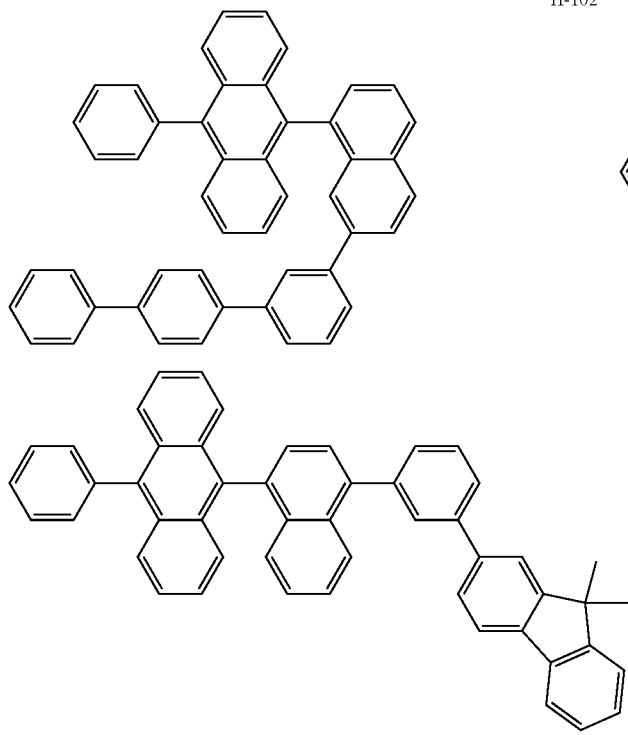

H-103

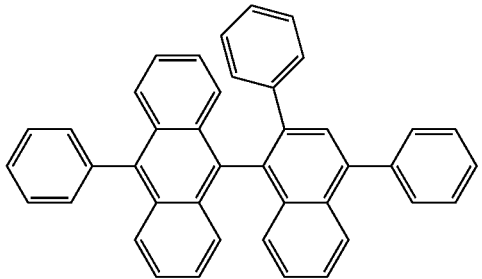

H-104

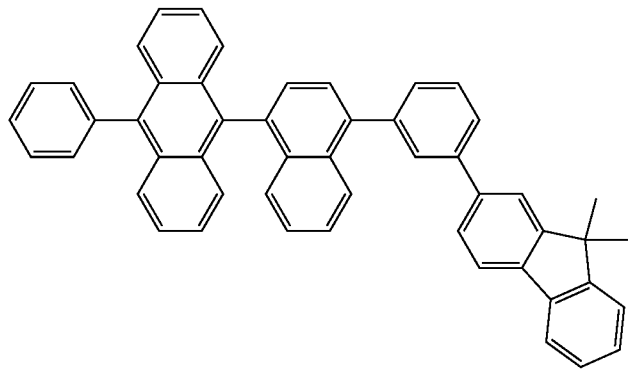

The dopant used in the present disclosure is at least one phosphorescent dopant compound or at least one fluorescent dopant compound. Specifically, the dopant compound may be a fluorescent dopant compound, for example, a condensed polycyclic amine derivative represented by the following formula 21:

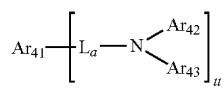

wherein $Ar_{41}$ represents a substituted or unsubstituted (C6-C50) aryl, or styryl;

$L_a$ represents a single bond, a substituted or unsubstituted (C6-C30)arylene, or a substituted or unsubstituted (3- to 30-membered)heteroarylene;

$Ar_{42}$ and $Ar_{43}$ each independently represent hydrogen, deuterium, a halogen, a substituted or unsubstituted (C1-C30)alkyl, a substituted or unsubstituted (C6-C30)aryl, or a substituted or unsubstituted (3- to 30-membered)heteroaryl; or may be linked to an adjacent substituent to form a mono- or polycyclic, (3- to 30-membered) alicyclic or aromatic ring, or the combination thereof, whose carbon atom(s) may be replaced with at least one heteroatom selected from nitrogen, oxygen, and sulfur; and

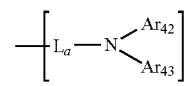

Preferably, the aryl group in $Ar_{41}$ includes a substituted or unsubstituted phenyl, a substituted or unsubstituted fluorenyl group, a substituted or unsubstituted anthryl group, a substituted or unsubstituted pyrenyl group, a substituted or unsubstituted chrysenyl group, a substituted or unsubstituted benzofluorenyl group, spiro[fluorene-benzofluorene], etc.

The compound represented by formula 21 includes the following compounds, but is not limited thereto:

D-1

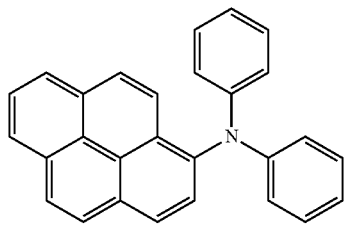

D-2

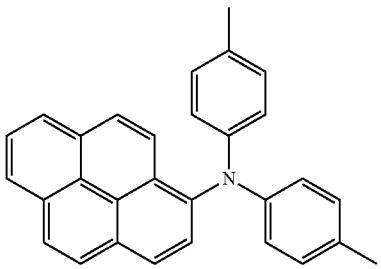

-continued
D-3
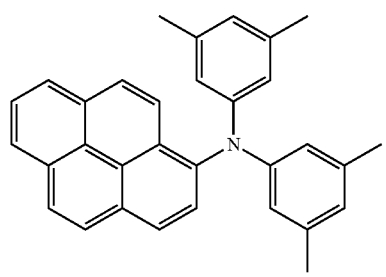
D-4
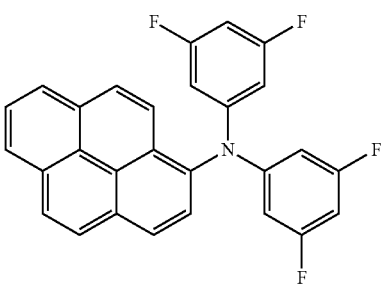
D-5
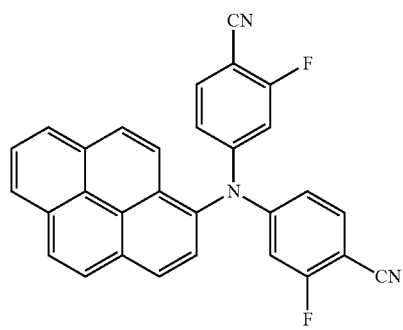
D-6
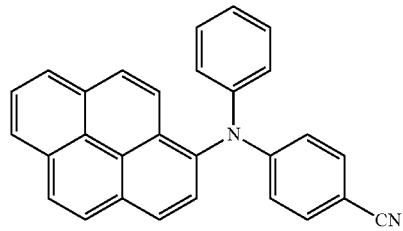
D-7
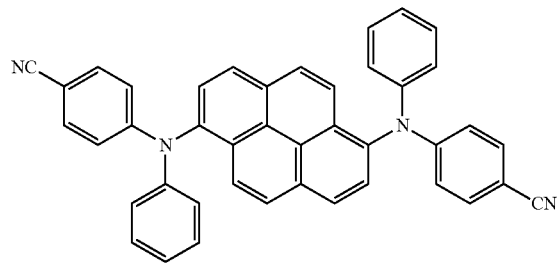
D-8
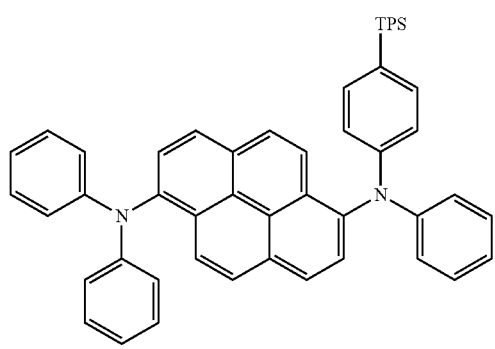
D-9
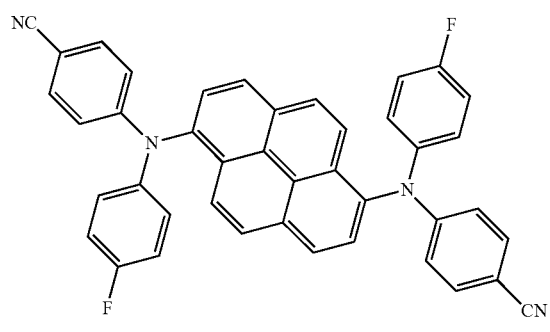
D-10
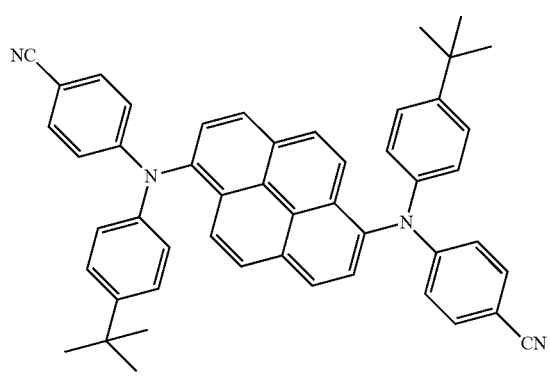
D-11
D-12

-continued
D-13
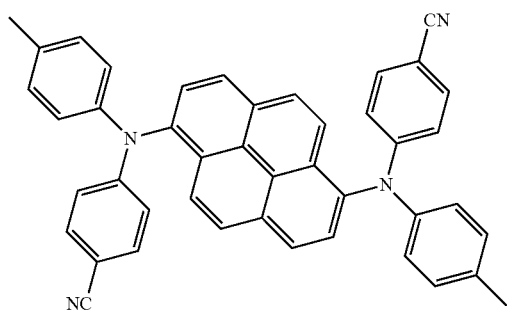
D-14
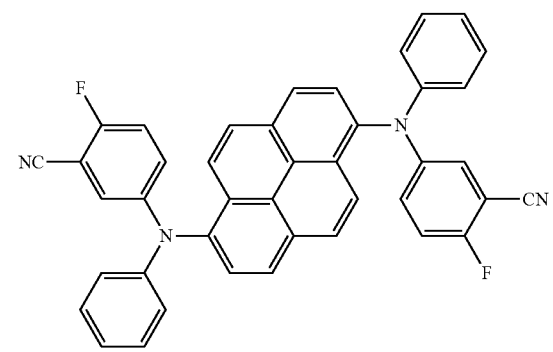
D-15
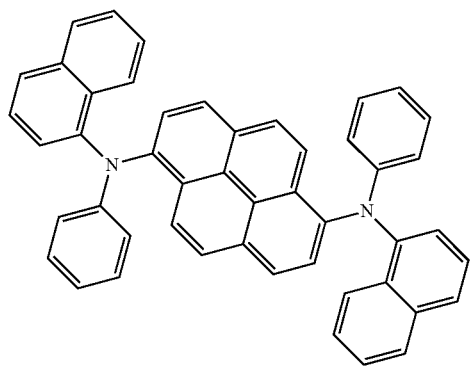
D-16
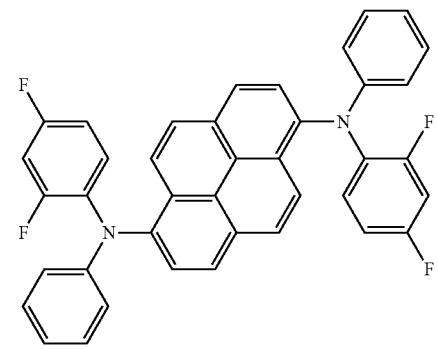
D-17
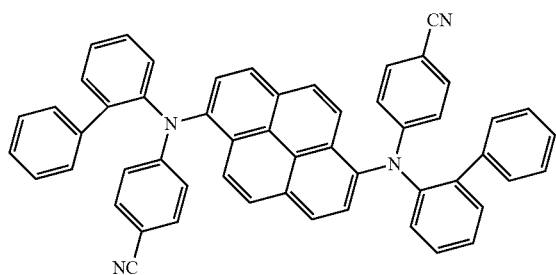
D-18
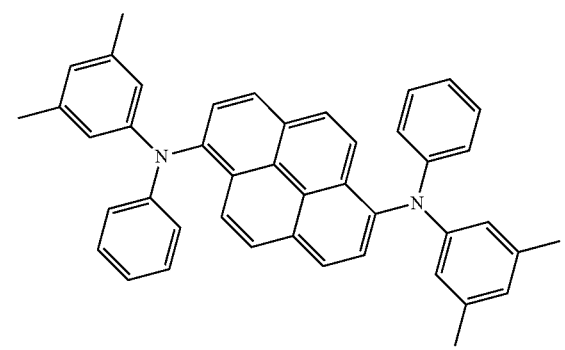
D-19
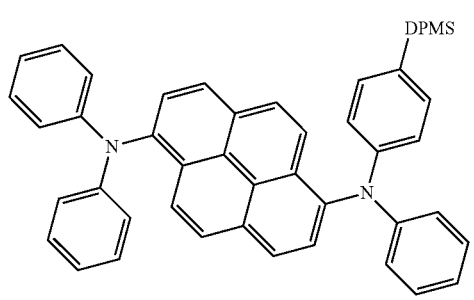
D-20
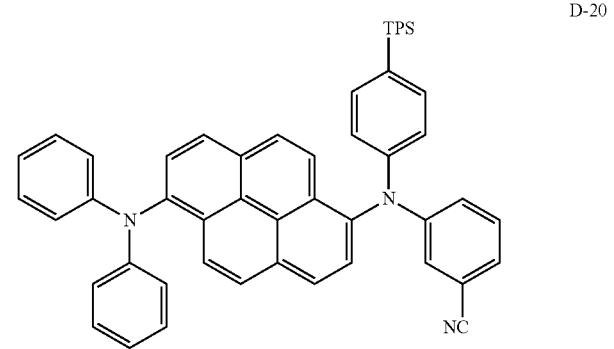

-continued
D-21
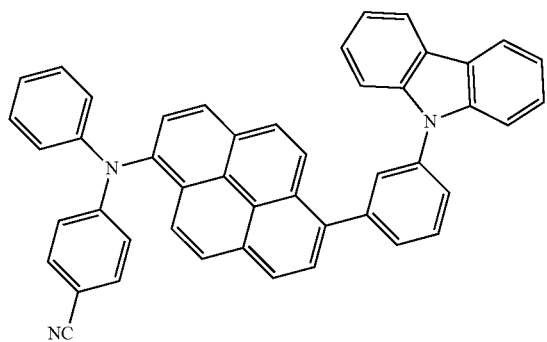
D-22
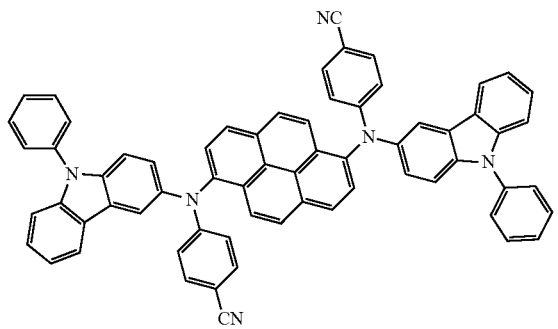
D-23
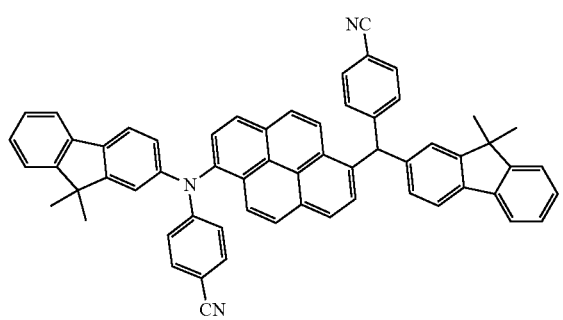
D-24
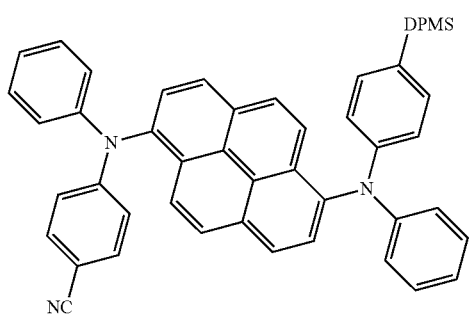
D-25
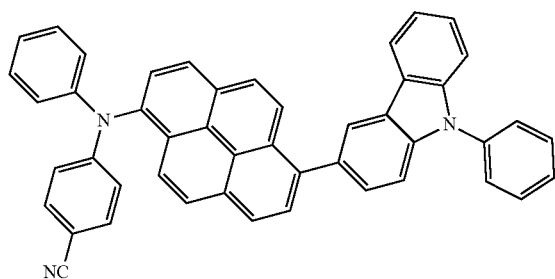
D-26
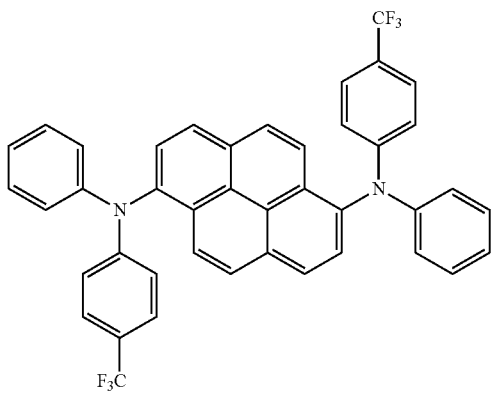
D-27
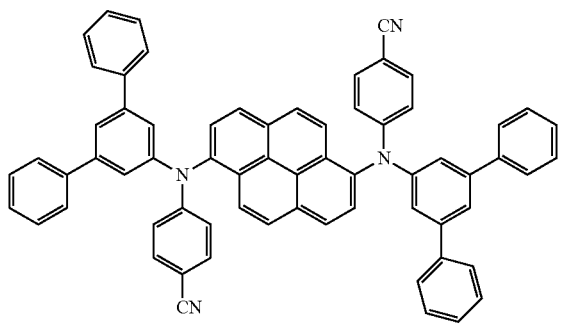
D-28
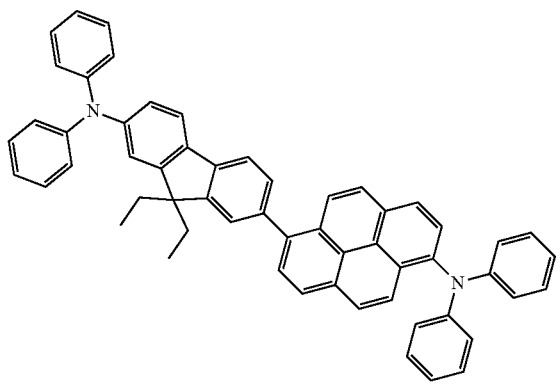

-continued
D-29
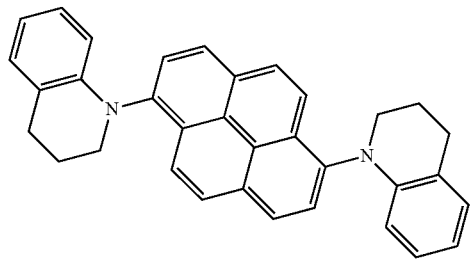
D-30
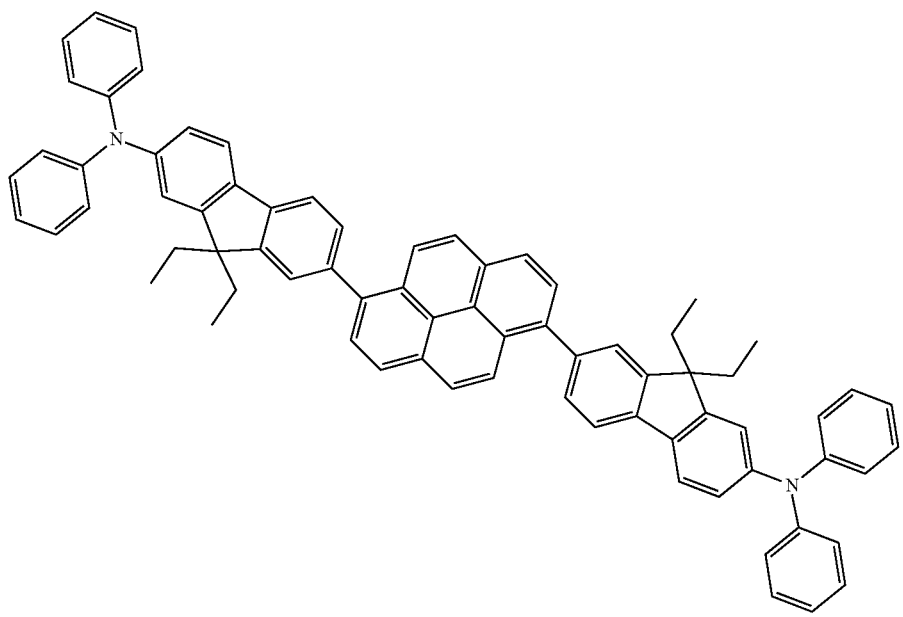
D-31
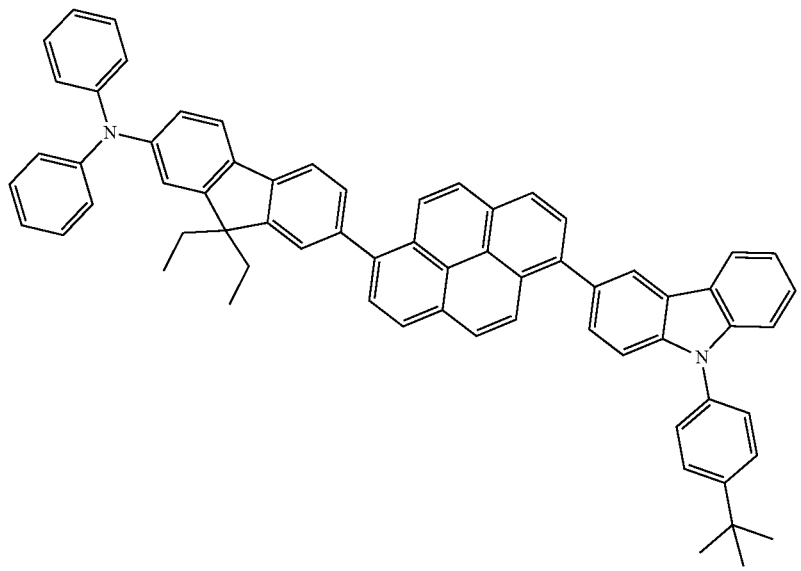

-continued
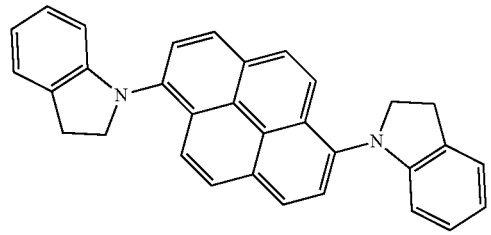
D-32
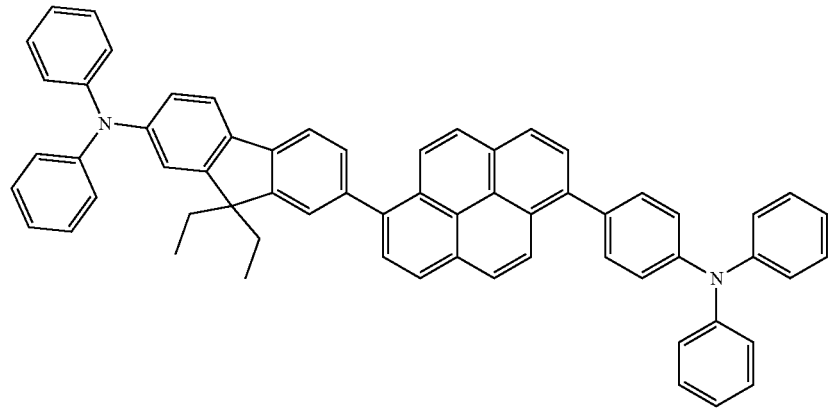
D-33
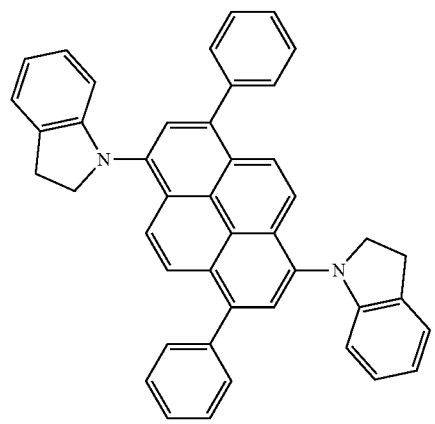
D-34
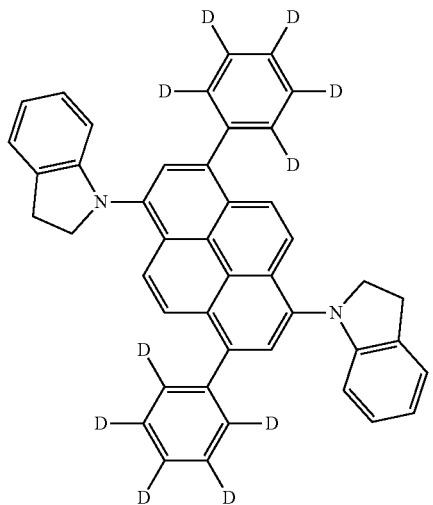
D-35
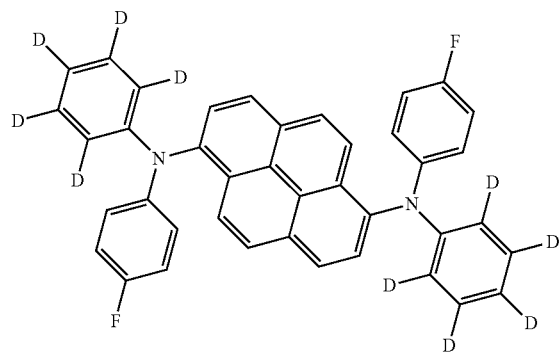
D-36
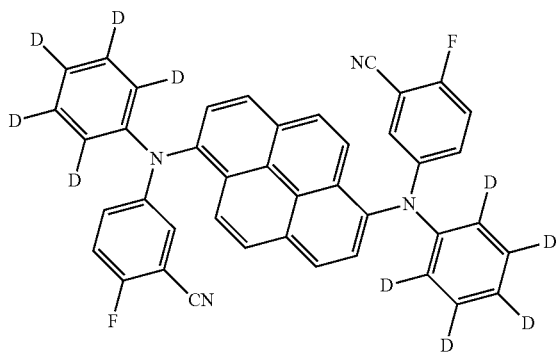
D-37

-continued
D-38
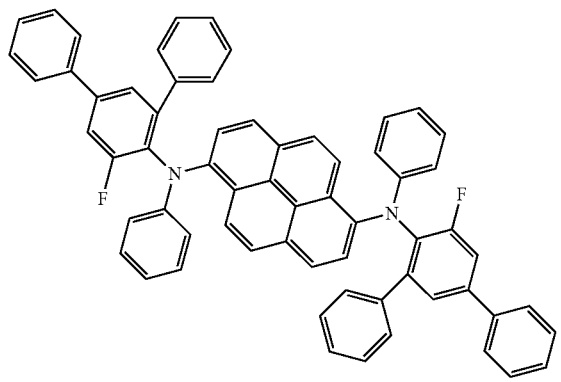
D-39
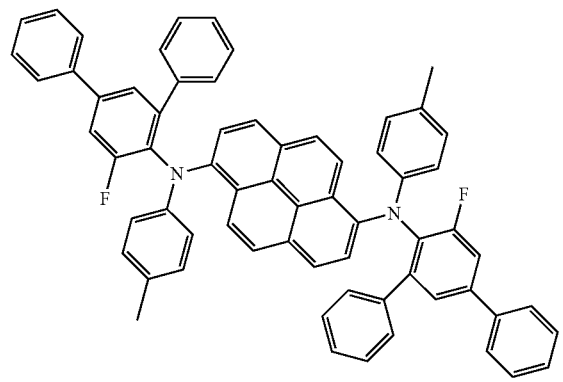
D-40
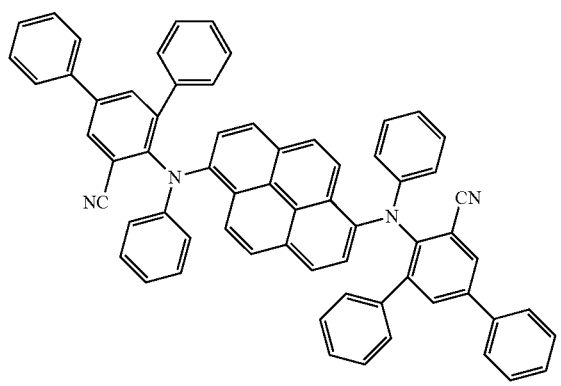
D-41
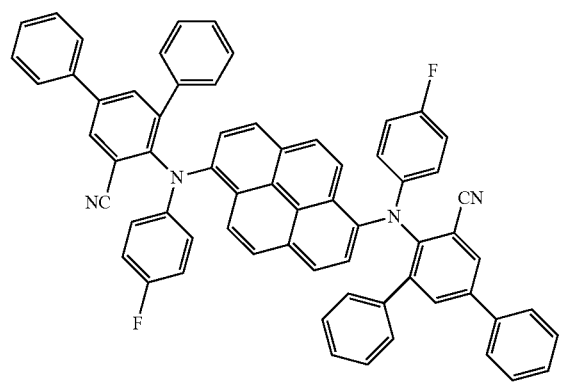
D-42
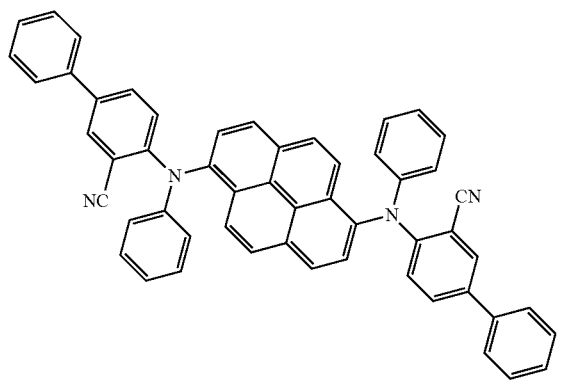
D-43
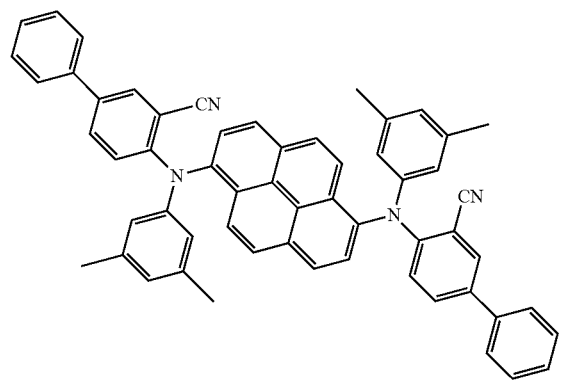

-continued
D-44
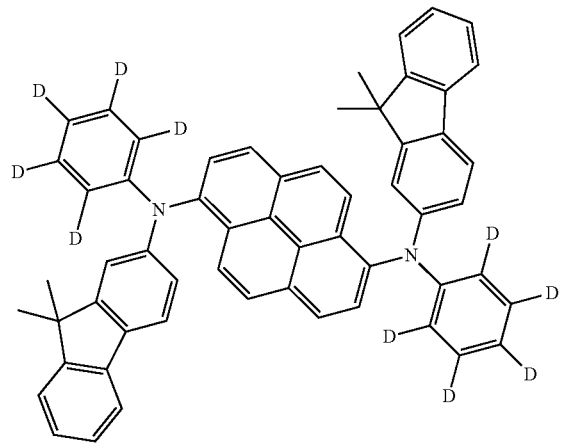
D-45
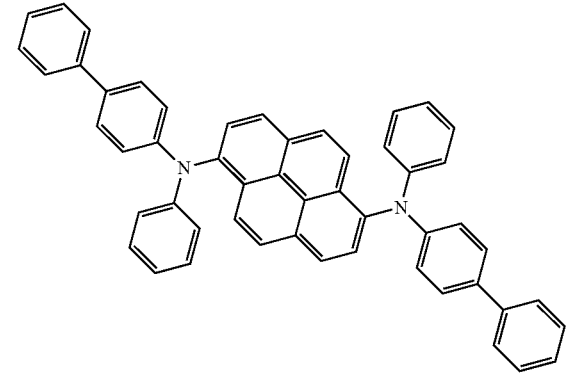
D-46
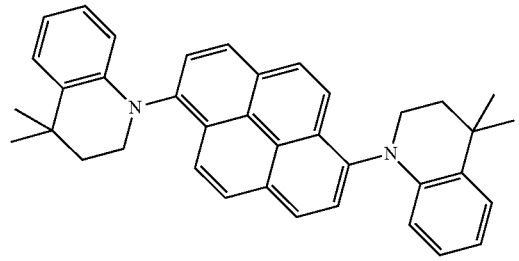
D-47
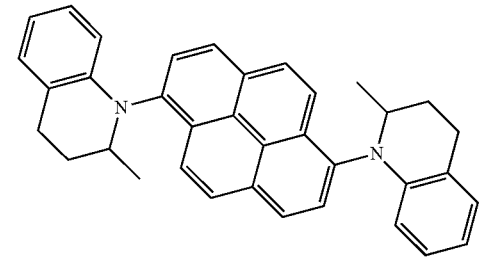
D-48
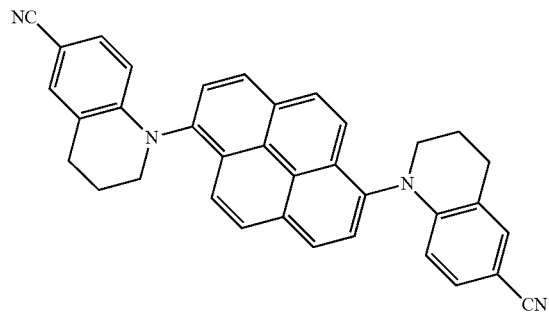
D-49
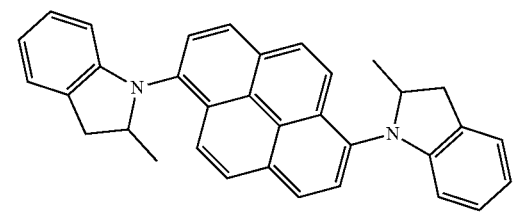
D-50
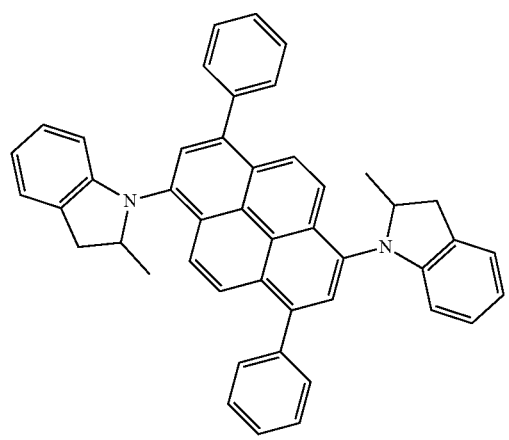
D-51
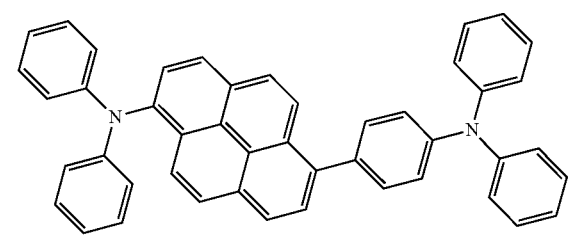

-continued
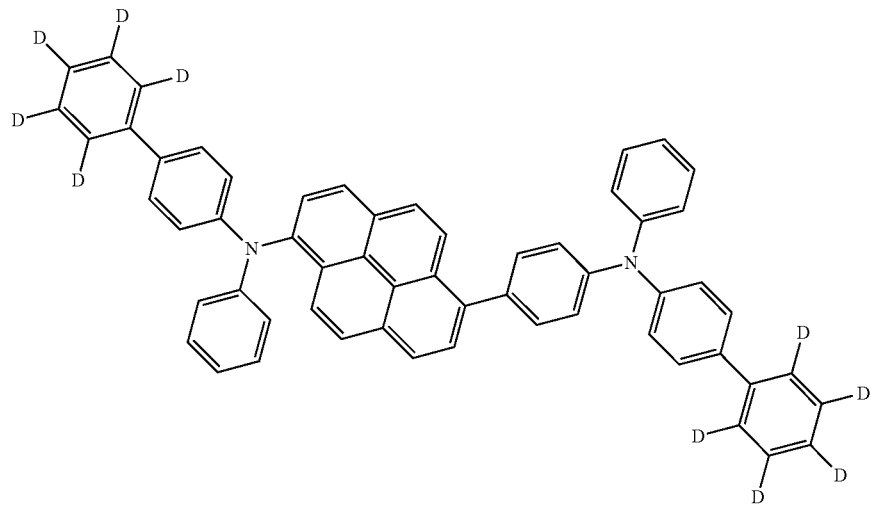
D-52
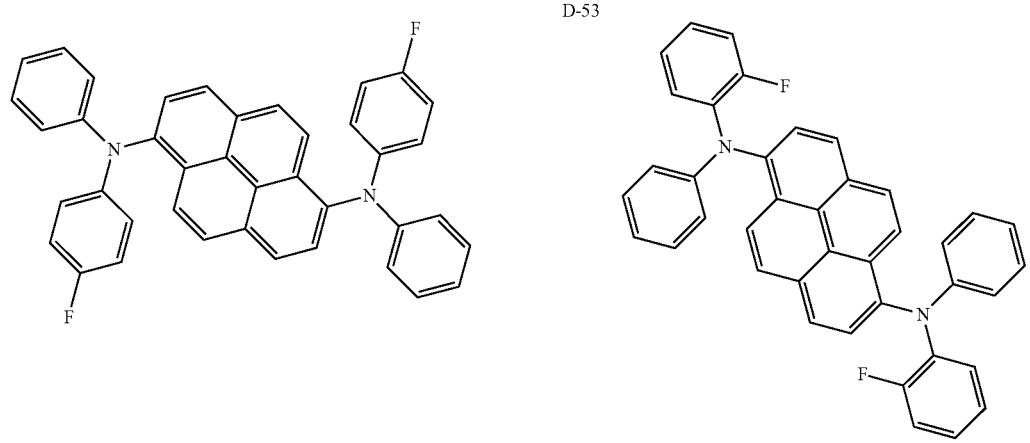
D-53
D-54
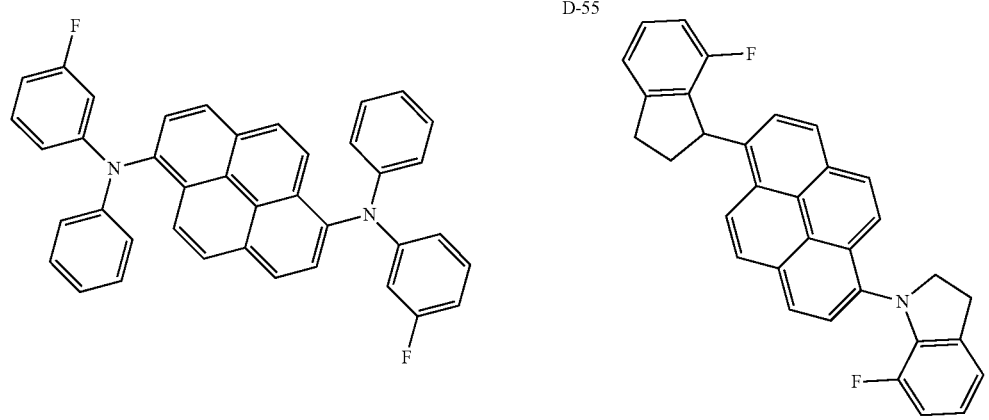
D-55
D-56

-continued
| D-57 | D-58 |
|---|---|
| 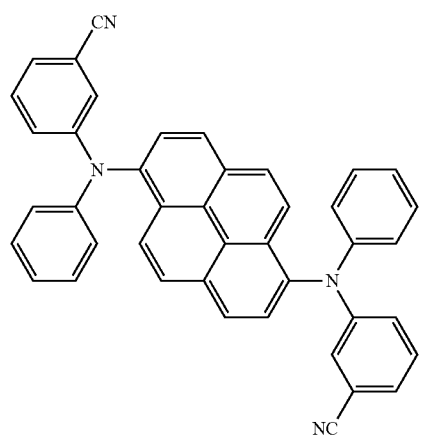 | 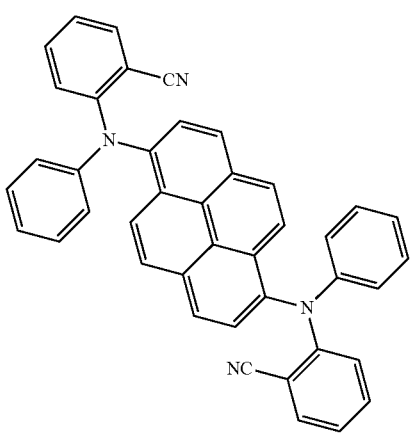 |
| D-59 | D-60 |
| 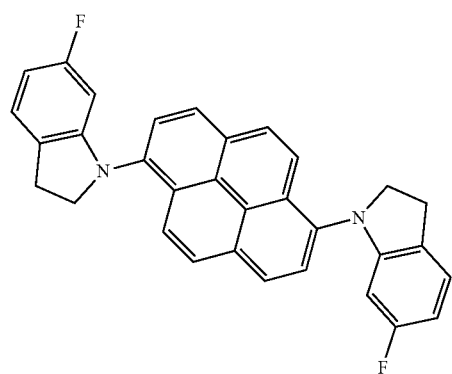 | 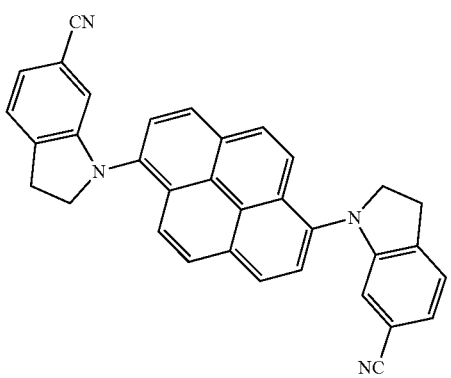 |
| D-61 | D-62 |
| 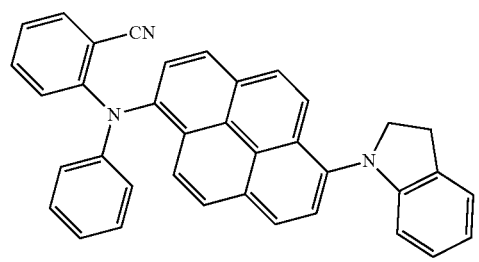 | 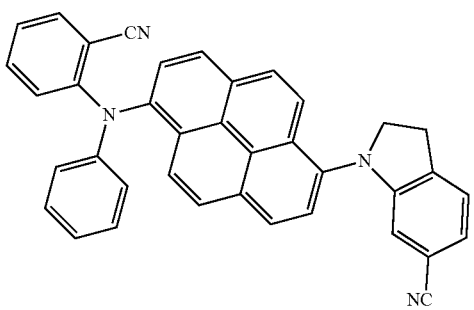 |
| D-63 | D-64 |
| 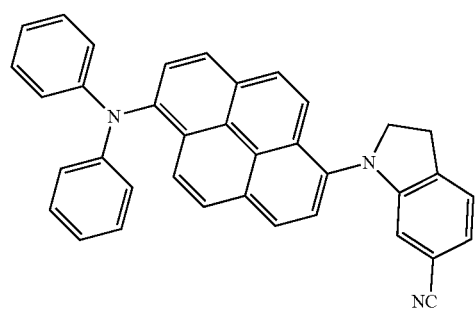 | 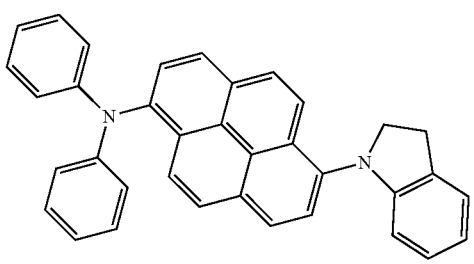 |

-continued
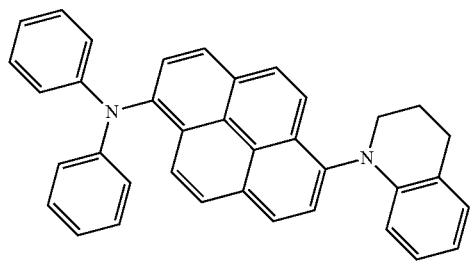
D-65
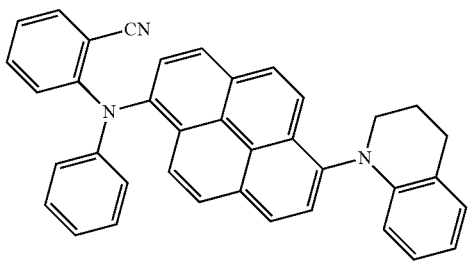
D-66
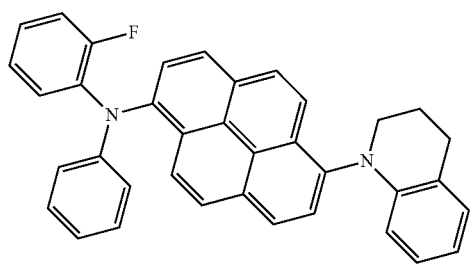
D-67
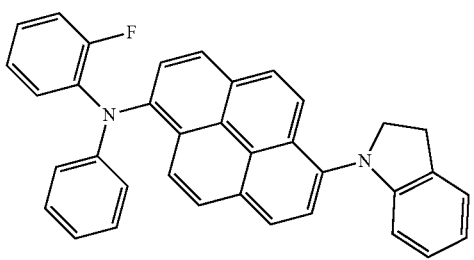
D-68
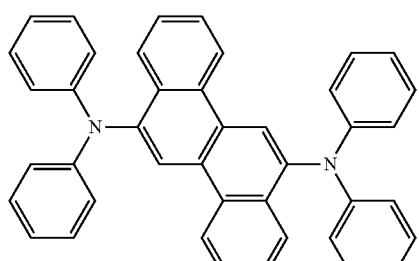
D-69
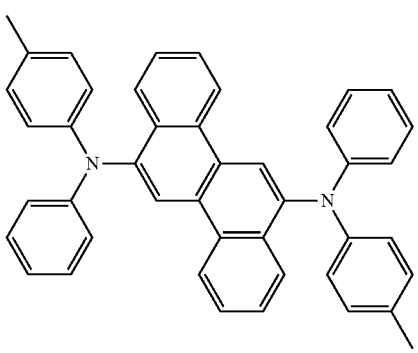
D-70
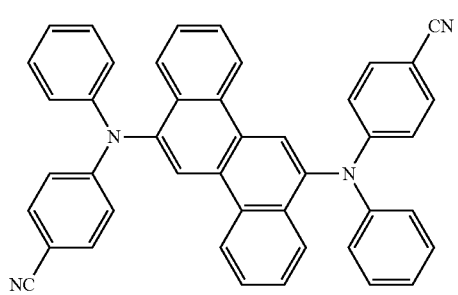
D-71
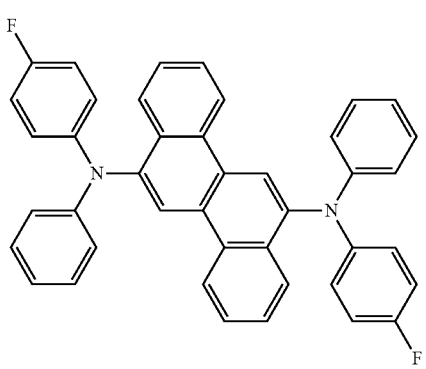
D-72
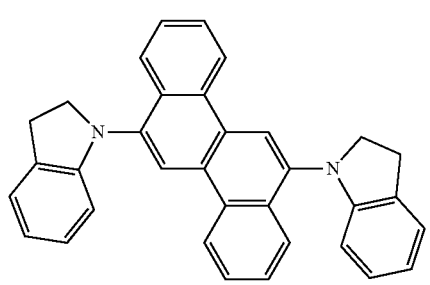
D-73
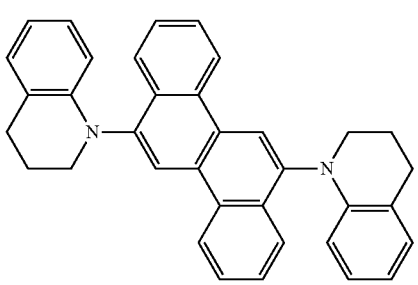
D-74

-continued
D-75
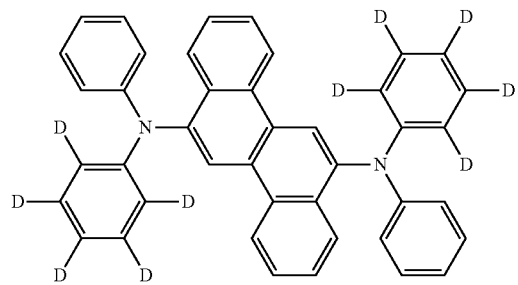
D-76
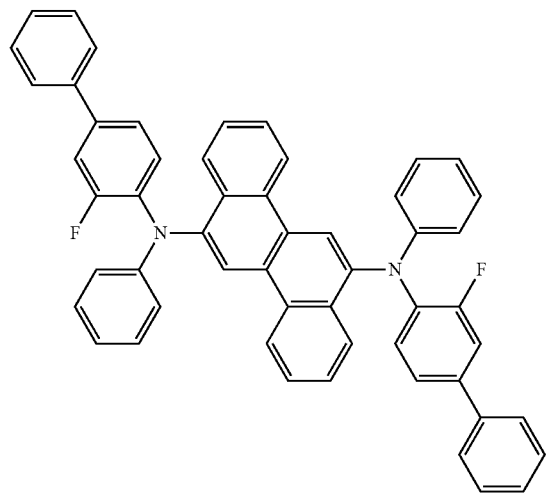
D-77
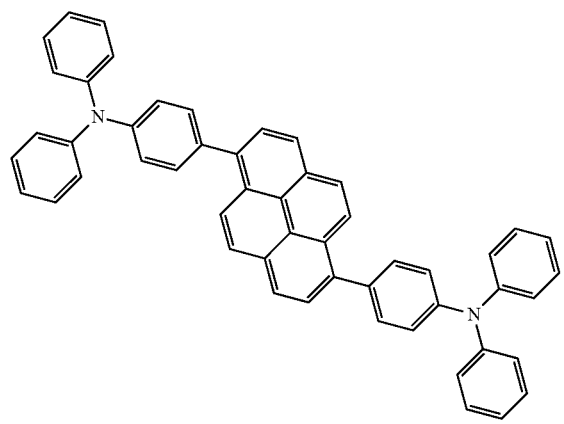
D-78
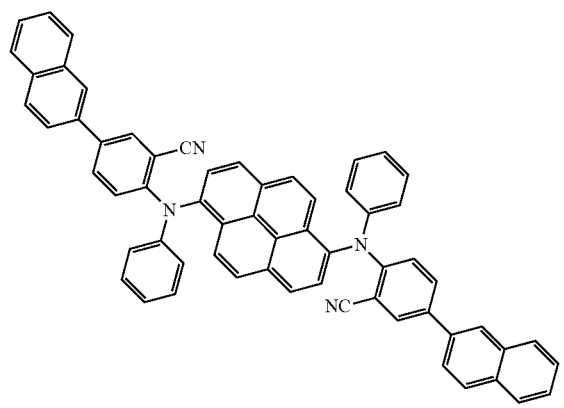
D-79
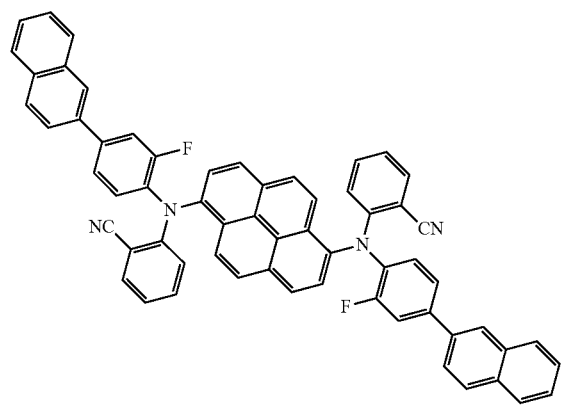
D-80
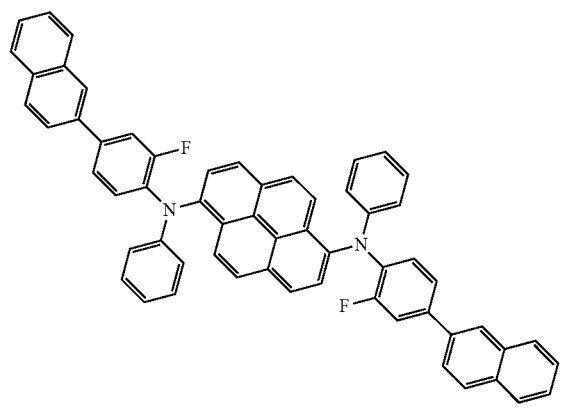

-continued
D-81
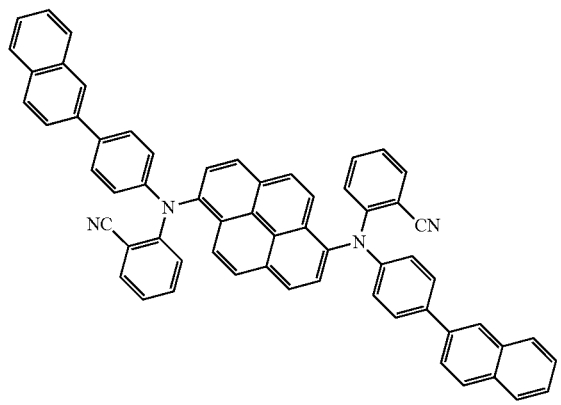
D-82
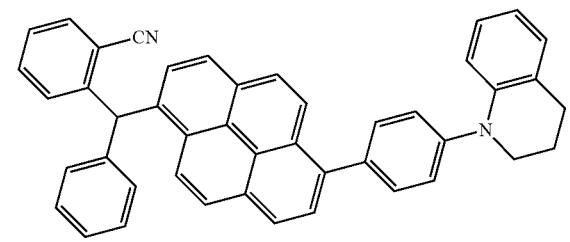
D-83
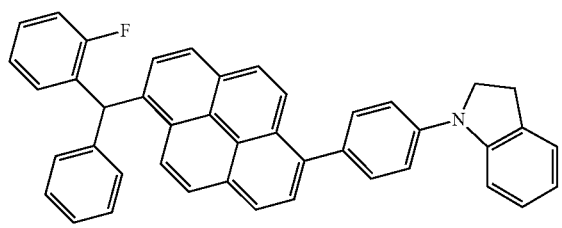
D-84
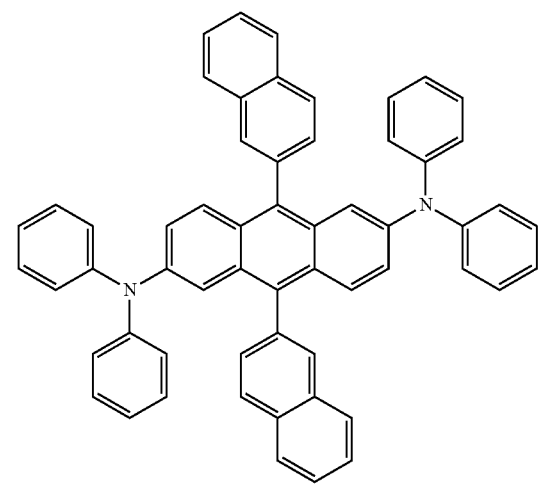
D-85
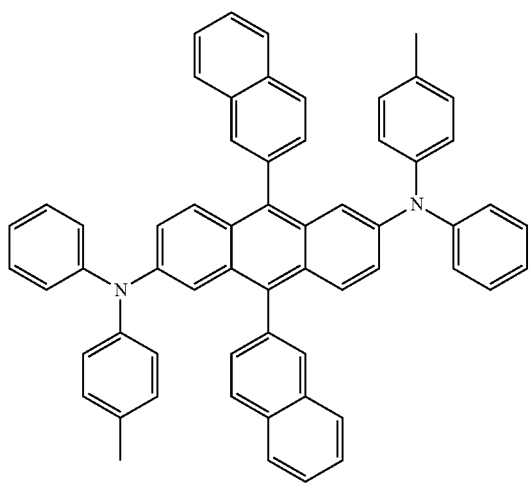
D-86
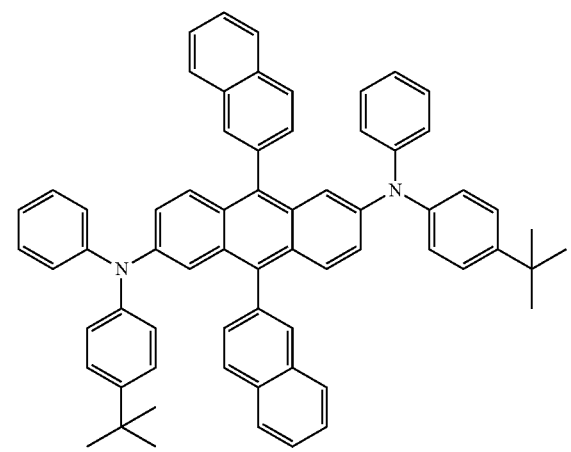

-continued
D-87
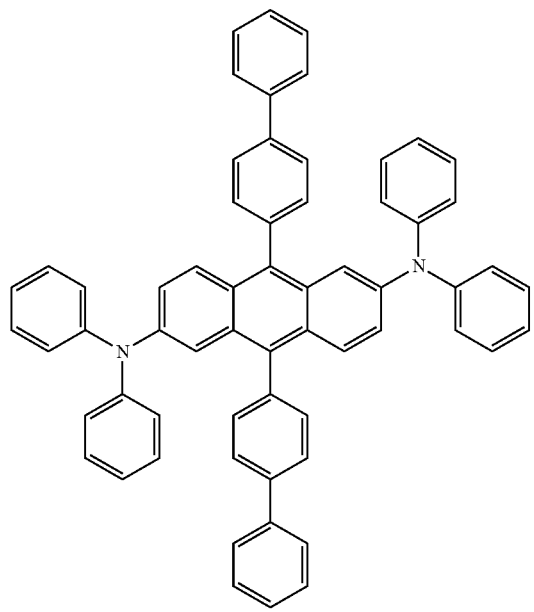
D-88
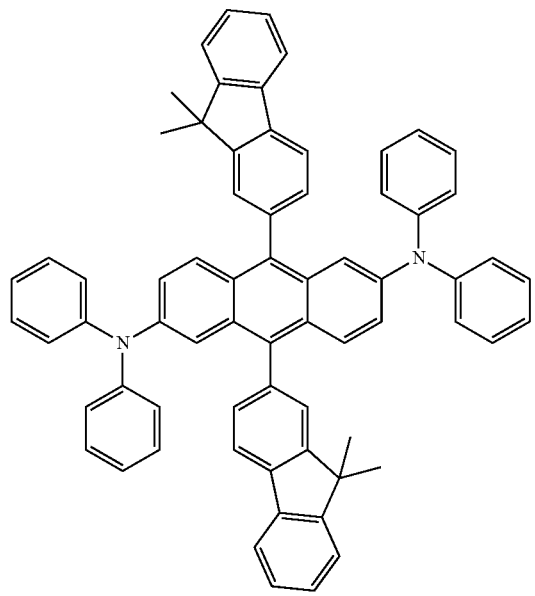
D-89
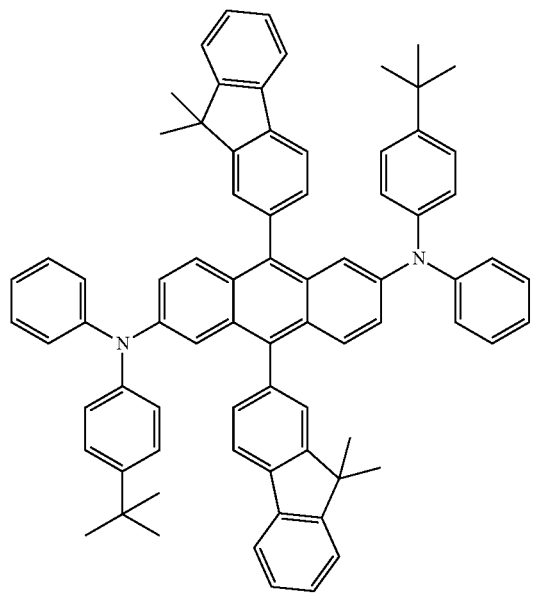
D-90
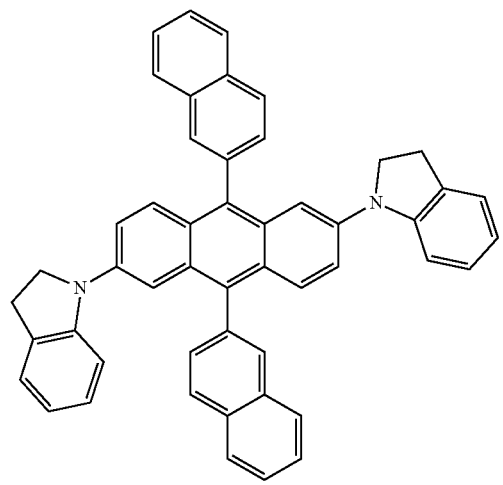

D-91
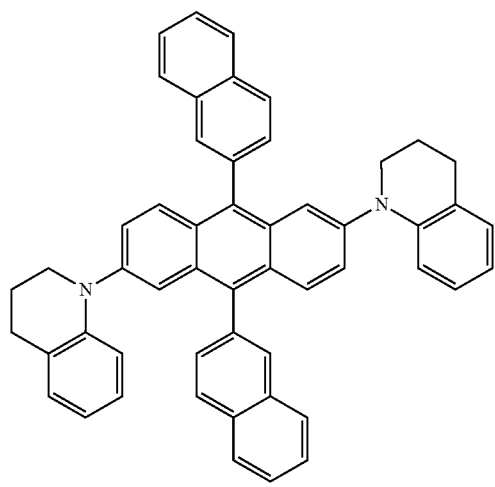
D-92
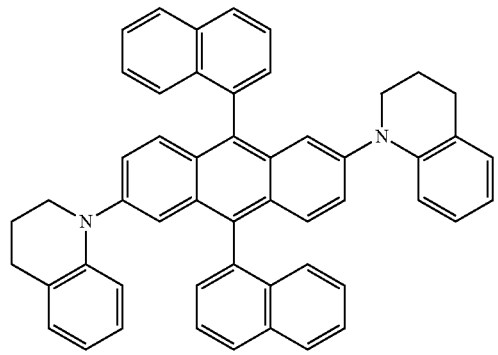
D-93
D-94
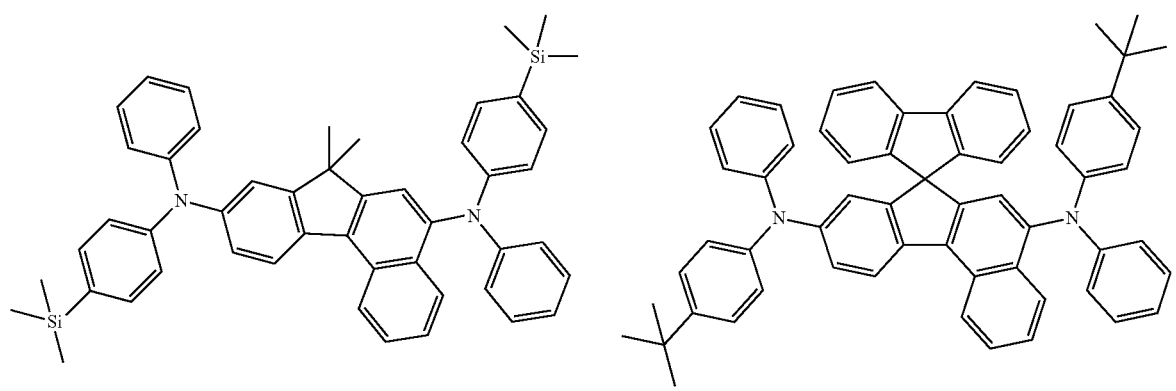
D-95
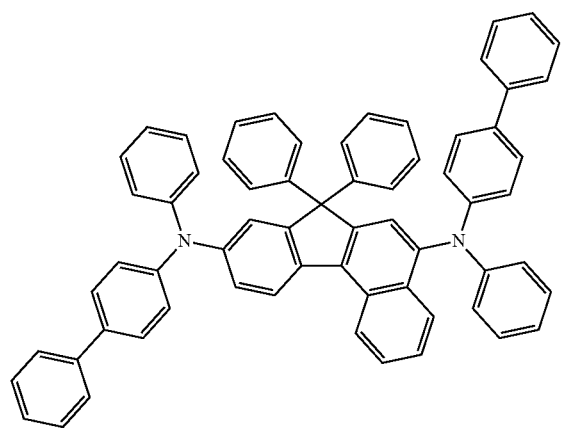

D-96
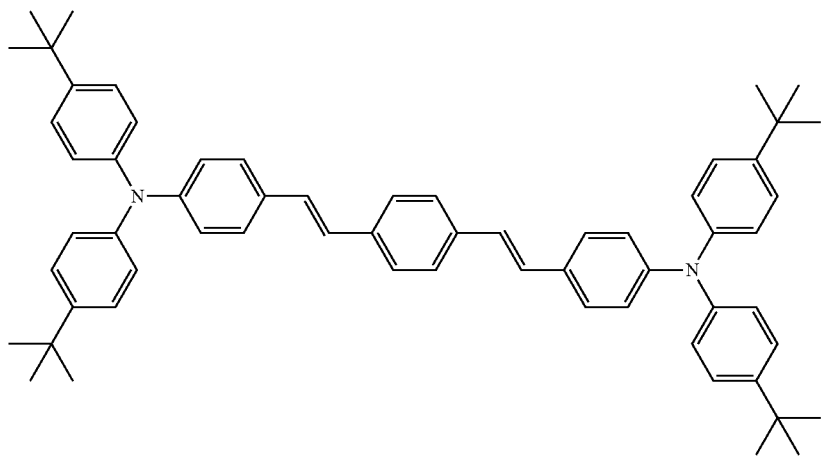
D-97
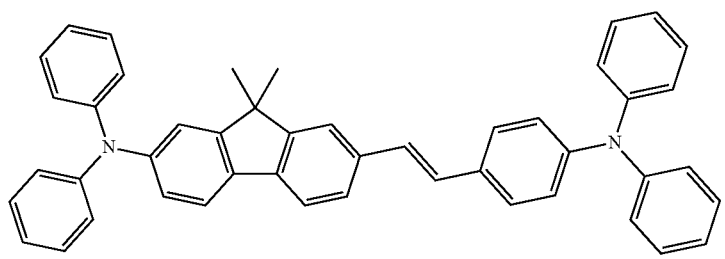
D-98
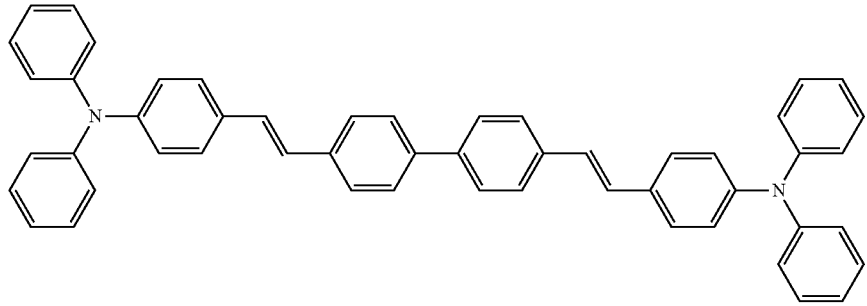
D-99
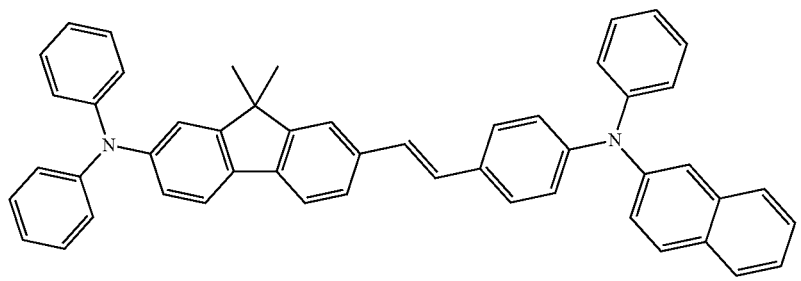
D-100
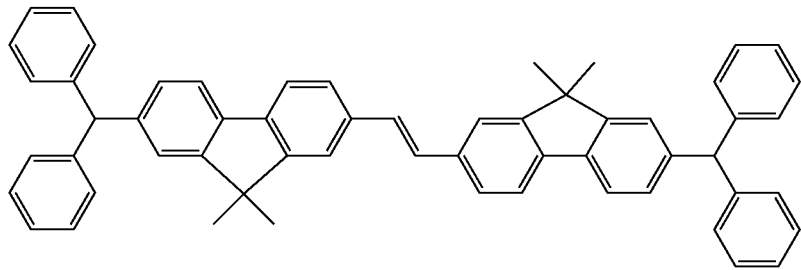

-continued

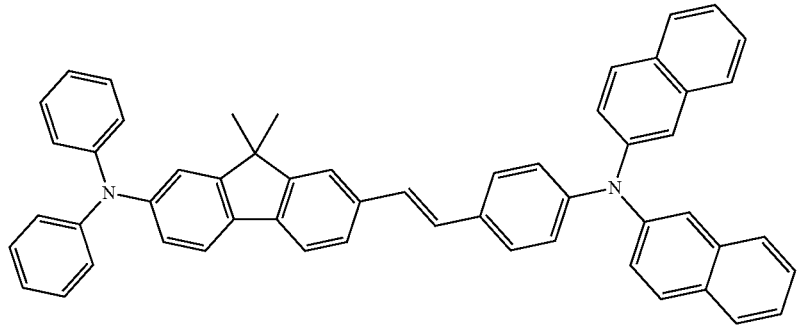
D-101

D-102 D-103

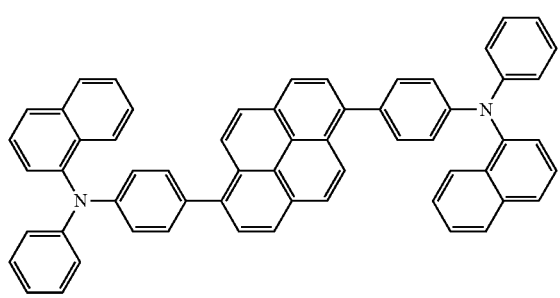
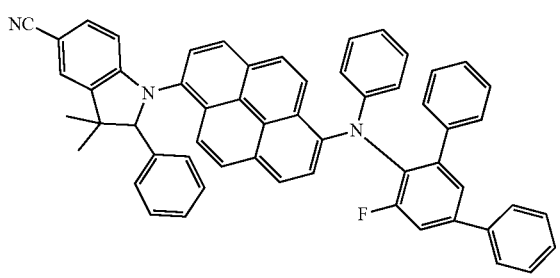

D-104 D-105

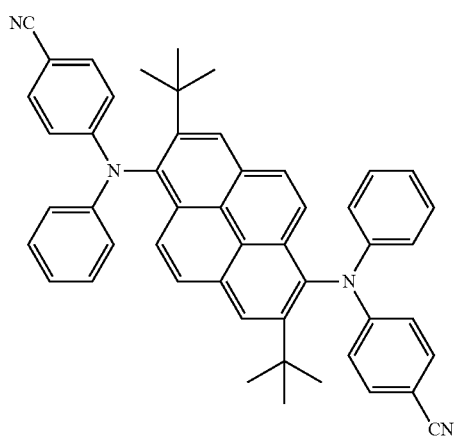

D-106

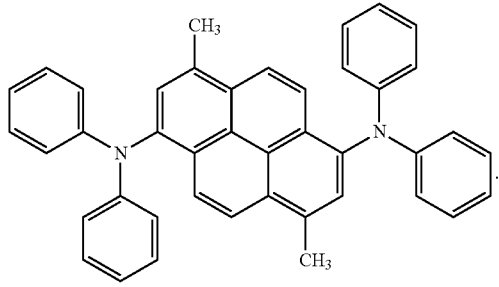

Also, the present disclosure provides an electron transport material or an electron buffer material comprising the organic electroluminescent compound of formula 1.

The electron buffer material refers to a material which controls the flow of charge. Thus, the electron buffer material may be, for example, one trapping electrons, blocking electrons, or lowering the energy barrier between an electron transport zone and a light-emitting layer. In organic electroluminescent devices, the electron buffer material may be used for an electron buffer layer, or may be incorporated in another region such as an electron transport zone or a light-emitting layer, in which the electron buffer layer is placed between a light-emitting layer and an electron transport zone, or between an electron transport zone and a second electrode in the organic electroluminescent devices. The electron buffer material may further include conventional materials generally used for manufacturing organic electroluminescent devices.

Further, if the organic electroluminescent compound of formula 1 is used as an electron transport material, the electron transport material may be composed of the organic electroluminescent compound of formula 1 alone, or may further include conventional materials contained in electron transport materials.

In the organic electroluminescent device according to the present disclosure, the organic layer may further comprise at least one compound selected from the group consisting of arylamine-based compounds and styrylarylamine-based compounds.

In addition, in the organic electroluminescent device according to the present disclosure, the organic layer may further comprise at least one metal selected from the group consisting of metals of Group 1, metals of Group 2, transition metals of the 4$^{th}$ period, transition metals of the 5$^{th}$ period, lanthanides and organic metals of d-transition elements of the Periodic Table, or at least one complex compound comprising said metal.

In addition, the organic electroluminescent device according to the present disclosure may emit white light by further comprising at least one light-emitting layer which comprises a blue light-emitting compound, a red light-emitting compound or a green light-emitting compound known in the field, besides the compound according to the present disclosure. Also, if necessary, a yellow or orange light-emitting layer can be further comprised in the device.

In the organic electroluminescent device according to the present disclosure, at least one layer (hereinafter, "a surface layer") is preferably placed on an inner surface(s) of one or both electrode(s); selected from a chalcogenide layer, a metal halide layer, and a metal oxide layer. Specifically, a chalcogenide (including oxides) layer of silicon or aluminum is preferably placed on an anode surface of a light-emitting medium layer, and a metal halide layer or a metal oxide layer is preferably placed on a cathode surface of a light-emitting medium layer. Such a surface layer provides operation stability for the organic electroluminescent device. Preferably, said chalcogenide includes $SiO_X$ ($1 \leq X \leq 2$), $AlO_X$ ($1 \leq X \leq 5$), SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic EL device having two or more light-emitting layers which emits white light.

In order to form each layer constituting the organic electroluminescent device of the present disclosure, dry film-forming methods such as vacuum deposition, sputtering, plasma, ion plating methods, etc., or wet film-forming methods such as spin coating, dip coating, flow coating methods, etc., can be used. When forming the film of the first and second host compounds of the present disclosure, a co-evaporation or a mixed evaporation method is used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a film.

By using the organic electroluminescent device of the present disclosure, a display device, for example, for smartphones, tablets, notebooks, PCs, TVs, or vehicles, or a lighting device, for example, an indoor or outdoor lighting device, can be produced.

Hereinafter, the preparation method of the compounds of the present disclosure, the physical properties of the compounds, and the luminous properties of the organic electroluminescent device comprising the compounds will be explained in detail with reference to the representative compounds of the present disclosure. However, the present disclosure is not limited to the Examples below.

Example 1

Preparation of Compound C-2

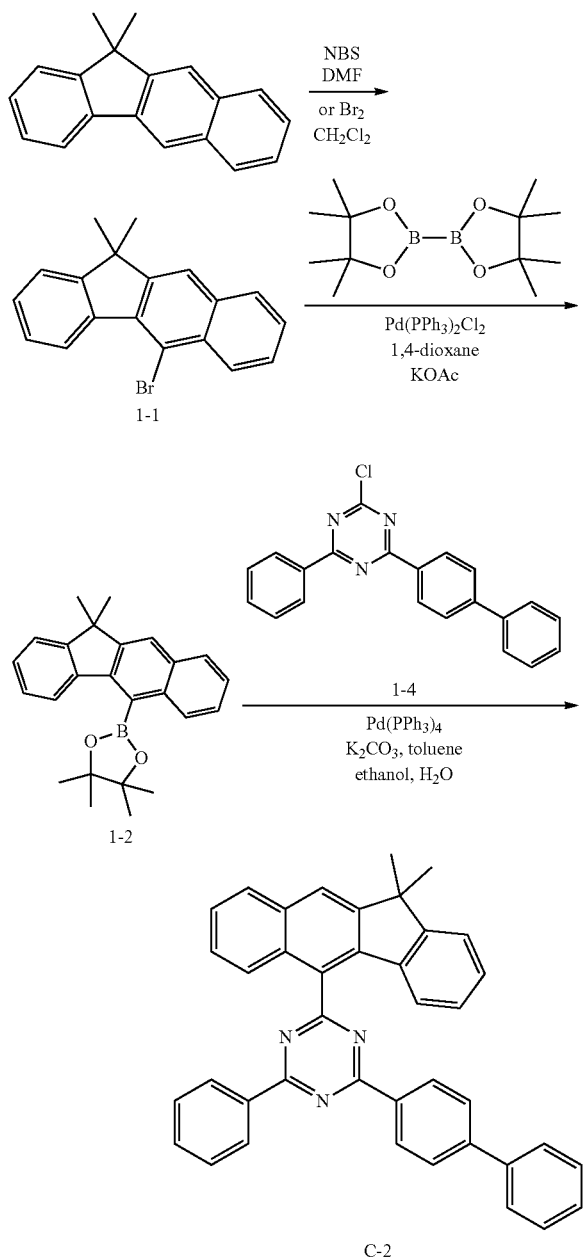

Preparation of Compound 1-1

In a reaction vessel, 3 g of 11,11-dimethyl-11H-benzo[b]fluorene (12 mmol) was dissolved in 50 mL of methylene chloride. 1.3 g of bromine (16 mmol) was dissolved in 10 mL of methylene chloride at 0° C. and added to the reaction mixture. The reaction mixture was stirred at room temperature for 2 hours. The reaction solution was diluted with methylene chloride and washed with distilled water. The extracted organic layer was dried with magnesium sulfate and the solvent was removed by a rotary evaporator. The precipitated solid was filtered and washed with cold methyl alcohol to obtain 1.8 g of compound 1-1 (yield: 45%).

Compound 1-1 may also be prepared by the following method.

1.3 g of 11,11-dimethyl-11H-benzo[b]fluorene (5 mmol), 10 mL of dimethylformamide (DMF), and 1.23 g of N-bromosuccinimide (NBS) (7 mmol) were introduced into a reaction vessel and stirred overnight at room temperature. The reaction solution was diluted with ethyl acetate (EA) and washed with distilled water. The extracted organic layer was dried with magnesium sulfate and the solvent was removed by a rotary evaporator. The precipitated solid was filtered and washed with cold methyl alcohol to obtain 620 mg of compound 1-1 (yield: 36%).

Preparation of Compound 1-2

20 g of compound 1-1 (62 mmol), 24 g of bis(pinacolato)diboron (93 mmol), 2.2 g of dichloro(triphenylphosphine)palladium (3.1 mmol), 15 g of potassium acetate (155 mmol), and 310 mL of 1,4-dioxane were introduced into a reaction vessel and stirred at 120° C. for 20 hours. After completion of the reaction, the reaction mixture was cooled to room temperature and the solid was removed through a celite filter. The solvent was removed by a rotary evaporator. The residue was purified by column chromatography to obtain 14 g of compound 1-2 (yield: 61%).

Preparation of Compound C-2

11 g of compound 1-2 (30 mmol), 10 g of compound 1-4 (30 mmol), 1.7 g of tetrakis(triphenylphosphine)palladium (1.5 mmol), 10 g of potassium carbonate (74 mmol), 80 mL of toluene, and 40 mL of ethanol were introduced into a reaction vessel, and 40 mL of distilled water was added to the reaction mixture and stirred at 120° C. for 7 hours. After completion of the reaction, toluene and ethanol were removed by a rotary evaporator. The organic layer was extracted with methylene chloride and distilled water, and then dried with magnesium sulfate. The solvent was removed by a rotary evaporator. The residue was purified by column chromatography to obtain 6.9 g of compound C-2 (yield: 42%).

| | | | | MS/EIMS (M + H) | |
|---|---|---|---|---|---|
| Yield (%) | UV (nm) | PL (nm) | M.P. (° C.) | Measured | Calculated |
| 42 | 368 | 463 | 191 | 552.1 | 552.2 |

Example 2

Preparation of Compound C-22

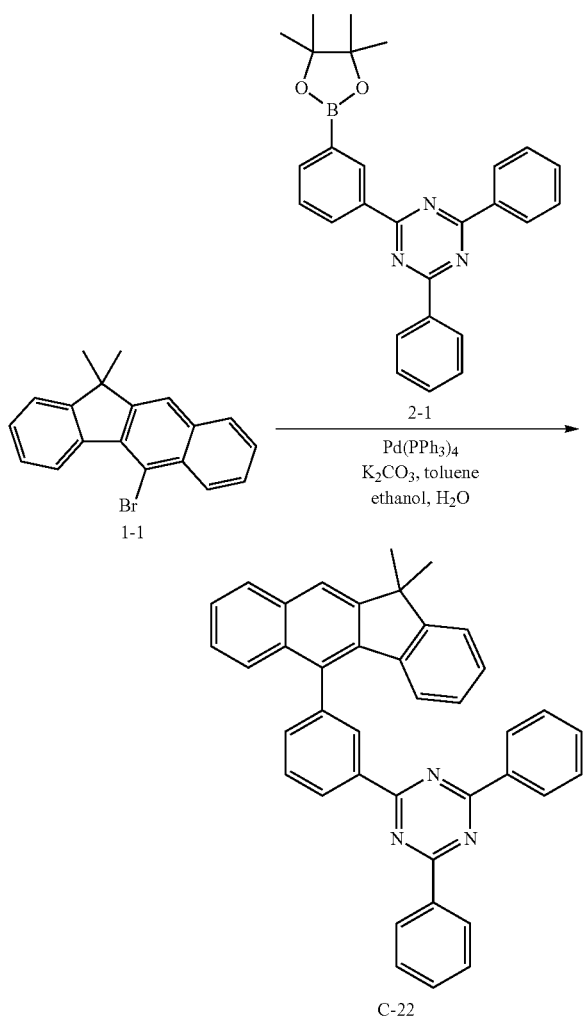

12 g of compound 1-1 (37 mmol), 16 g of compound 2-1 (37 mmol), 2.1 g of tetrakis(triphenylphosphine)palladium (1.9 mmol), 10 g of potassium carbonate (74 mmol), 150 mL of toluene, and 74 mL of ethanol were introduced into a reaction vessel, and 74 mL of distilled water was added to the reaction mixture and stirred at 80° C. for 18 hours. After completion of the reaction, the solvent was removed by a rotary evaporator. The organic layer was extracted with methylene chloride and distilled water, and then dried with magnesium sulfate. The solvent was removed by a rotary evaporator. The residue was purified by column chromatography to obtain 11 g of compound C-22 (yield: 54%).

| Yield (%) | UV (nm) | PL (nm) | M.P. (° C.) | MS/EIMS (M + H) | |
|---|---|---|---|---|---|
| | | | | Measured | Calculated |
| 54 | 344 | 459 | 298 | 552.1 | 552.2 |

Comparison of the Glass Transition Temperature (Tg) Between the Compound According to the Present Disclosure and the Conventional Compound In order to analyze the heat resistance of the organic electroluminescent compound, the glass transition temperature of the compounds according to the present disclosure and the conventional compounds was measured. The glass transition temperature was measured by the following method.

A sample was heated at 10 K/min and the midpoint of the transition was defined as the glass transition temperature (Tg). The glass transition temperature was measured by differential scanning calorimetry (Model Q2000, TA Instruments).

The measurement results are shown in Table 1 below.

TABLE 1

| | HOMO (eV) | LUMO (eV) | Et(eV) (triplet energy) | MW | Tg (° C.) |
|---|---|---|---|---|---|
| C-22 | −5.52 | −1.84 | 2.52 | 551.69 | 133.33 |
| C-2 | −5.54 | −1.92 | 2.49 | 551.69 | 136.75 |
| Ref-1 | −5.47 | −1.84 | 2.46 | 551.69 | 111.13 |
| Ref-2 | −5.63 | −1.96 | 2.37 | 551.69 | 120.29 |
| Ref-3 | −5.84 | −1.89 | 2.64 | 501.63 | 91.86 |
| Ref-4 | −5.46 | −1.95 | 2.16 | 551.69 | 109.90 |
| Ref-5 | −5.81 | −1.89 | 2.59 | 591.76 | 120.45 |

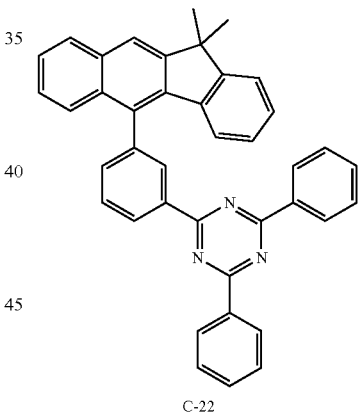

C-22

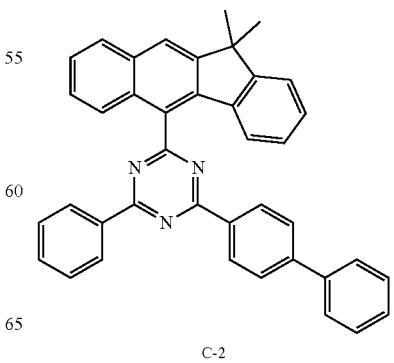

C-2

TABLE 1-continued

| HOMO (eV) | LUMO (eV) | Et(eV) (triplet energy) | MW | Tg (° C.) |
|---|---|---|---|---|

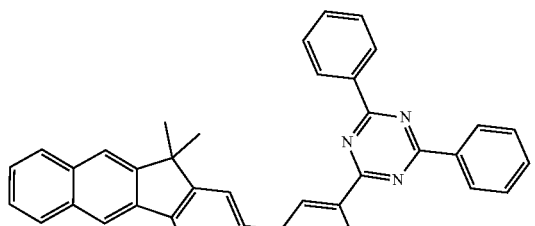
Ref-1

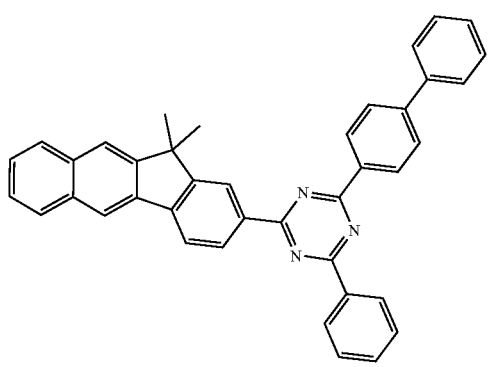
Ref-2

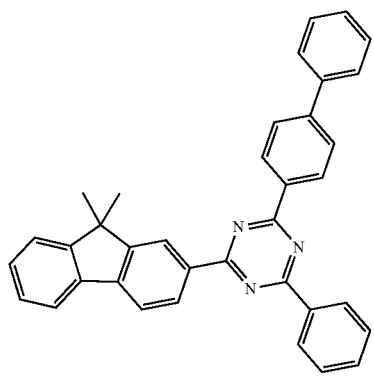
Ref-3

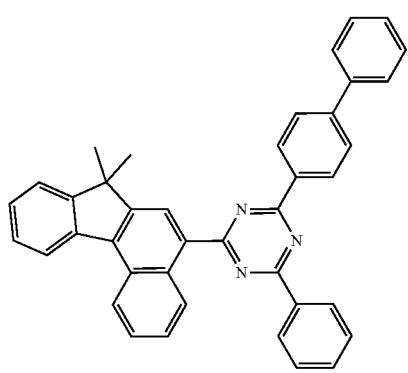
Ref-4

TABLE 1-continued

| HOMO (eV) | LUMO (eV) | Et(eV) (triplet energy) | MW | Tg (° C.) |
|---|---|---|---|---|

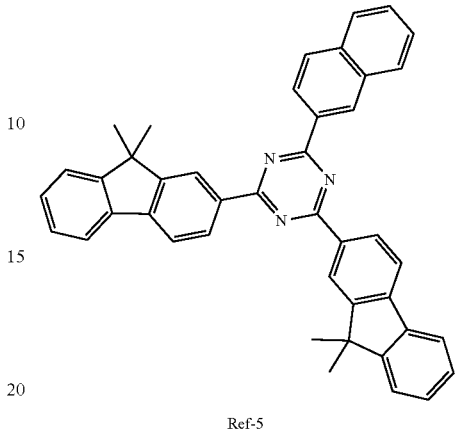
Ref-5

From Table 1, it can be seen that the compounds according to the present disclosure (compounds C-2 and C-22) have higher glass transition temperatures than the conventional compounds (Ref-1, 2, and 4) having the same molecular weight. Further, the compounds according to the present disclosure were measured to have a glass transition temperature of about 15° C. higher than the conventional compound (Ref-5) of higher molecular weight. That is, the organic electroluminescent compound according to the present disclosure does not cause crystallization and aggregation at high temperatures during the driving of the organic electroluminescent device, thereby contributing to the improvement of the lifespan of the organic electroluminescent device.

Comparative Example 1

Production of a Blue Light-Emitting OLED Device Comprising a Conventional Compound An organic light-emitting diode (OLED) device was produced comprising a conventional compound. A transparent electrode indium tin oxide (ITO) thin film (10 Ω/sq) on a glass substrate for an OLED device (Geomatec, Japan) was subjected to an ultrasonic washing with acetone and isopropyl alcohol, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-7}$ torr. Thereafter, an electric current was applied to the cell to evaporate the above-introduced material, thereby forming a first hole injection layer having a thickness of 60 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 20 nm on the second hole injection layer. Compound HT-2 was introduced into another cell of said vacuum vapor depositing apparatus, and was evaporated by applying an electric current to the cell, thereby forming a second hole transport layer having a thickness of 5 nm on the first hole transport layer. After forming the hole injection layers and the hole transport layers, a light-emitting layer was then deposited as follows. Compound H-15 was introduced into one cell of the vacuum vapor depositing apparatus as a host, and compound D-38 was introduced into another cell as a dopant. The two materials were evaporated at different rates and were deposited in a doping amount of 2 wt % based on the total amount of the host and dopant to form a light-emitting layer having a thickness of 20 nm on the second hole transport layer. Compound Ref-4 and compound EI-1 were then introduced into other two cells, simultaneously evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced. All the materials used for producing the OLED device were purified by vacuum sublimation at $10^{-6}$ torr.

The driving voltage, luminous efficiency, and color coordinates based on a luminance of 1,000 nits of the produced OLED device are provided in Table 2 below.

Device Examples 1 and 2

Production of a Blue Light-Emitting OLED Device Comprising the Compound According to the Present Disclosure In Device Examples 1 and 2, an OLED device was produced in the same manner as in Comparative Example 1, except that the electron transport material shown in Table 2 below was used as an electron transport material. The driving voltage, luminous efficiency, and color coordinates based on a luminance of 1,000 nits of the OLED devices of Device Examples 1 and 2 are provided in Table 2 below.

TABLE 2

| | Electron Transport Material | Driving Voltage (V) | Luminous Efficiency (cd/A) | Color Coordinate (x) | Color Coordinate (y) |
|---|---|---|---|---|---|
| Comparative Example 1 | Ref-4 | 4.6 | 4.4 | 0.140 | 0.089 |
| Device Example 1 | C-2 | 3.9 | 6.4 | 0.140 | 0.090 |
| Device Example 2 | C-22 | 4.1 | 6.8 | 0.139 | 0.091 |

From Table 2 above, it can be seen that the organic electroluminescent device comprising the compound of the present disclosure has a lower driving voltage and higher luminous efficiency compared to the organic electroluminescent device comprising a conventional compound.

Comparative Example 2

Production of a Blue Light-Emitting OLED Device Comprising a Conventional Compound An organic light-emitting diode (OLED) device was produced comprising a conventional compound. A transparent electrode indium tin oxide (ITO) thin film (10 Ω/sq) on a glass substrate for an OLED device (Geomatec, Japan) was subjected to an ultrasonic washing with acetone and isopropyl alcohol, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-7}$ torr. Thereafter, an electric current was applied to the cell to evaporate the above-introduced material, thereby forming a first hole injection layer having a thickness of 60 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 20 nm on the second hole injection layer. Compound HT-2 was introduced into another cell of said vacuum vapor depositing apparatus, and was evaporated by applying an electric current to the cell, thereby forming a second hole transport layer having a thickness of 5 nm on the first hole transport layer. After forming the hole injection layers and the hole transport layers, a light-emitting layer was then deposited as follows. Compound H-15 was introduced into one cell of the vacuum vapor depositing apparatus as a host, and compound D-38 was introduced into another cell as a dopant. The two materials were evaporated at different rates and were deposited in a doping amount of 2 wt % based on the total amount of the host and dopant to form a light-emitting layer having a thickness of 20 nm on the second hole transport layer. Compound Ref-2 was deposited as an electron buffer material to form an electron buffer layer having a thickness of 5 nm on the light-emitting layer. Compound ET-1 was introduced into one cell of said vacuum vapor depositing apparatus as an electron transport material, and was evaporated to form an electron transport layer having a thickness of 30 nm on the electron buffer layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced. All the materials used for producing the OLED device were purified by vacuum sublimation at $10^{-6}$ torr.

The driving voltage, luminous efficiency, and color coordinates based on a luminance of 1,000 nits of the produced OLED device are provided in Table 3 below.

Device Example 3

Production of a Blue Light-Emitting OLED Device Comprising the Compound According to the Present Disclosure In Device Example 3, an OLED device was produced in the same manner as in Comparative Example 2, except that the electron buffer material shown in Table 3 below was used as an electron buffer material. The driving voltage, luminous efficiency, and color coordinates based on a luminance of 1,000 nits of the OLED device of Device Example 3 are provided in Table 3 below.

TABLE 3

| Electron Buffer Material | Driving Voltage (V) | Luminous Efficiency (cd/A) | Color Coordinate (x) | Color Coordinate (y) |
|---|---|---|---|---|
| Comparative Example 2 | Ref-2 | 4.5 | 4.9 | 0.140 | 0.088 |
| Device Example 3 | C-2 | 4.0 | 6.3 | 0.140 | 0.088 |

From Table 3 above, it can be seen that the organic electroluminescent device comprising the compound of the present disclosure has a lower driving voltage and higher luminous efficiency compared to the organic electroluminescent device comprising a conventional compound.

Comparative Example 3

Production of a Blue Light-Emitting OLED Device Comprising a Conventional Compound In Comparative Example 3, an OLED device was produced in the same manner as in Comparative Example 1, except that compound H-34 was used as a host of the light-emitting layer, and the electron transport material shown in Table 4 below was used as an electron transport material. The driving voltage and color coordinates based on a luminance of 1,000 nits, and the time taken to be reduced from 100% to 85% of the luminance based on a luminance of 2,000 nits (lifespan; T85) of the OLED device of Comparative Example 3 are provided in Table 4 below.

Device Example 4

Production of a Blue Light-Emitting OLED Device Comprising the Compound According to the Present Disclosure In Device Example 4, an OLED device was produced in the same manner as in Comparative Example 3, except that the electron transport material shown in Table 4 below was used as an electron transport material. The driving voltage and color coordinates based on a luminance of 1,000 nits, and the time taken to be reduced from 100% to 85% of the luminance based on a luminance of 2,000 nits (lifespan; T85) of the OLED device of Device Example 4 are provided in Table 4 below.

TABLE 4

| Electron Transport Material | Driving Voltage (V) | Color Coordinate (x) | Color Coordinate (y) | Lifespan T85 (hr) |
|---|---|---|---|---|
| Comparative Example 3 | Ref-1 | 3.8 | 0.139 | 0.092 | 44.0 |
| Device Example 4 | C-2 | 3.7 | 0.139 | 0.092 | 54.0 |

Table 4 shows that the organic electroluminescent device comprising the compound of the present disclosure has a lower driving voltage and better lifespan characteristics compared to the organic electroluminescent device comprising a conventional compound.

TABLE 5

Compounds used in Device Examples and Comparative Examples

Hole Injection Layer/ Hole Transport Layer

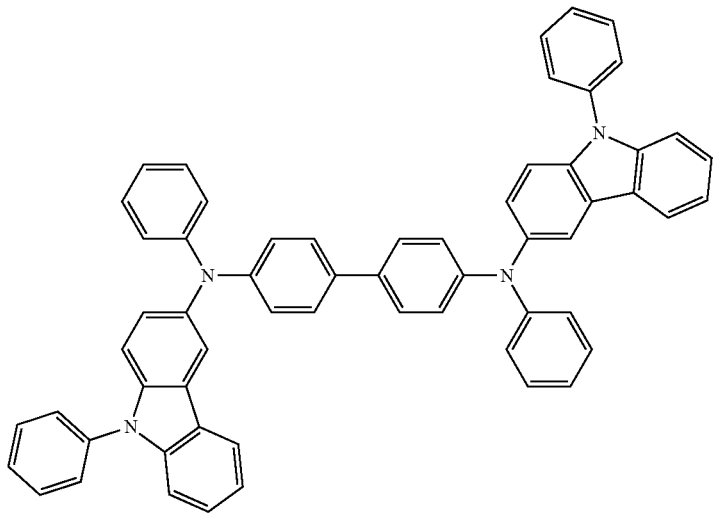 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1]

HI-1

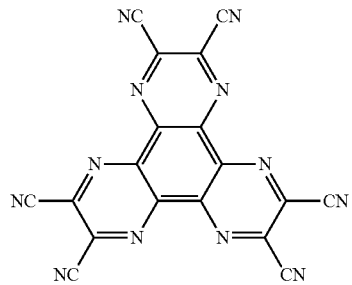 [SMILES: N#Cc1nc2c3nc(C#N)c(C#N)nc3c3nc(C#N)c(C#N)nc3c2nc1C#N]

HI-2

103 104
TABLE 5-continued
Compounds used in Device Examples and Comparative Examples
HT-1
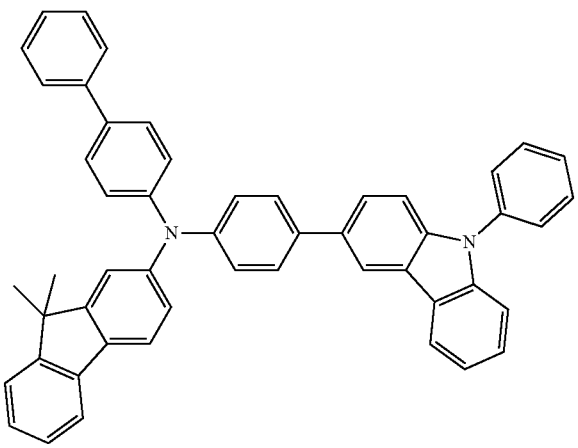 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
HT-2
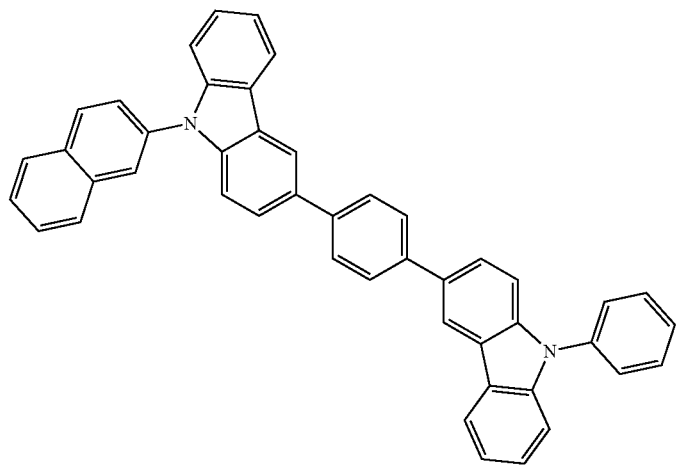 [SMILES: c1ccc(-n2c3ccccc3c3cc(-c4ccc(-c5ccc6c(c5)c5ccccc5n6-c5ccc6ccccc6c5)cc4)ccc32)cc1]
Light-Emitting Layer
H-15
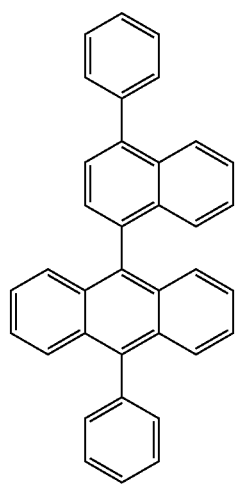 [SMILES: c1ccc(-c2ccc(-c3c4ccccc4c(-c4ccccc4)c4ccccc34)c3ccccc23)cc1]

TABLE 5-continued
Compounds used in Device Examples and Comparative Examples
H-34
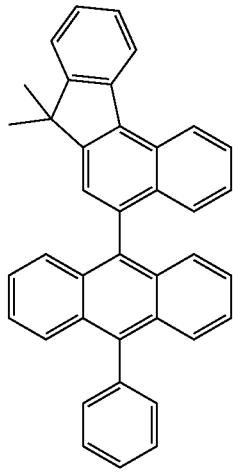 [SMILES: CC1(C)c2ccccc2-c2c1cc(-c1c3ccccc3c(-c3ccccc3)c3ccccc13)c1ccccc21]
D-38
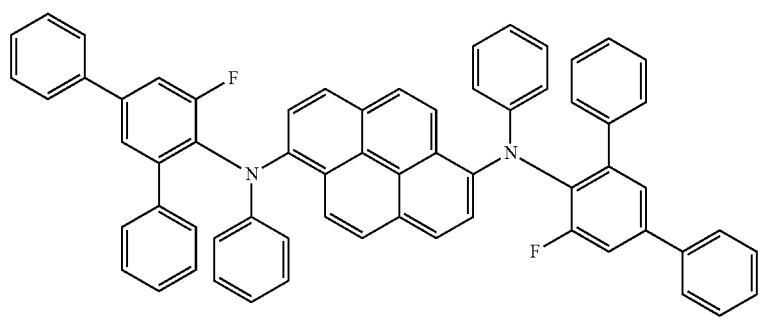 [SMILES: Fc1cc(-c2ccccc2)cc(-c2ccccc2)c1N(c1ccccc1)c1ccc2ccc3c(N(c4ccccc4)c4c(F)cc(-c5ccccc5)cc4-c4ccccc4)ccc4ccc1c2c43]
Electron Buffer Layer/ Electron Transport Layer/ Electron Injection Layer
C-2
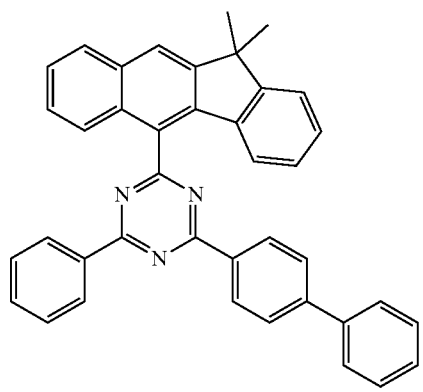 [SMILES: CC1(C)c2ccccc2-c2c1cc1ccccc1c2-c1nc(-c2ccccc2)nc(-c2ccc(-c3ccccc3)cc2)n1]

TABLE 5-continued
Compounds used in Device Examples and Comparative Examples
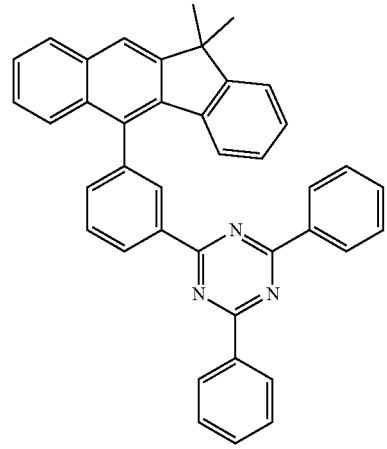 [SMILES: CC1(C)c2ccccc2-c2c1cc1ccccc1c2-c1cccc(-c2nc(-c3ccccc3)nc(-c3ccccc3)n2)c1]
C-22
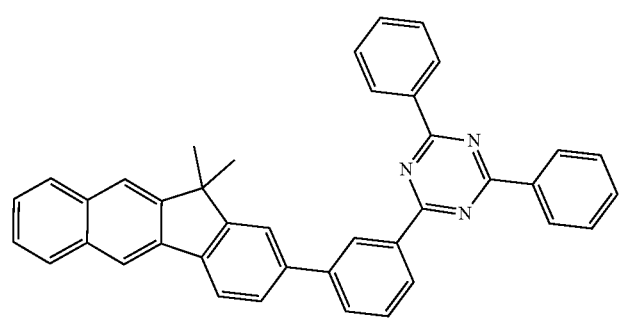 [SMILES: CC1(C)c2cc(-c3cccc(-c4nc(-c5ccccc5)nc(-c5ccccc5)n4)c3)ccc2-c2cc3ccccc3cc21]
Ref-1
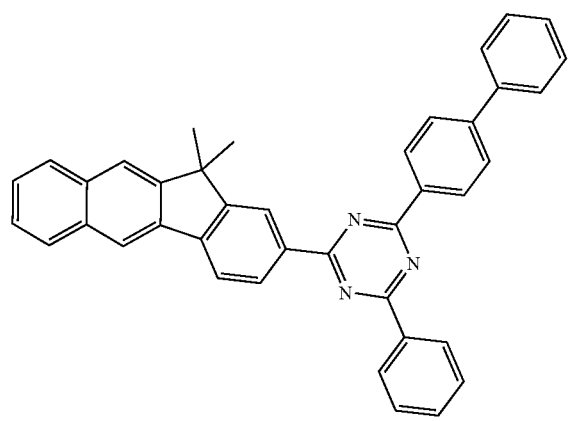 [SMILES: CC1(C)c2cc(-c3nc(-c4ccccc4)nc(-c4ccc(-c5ccccc5)cc4)n3)ccc2-c2cc3ccccc3cc21]
Ref-2

TABLE 5-continued

Compounds used in Device Examples and Comparative Examples

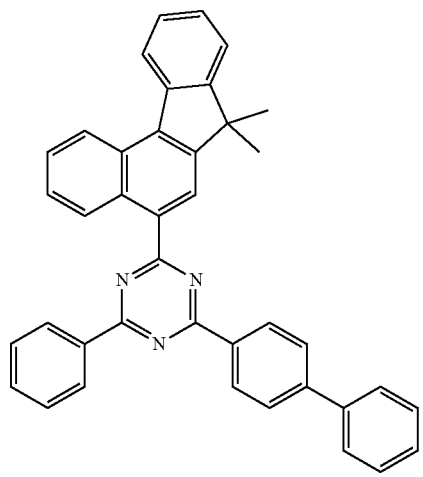 [SMILES: CC1(C)c2ccccc2-c2c1cc(-c1nc(-c3ccccc3)nc(-c3ccc(-c4ccccc4)cc3)n1)c1ccccc21]

Ref-4

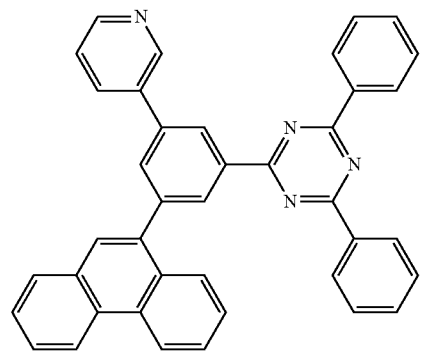 [SMILES: c1ccc(-c2nc(-c3ccccc3)nc(-c3cc(-c4cccnc4)cc(-c4cc5ccccc5c5ccccc45)c3)n2)cc1]

ET-1

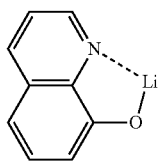

EI-1

The invention claimed is:

1. An organic electroluminescent compound represented by the following formula 1:

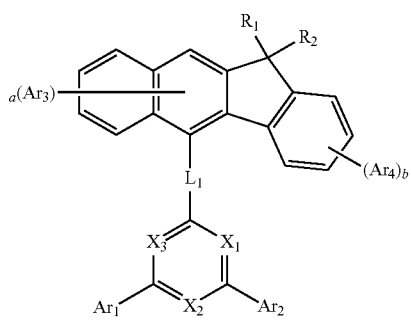

(1)

wherein $X_1$ to $X_3$ each independently represent CH or N, with a proviso that at least one of $X_1$ to $X_3$ are N;

$Ar_1$ and $Ar_2$ each independently represent a substituted or unsubstituted (C6-C30)aryl, or a substituted or unsubstituted (5- to 30-membered)heteroaryl;

$Ar_3$ and $Ar_4$ each independently represent hydrogen, deuterium, a halogen, a substituted or unsubstituted (C1-C30)alkyl, a substituted or unsubstituted (C6-C30)aryl, a substituted or unsubstituted (5- to 30-membered) heteroaryl, a substituted or unsubstituted (3- to 7-membered)heterocycloalkyl, or a substituted or unsubstituted (C3-C30)cycloalkyl;

$L_1$ represents a single bond, a substituted or unsubstituted (C6-C30)arylene, or a substituted or unsubstituted (5- to 30-membered)heteroarylene;

$R_1$ and $R_2$ each independently represent a substituted or unsubstituted (C1-C30)alkyl, a substituted or unsubstituted (C6-C30)aryl, or a substituted or unsubstituted (5- to 30-membered)heteroaryl; or are linked to each other to form an unsubstituted cyclopentane ring;

a represents an integer of 1 to 5, and b represents an integer of 1 to 4, in which if a and b represent an integer of 2 or more, each $Ar_3$ and each $Ar_4$ may be the same or different; and the heteroaryl(ene) and the heterocycloalkyl contain at least one heteroatom selected from B, N, O, S, Si, and P.

2. The organic electroluminescent compound according to claim 1, wherein $X_1$ to $X_3$ each independently represent CH or N, with a proviso that at least two of $X_1$ to $X_3$ are N;

$Ar_1$ and $Ar_2$ each independently represent a substituted or unsubstituted (C6-C25)aryl, or a substituted or unsubstituted (5- to 20-membered)heteroaryl;

$Ar_3$ and $Ar_4$ each independently represent hydrogen, a substituted or unsubstituted (C6-C20)aryl, or a substituted or unsubstituted (5- to 20-membered)heteroaryl;

$L_1$ represents a single bond, a substituted or unsubstituted (C6-C20)arylene, or a substituted or unsubstituted (5- to 20-membered)heteroarylene;

$R_1$ and $R_2$ each independently represent a substituted or unsubstituted (C1-C6)alkyl, or a substituted or unsubstituted (C6-C12)aryl; or are linked to each other to form an unsubstituted cyclopentane ring; and a and b each independently represent an integer of 1 to 2.

3. The organic electroluminescent compound according to claim 1, wherein $X_1$ to $X_3$ each independently represent N;

$Ar_1$ and $Ar_2$ each independently represent a (C6-C25)aryl unsubstituted or substituted with a (C1-C6)alkyl(s) or a (C6-C12)aryl(s), or a (5- to 20-membered)heteroaryl unsubstituted or substituted with a (C6-C12)aryl(s);

$Ar_3$ and $Ar_4$ each independently represent hydrogen, an unsubstituted (C6-C20)aryl, or an unsubstituted (5- to 20-membered)heteroaryl;

$L_1$ represents a single bond, an unsubstituted (C6-C20) arylene, or an unsubstituted (5- to 20-membered)heteroarylene;

$R_1$ and $R_2$ each independently represent an unsubstituted (C1-C6)alkyl, or an unsubstituted (C6-C12)aryl; or are linked to each other to form an unsubstituted cyclopentane ring; and a and b each independently represent 1.

4. The organic electroluminescent compound according to claim 1, wherein formula 1 is at least one selected from the group consisting of:

C-1

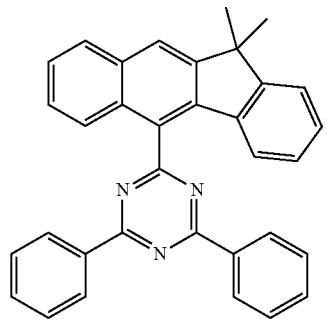

C-2

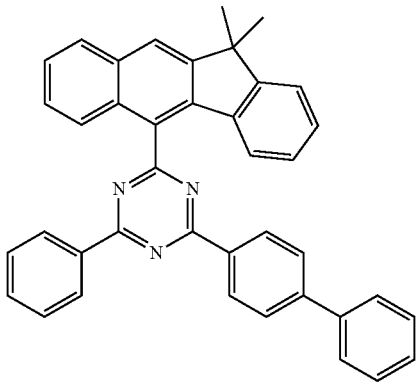

C-3

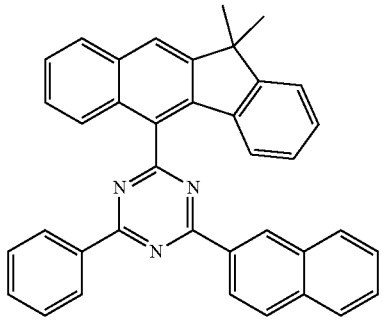

C-4

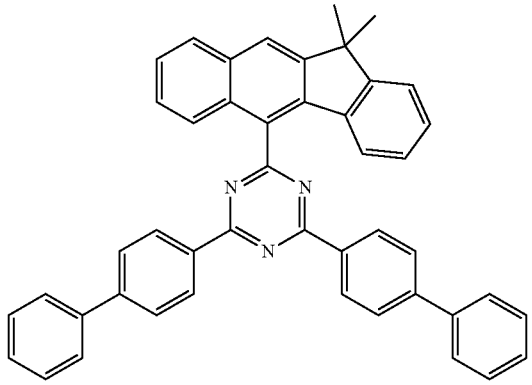

C-5

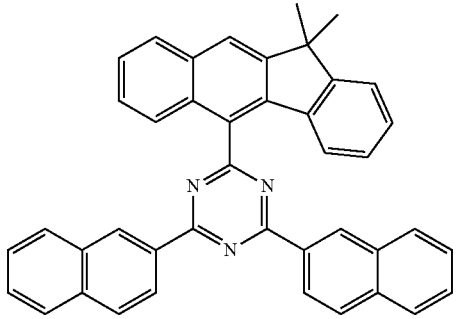

-continued
C-6
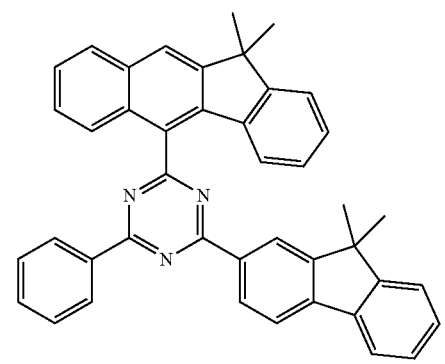
C-7
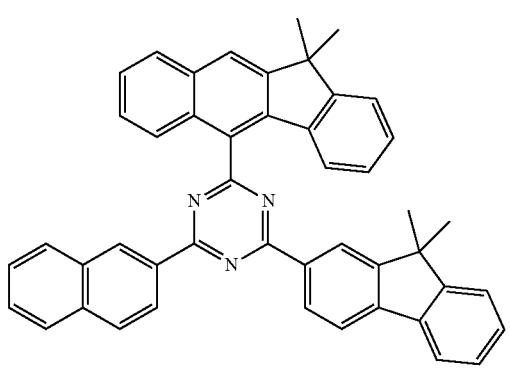
C-8
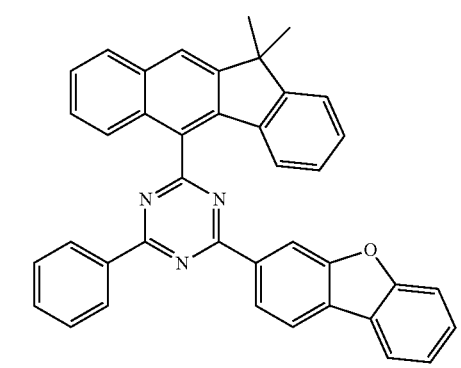
C-9
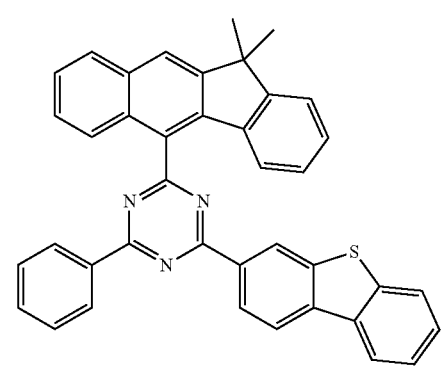
-continued
C-10
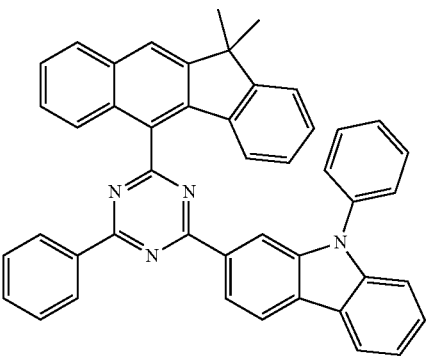
C-11
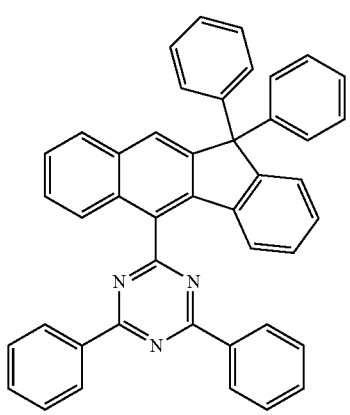
C-12
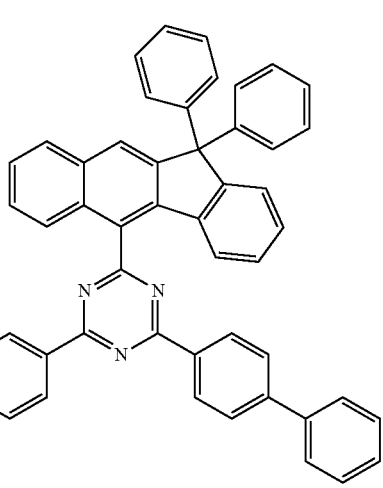
C-13
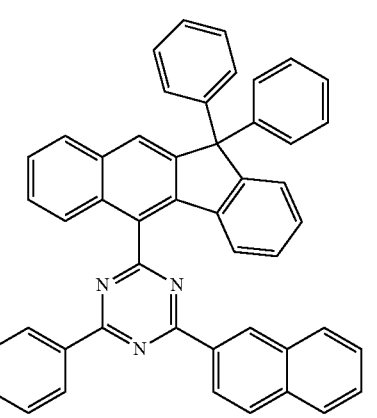

-continued
C-14
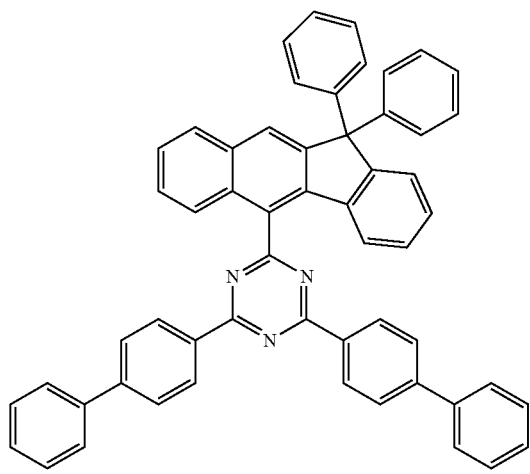
C-15
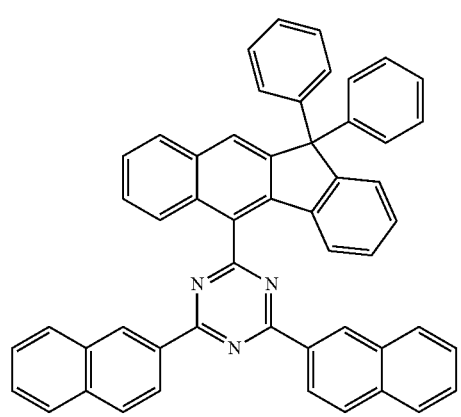
C-16
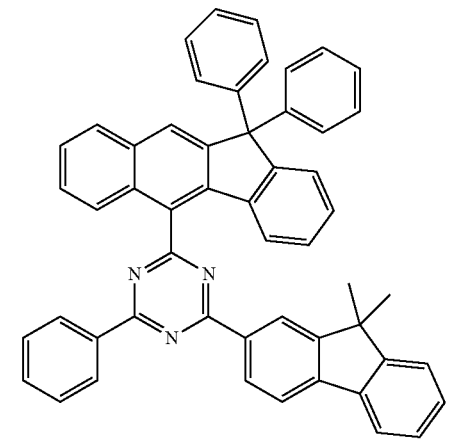
-continued
C-17
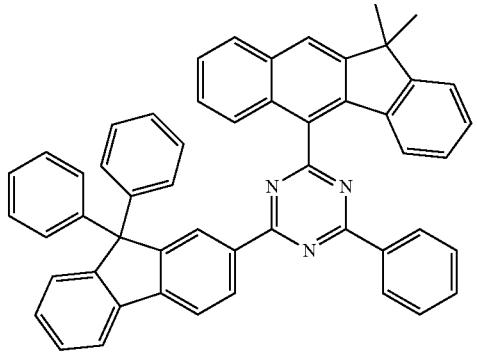
C-18
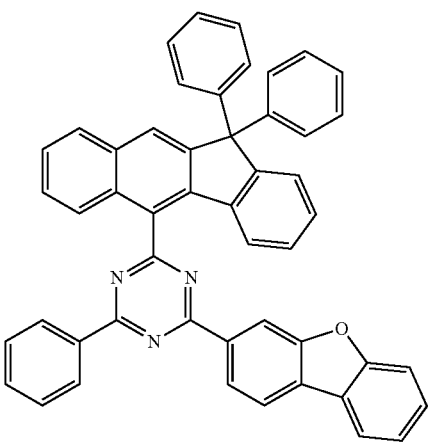
C-19
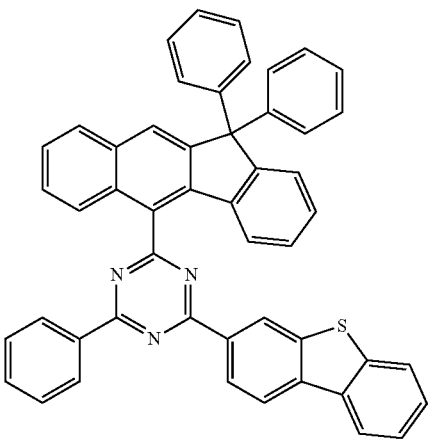

C-20
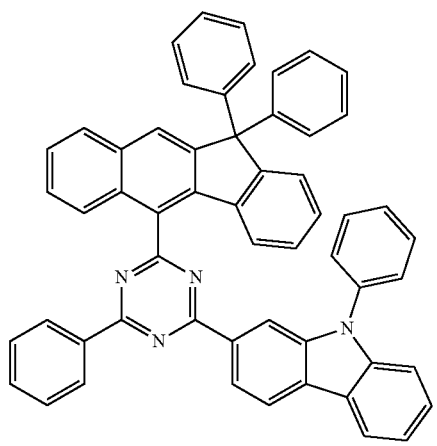
C-23
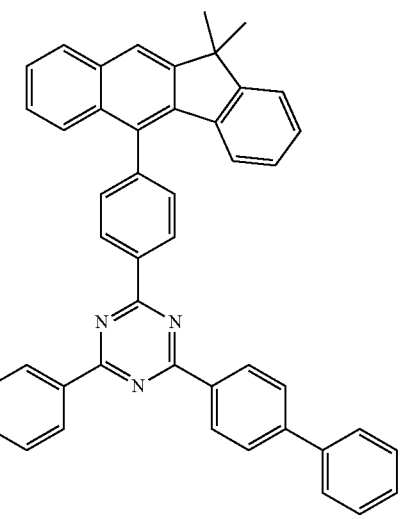
C-21
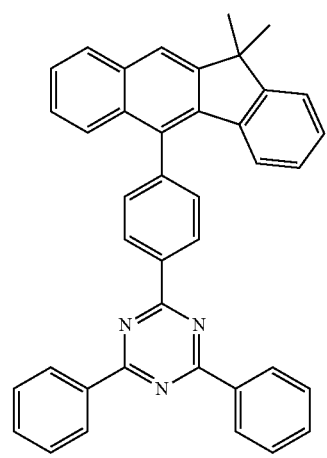
C-24
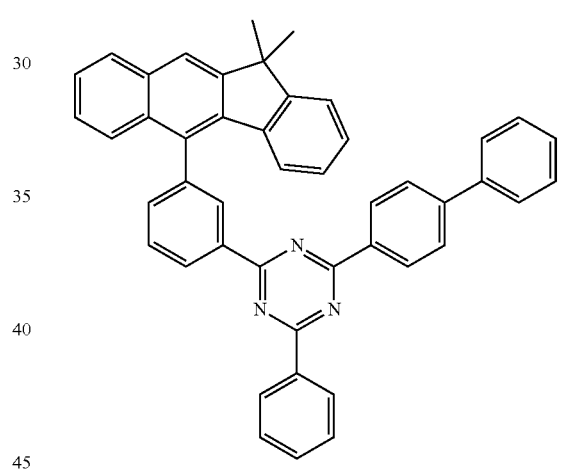
C-22
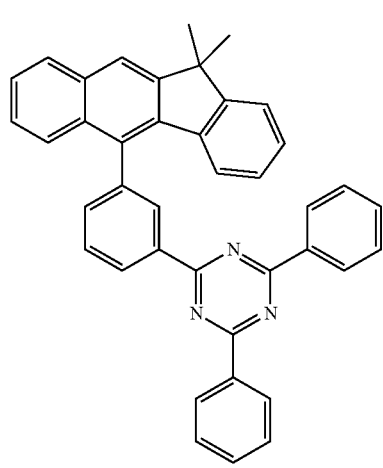
C-25
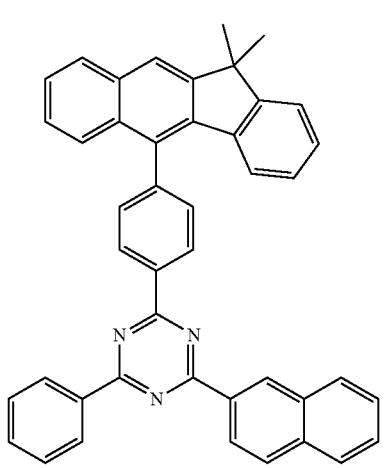

C-26
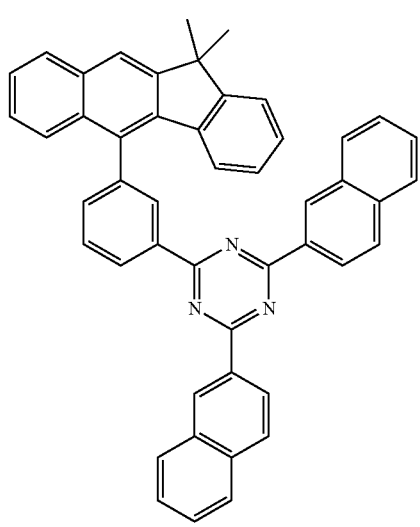
C-27
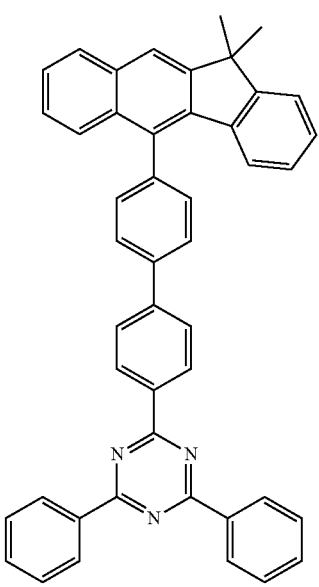
C-28
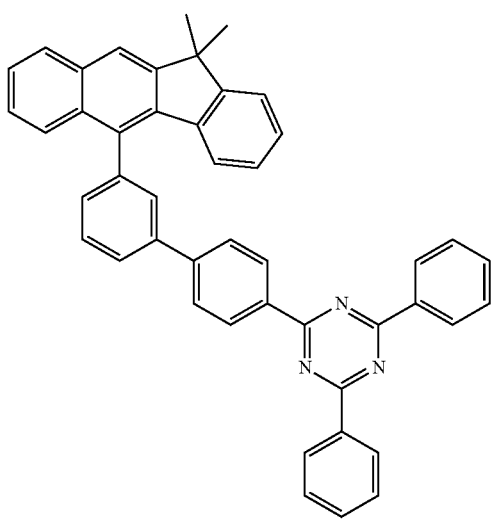
C-29
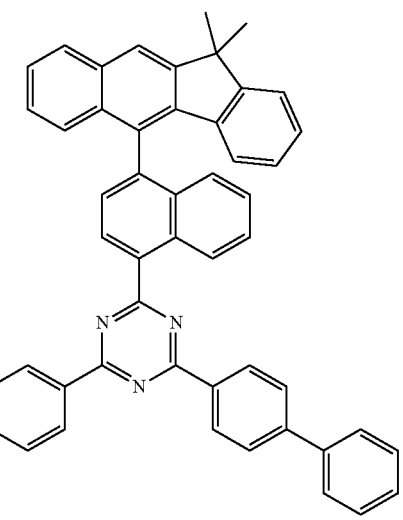
C-30
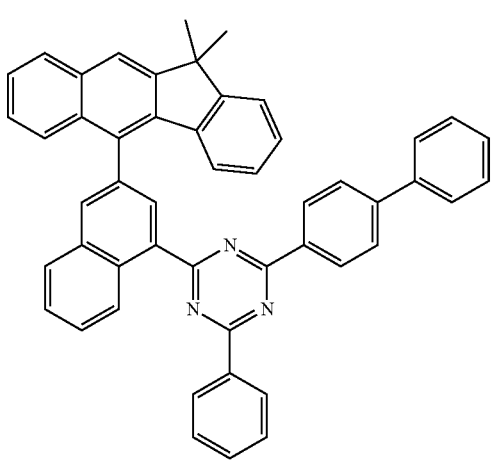
C-31
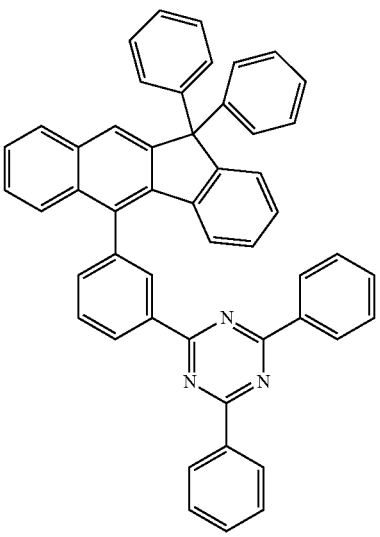

C-32
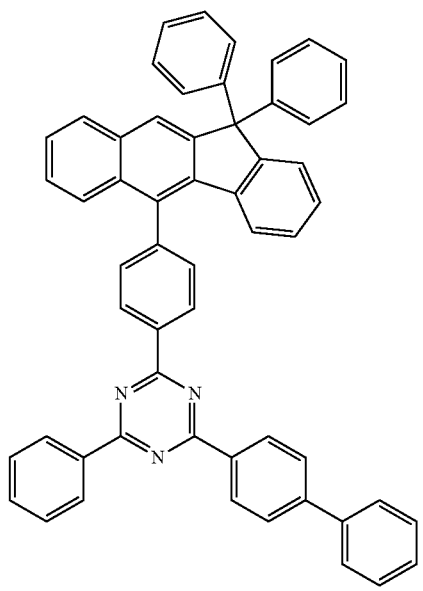
C-35
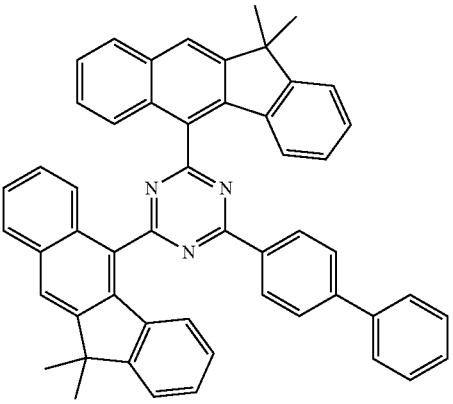
C-36
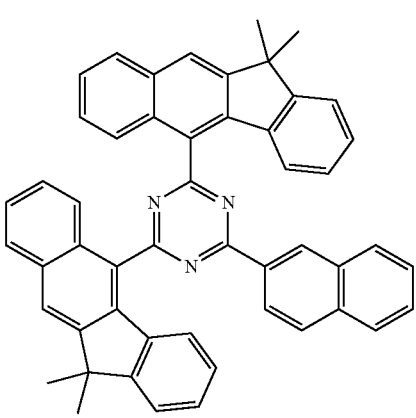
C-33
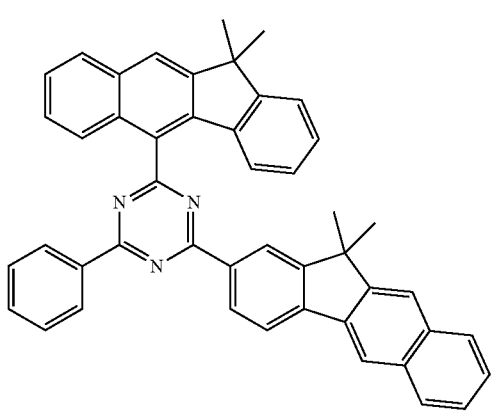
C-37
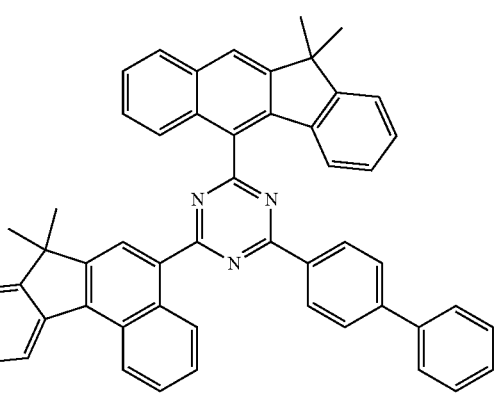
C-34
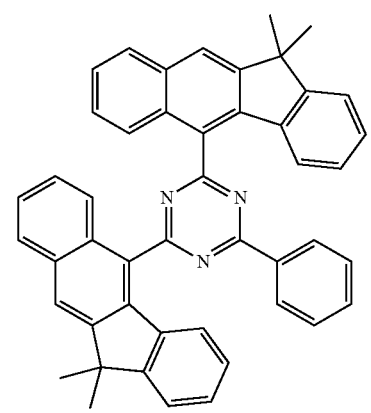
C-38
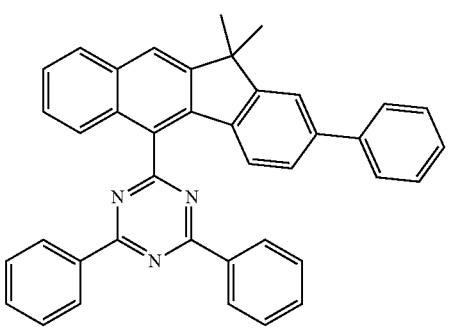

C-39
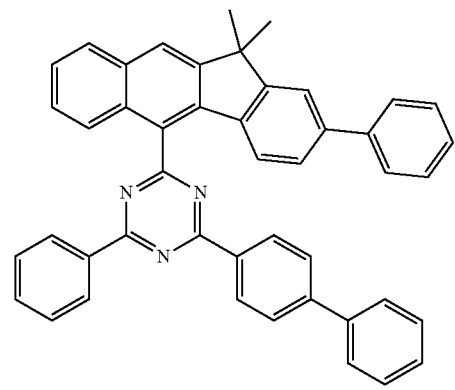
C-40
C-41
C-42
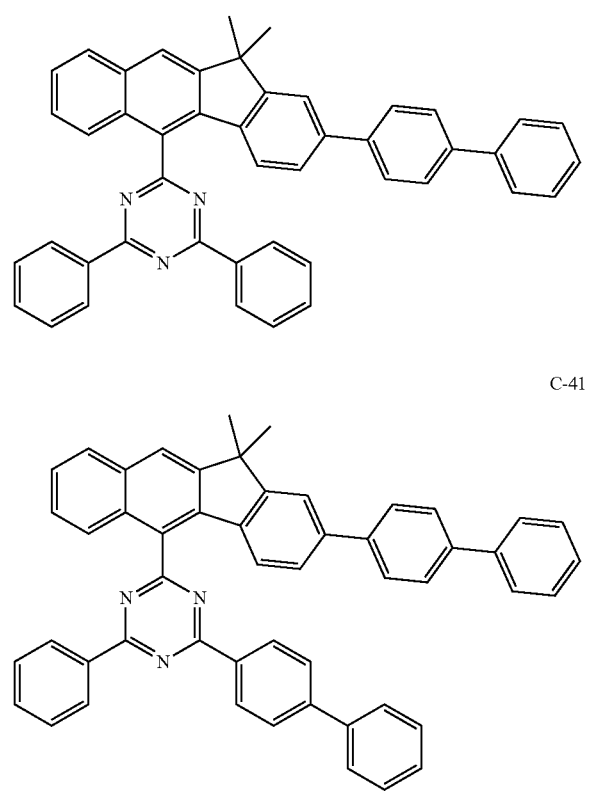
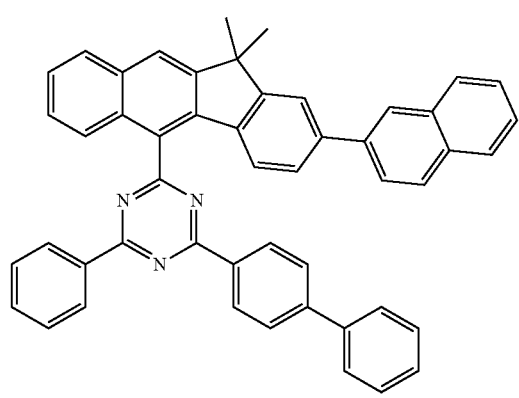
C-43
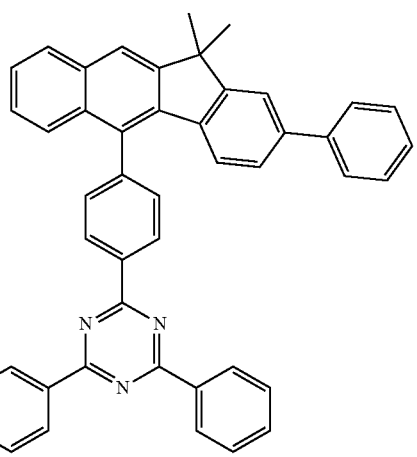
C-44
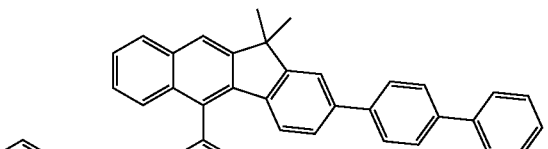
C-45
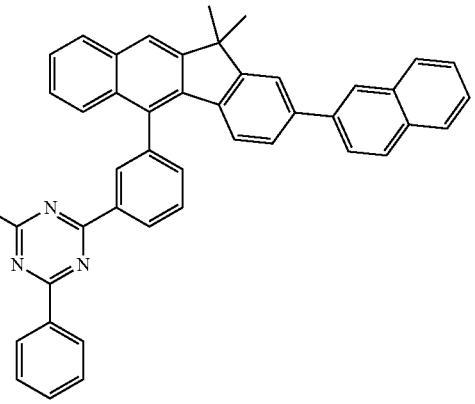

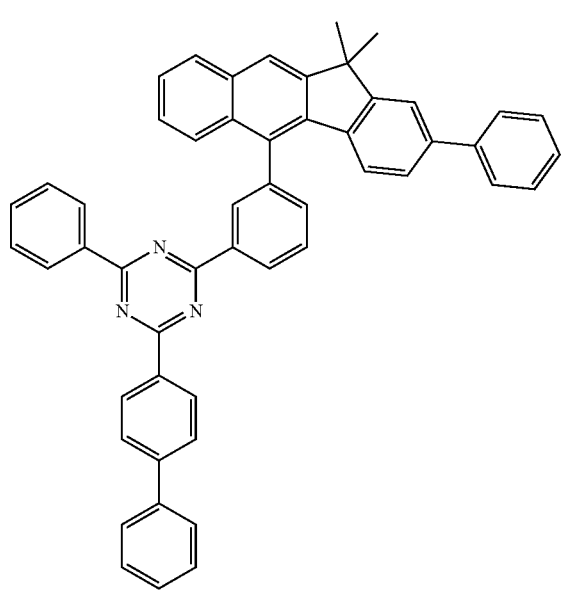
C-46
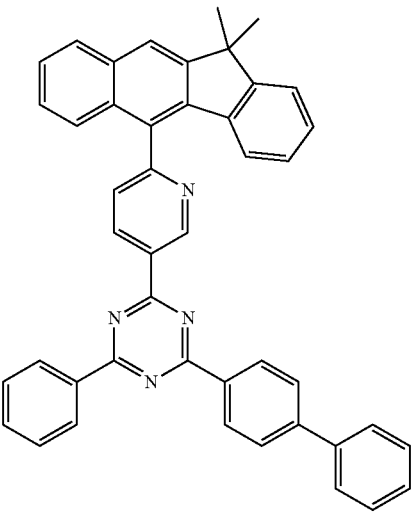
C-49
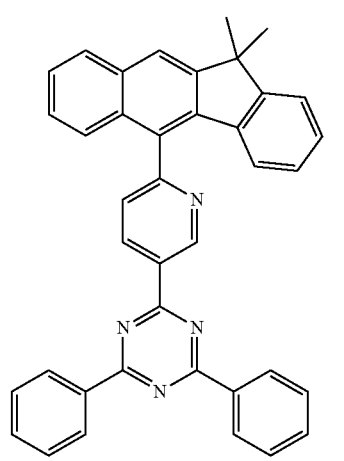
C-47
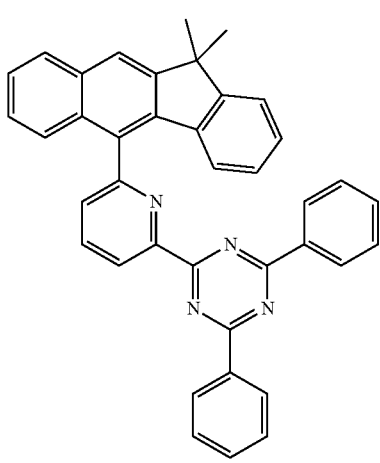
C-48
C-50
C-51

C-52
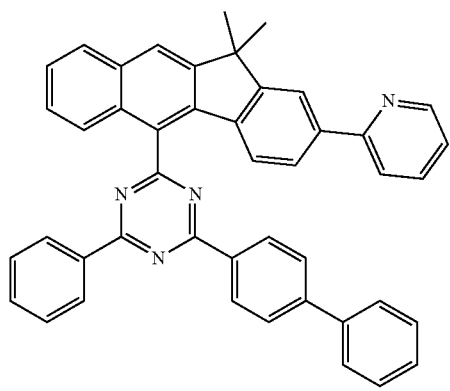
C-53
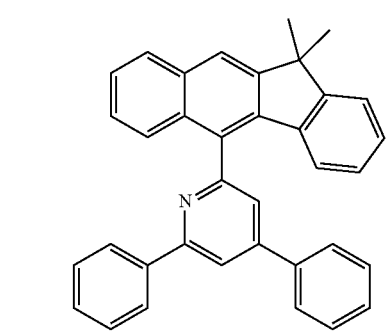
C-54
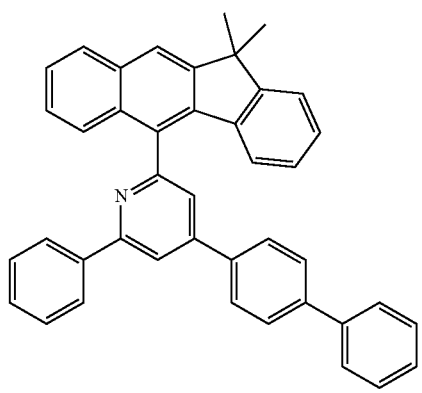
C-55
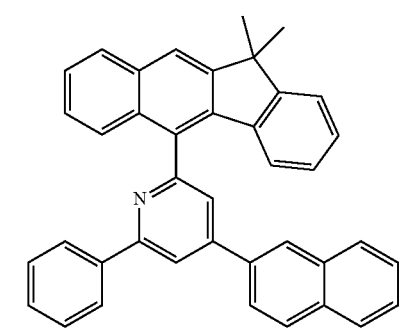
C-56
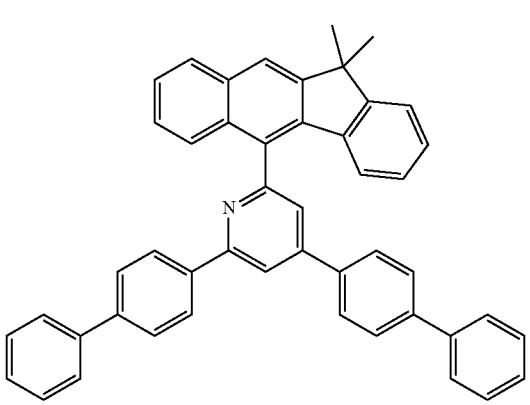
C-57
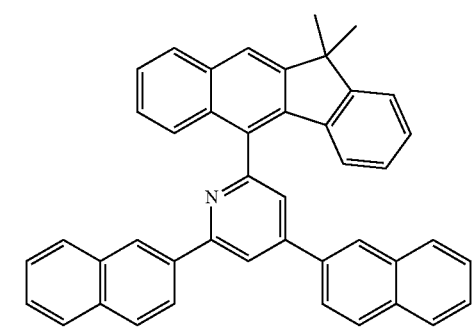
C-58
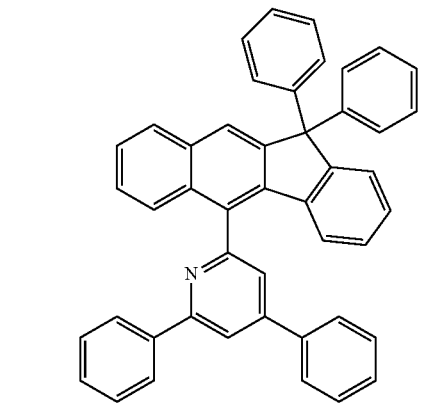
C-59
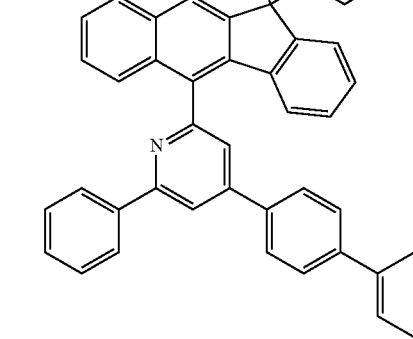

-continued
C-60
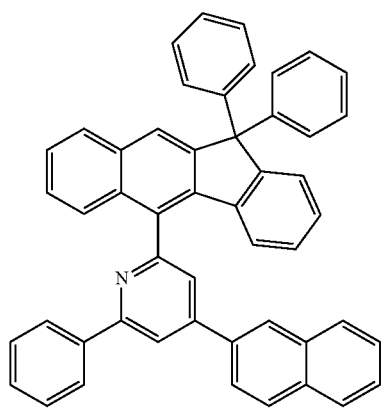
C-61
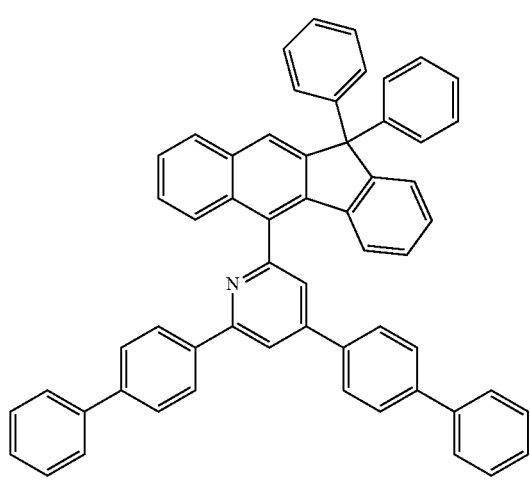
C-62
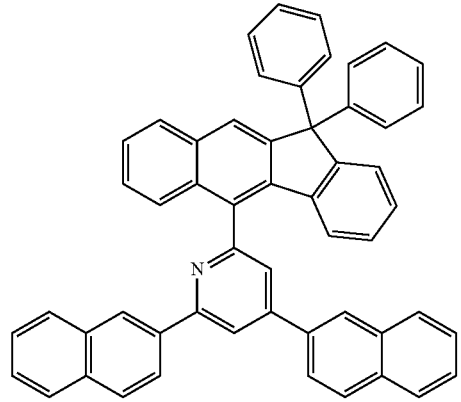
-continued
C-63
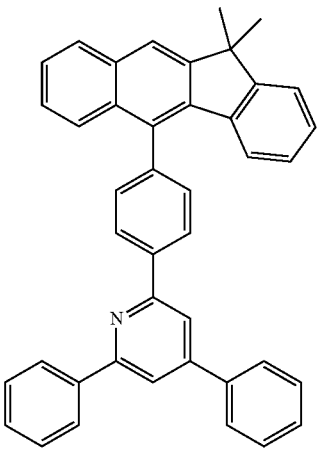
C-64
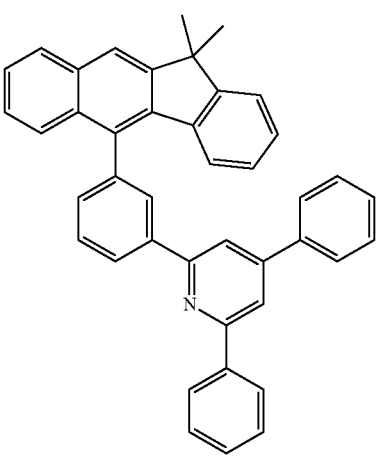
C-65
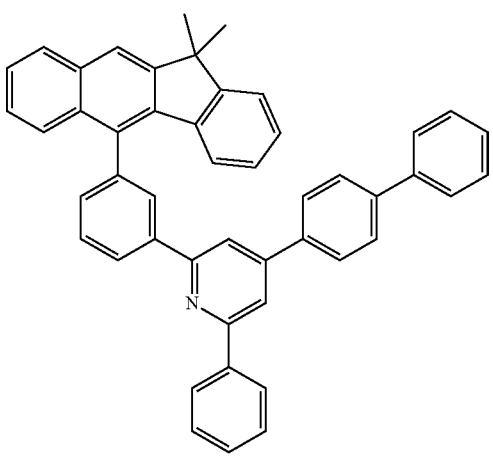

C-66
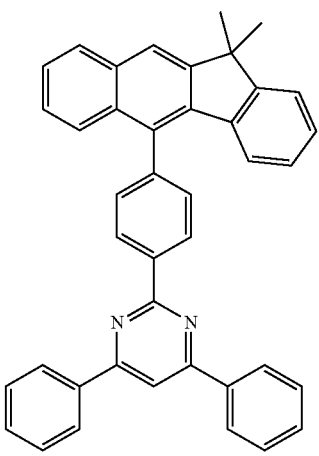
C-67
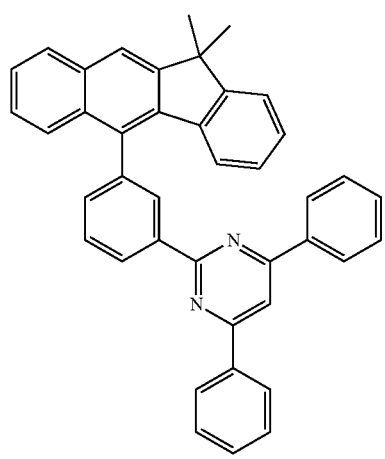
C-68
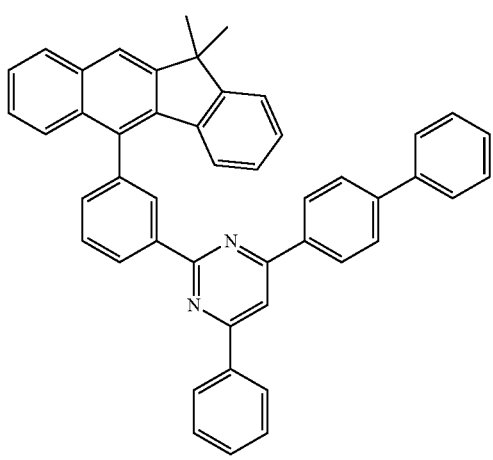
C-69
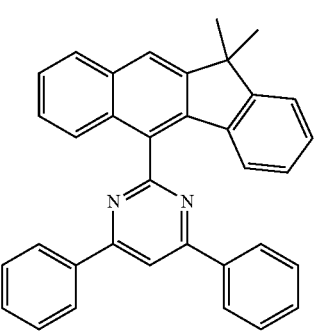
C-70
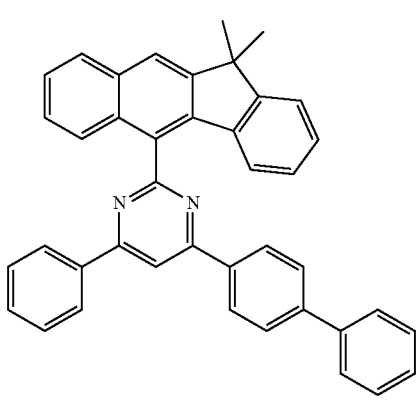
C-71
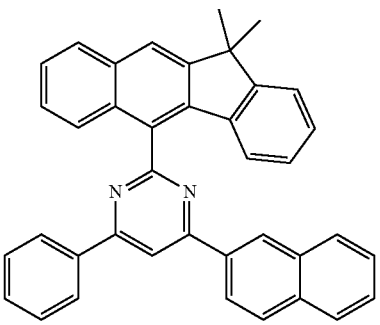
C-72
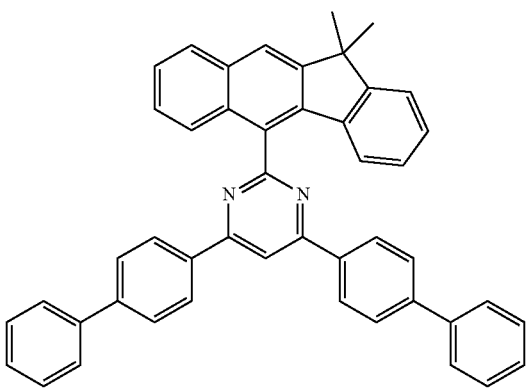

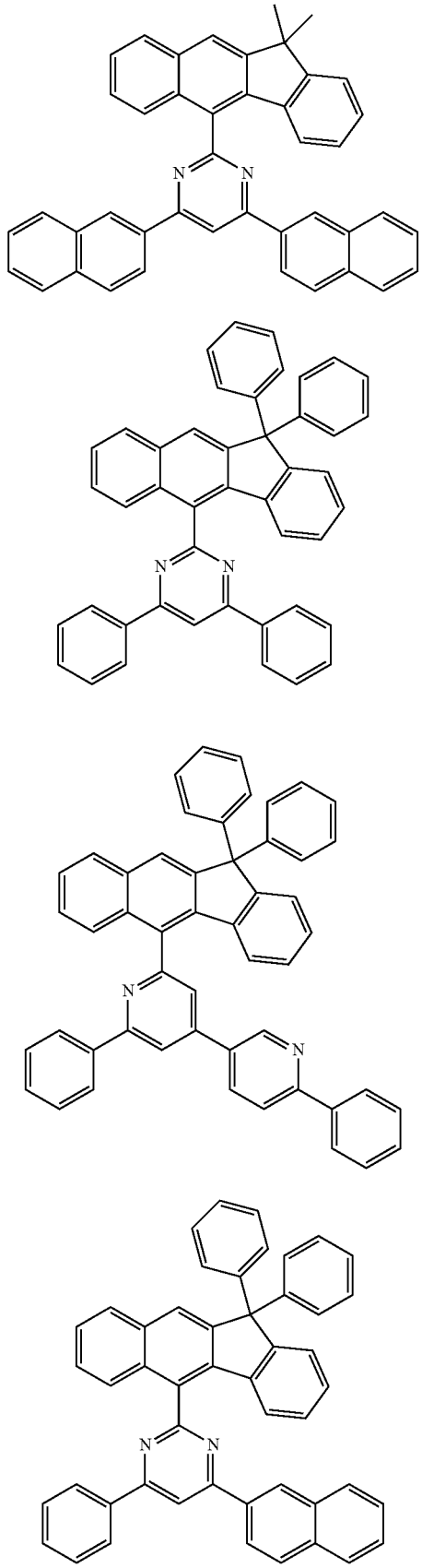

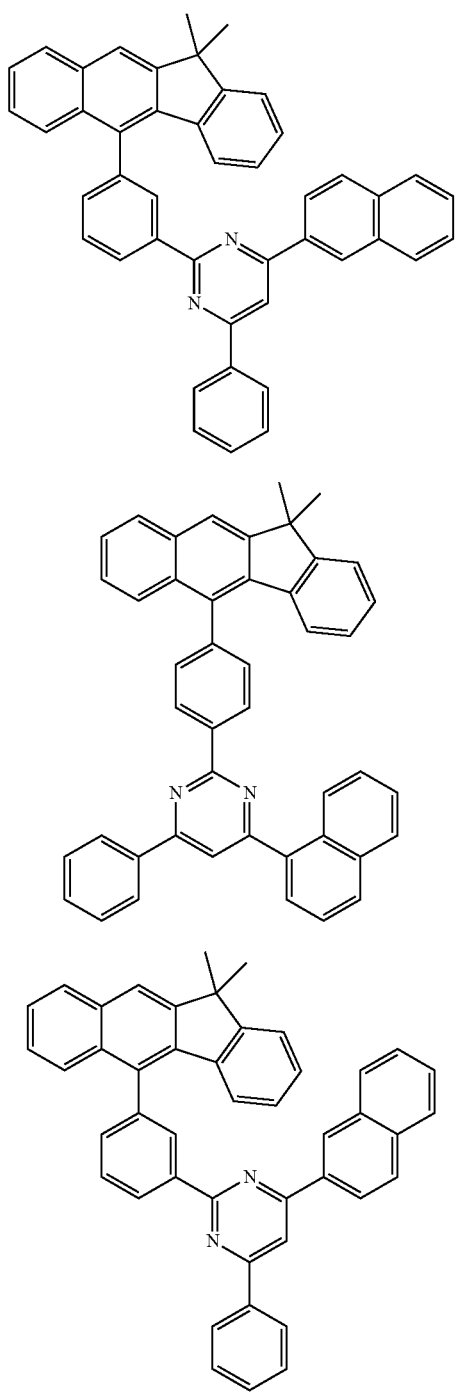

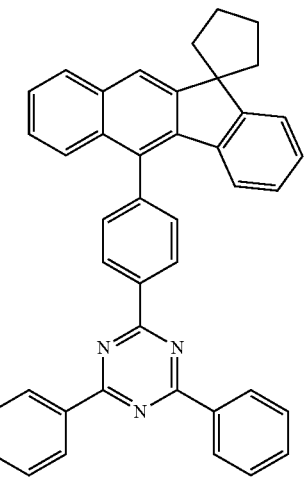

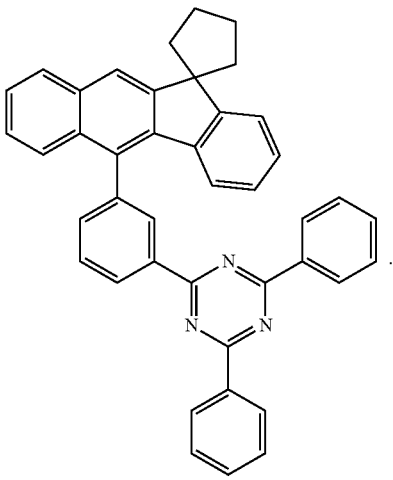

5. An organic electroluminescent material comprising the organic electroluminescent compound according to claim 1.

6. An organic electroluminescent device comprising the organic electroluminescent compound according to claim 1.

7. The organic electroluminescent device according to claim 6, wherein the organic electroluminescent compound is comprised in at least one of an electron buffer layer and an electron transport layer.

8. A display device comprising the organic electroluminescent compound according to claim 1.

* * * * *